US011434482B2

(12) United States Patent
Lombana et al.

(10) Patent No.: US 11,434,482 B2
(45) Date of Patent: Sep. 6, 2022

(54) METHODS OF IDENTIFYING BACTERIA COMPRISING BINDING POLYPEPTIDES

(71) Applicant: Genentech, Inc., South San Francisco, CA (US)

(72) Inventors: Twyla Noelle Lombana, San Francisco, CA (US); Rebekah McKenna, South San Francisco, CA (US); Christoph Spiess, Mountain View, CA (US); Karthik Veeravalli, South San Francisco, CA (US); Michael Dillon, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/782,616

(22) Filed: Oct. 12, 2017

(65) Prior Publication Data

US 2018/0030434 A1  Feb. 1, 2018

Related U.S. Application Data

(63) Continuation of application No. PCT/US2016/028945, filed on Apr. 22, 2016.

(60) Provisional application No. 62/152,537, filed on Apr. 24, 2015.

(51) Int. Cl.
| | | |
|---|---|---|
| G01N 33/53 | (2006.01) | |
| C12N 15/10 | (2006.01) | |
| C07K 16/22 | (2006.01) | |
| C07K 16/24 | (2006.01) | |
| C07K 14/195 | (2006.01) | |
| C07K 16/12 | (2006.01) | |
| C12Q 1/689 | (2018.01) | |
| G01N 33/569 | (2006.01) | |
| G01N 33/68 | (2006.01) | |

(52) U.S. Cl.
CPC ........ *C12N 15/1037* (2013.01); *C07K 14/195* (2013.01); *C07K 16/12* (2013.01); *C07K 16/22* (2013.01); *C07K 16/244* (2013.01); *C12Q 1/689* (2013.01); *G01N 33/5306* (2013.01); *G01N 33/56911* (2013.01); *G01N 33/686* (2013.01); *G01N 33/6854* (2013.01); *G01N 33/6857* (2013.01); *C07K 2317/30* (2013.01); *C07K 2317/92* (2013.01); *C07K 2317/94* (2013.01); *C07K 2319/40* (2013.01); *G01N 2469/20* (2013.01)

(58) Field of Classification Search
CPC ........ A61K 39/00; A61K 39/02; G01N 33/53; G01N 33/532
USPC ......... 424/234.1; 435/4, 6.1, 6.15, 6.19, 7.1, 435/7.2, 7.327, 8
See application file for complete search history.

(56) References Cited

U.S. PATENT DOCUMENTS

| | | |
|---|---|---|
| 5,200,341 A | 4/1993 | Obukowicz |
| 2004/0058403 A1 | 3/2004 | Harvey et al. |
| 2008/0076158 A1 | 3/2008 | Dassler et al. |

FOREIGN PATENT DOCUMENTS

| | | | |
|---|---|---|---|
| EP | 1905839 A1 | 4/2008 | |
| JP | 2006-515514 A | 6/2006 | |
| JP | 2008-073047 A | 4/2008 | |
| WO | WO-2005/019409 A2 | 3/2005 | |
| WO | WO-2005/095988 A2 | 10/2005 | |
| WO | WO2005/103074 A2 * | 11/2005 | ........... C07K 14/195 |
| WO | WO-2005/103074 A2 | 11/2005 | |

OTHER PUBLICATIONS

Mazor et al., "E-clonal antibodies: selection of full-length IgG antibodies using bacterial periplasmic display," Nat Protoc. 3(11):1766-77 (2008).
Ni et al., "Ipp deletion as a permeabilization method," Biotechnol Bioeng. 97(6):1347-56 (2007).
Rani et al., "Increased antibody affinity confers broad in vitro protection against escape mutants of severe acute respiratory syndrome coronavirus," J Virol. 86(17):9113-21 (2012).
International Preliminary Report on Patentability for International Patent Application No. PCT/US2016/028945, dated Oct. 24, 2017 (12 pages).
International Search Report and Written Opinion for International Patent Application No. PCT/US2016/028945, dated Nov. 22, 2016 (18 pages).
Invitation to Pay Additional Fees for International Patent Application No. PCT/US2016/028945, dated Aug. 16, 2016 (8 pages).
Notice of Reasons for Rejection for Japanese Patent Application No. 2017-555378, dated May 26, 2020 (12 pages).
Hirota et al., "On the process of cellular division in *Escherichia coli*: A mutant of E. coli lacking a murein-lipoprotein," Proc Natl Acad Sci U S A. 74(4):1417-20 (1977).
Kanamori et al., "Expression and excretion of human pancreatic secretory trypsin inhibitor in lipoprotein-deletion mutant of *Escherichia coli*," Gene. 66(2):295-300 (1988).

* cited by examiner

*Primary Examiner* — Jennifer E Graser
(74) *Attorney, Agent, or Firm* — Clark & Elbing LLP; Thomas J. Takara

(57) ABSTRACT

The invention provides methods of identifying bacteria comprising binding polypeptides. The invention also provides methods of identifying bacteria with improved expression of binding polypeptides. The invention also provides methods of identifying binding polypeptides with improved expression. The invention also provides engineered bacteria suitable for use in the methods of the invention. The invention also provides compositions that can be obtained using the methods, for example, anti-interleukin-13 (IL-13) antibodies with improved expression and/or stability. The invention also provides libraries comprising binding polypeptide (e.g., antibody) variants.

36 Claims, 31 Drawing Sheets
(11 of 31 Drawing Sheet(s) Filed in Color)
Specification includes a Sequence Listing.

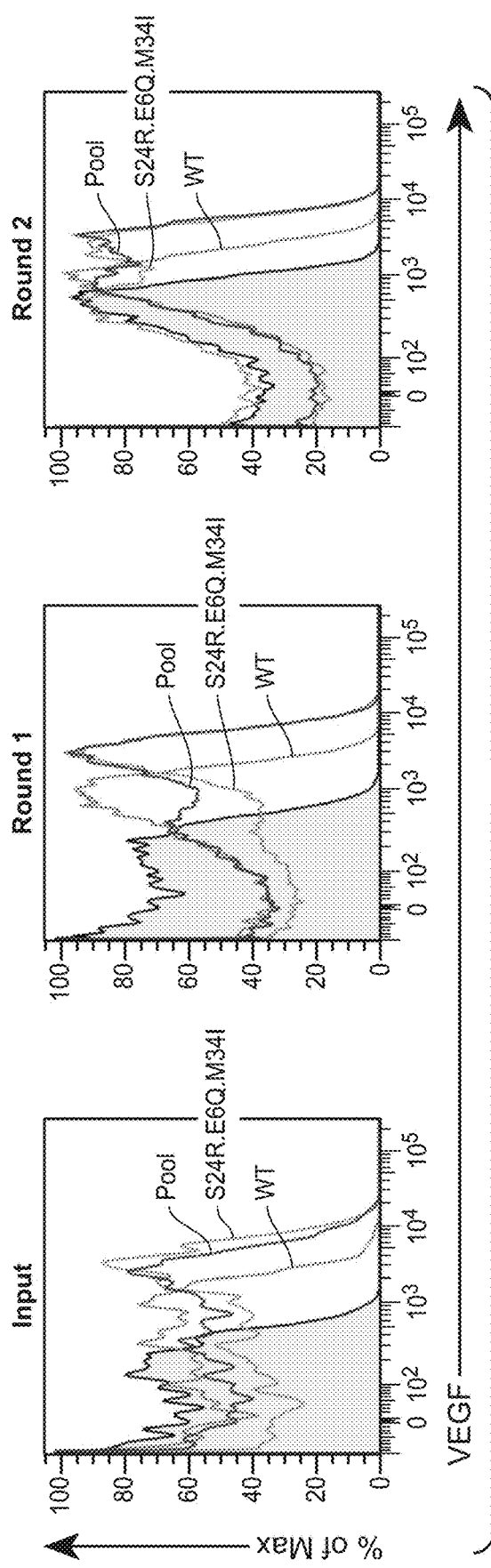
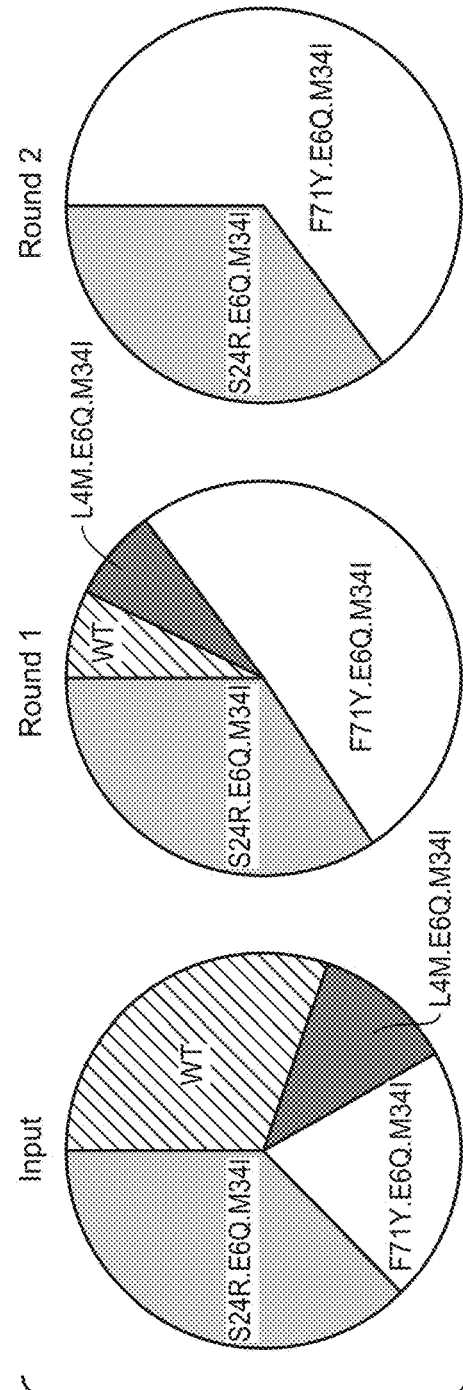
FIG. 3C
FIG. 3D

Anti-IL-13 Light Chain: V$_K$4

```
         FR1                          HVR1                   FR2                     HVR2
1                                                                                              56
DIVMTQSPDSLSVSLGERATINC RASKSVDSYGNSFMH WYQQKPGQPPKKLLIY LASNLES
       L                    A P V              A

FR3                                   HVR3              FR4
61                                                                    107
GVPDRFSGSGSGTDFTLTISSLQAEDVAVYYC QQNNEDPRT FGGGTKVEIK      (SEQ ID NO: 6)
```

Anti-IL-13 Heavy Chain: V$_H$2

```
         FR1                       HVR1               FR2                         HVR2
1                                                                                           60
QVTLRESGPALVKPTQTLTLTCTVSGFSLS AYSVNWIR QPPGKALEWLA MIWGDGKIVYN
    I  Q                       FT  S V           P
    L                          LY  D F
                                   L I
                                   G

FR3                               HVR3                           FR4
61                                                                              113
SALKSRLTISKDTSKNQVVLTMTNMDPVDTATYYC AGDGYYPYAMDN WGQGSLVTVSS      (SEQ ID NO: 5)
    R      F   V  V       G   T
    I      L   L  P       N
    L             V
    V
```

*FIG. 6*

Variable Heavy · Variable Light

Heavy Chain Subgroup 2 · Kappa Light Chain Subgroup 4

| Kabat # | Mutations | Kabat # | Mutations |
|---|---|---|---|
| 2 | I, L | 4 | L |
| 6 | Q | 12 | A |
| 24 | F, L | 15 | P |
| 25 | T, Y | 21 | V |
| 27 | S, D, L, G | 43 | A |
| 29 | V, F, I | | |
| 45 | P | | |
| 71 | R, I, L, V | | |
| 78 | F | | |
| 82 | V, L | | |
| 82c | V | | |
| 88 | G, P | | |
| 93 | T, N, V | | |

SEQUENCE LISTING

```
<160> NUMBER OF SEQ ID NOS: 32

<210> SEQ ID NO 1
<211> LENGTH: 111
<212> TYPE: PRT
<213> ORGANISM: Artificial Sequence
<220> FEATURE:
<223> OTHER INFORMATION: Synthetic Construct

<400> SEQUENCE: 1

Asp Ile Val Leu Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30
```

```
Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Glu Asp Pro Arg Thr Phe Gly Gly Gly Thr Lys Val Glu Ile Lys
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Synthetic Construct

<400> SEQUENCE: 2

Gln Val Thr Leu Arg Gln Ser Gly Pro Ala Leu Val Lys Pro Thr Gln
 1               5                  10                  15

Thr Leu Thr Leu Thr Cys Thr Val Ser Gly Phe Ser Leu Ser Ala Tyr
                 20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
 50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Gln Val Thr Leu Arg Glu Ser Gly Pro Ala Leu Val Lys Pro Thr Gln
 1               5                  10                  15

Thr Leu Thr Leu Thr Cys Thr Val Ser Gly Leu Ser Leu Ser Ala Tyr
                 20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
 50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95
```

```
Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Synthetic Construct

<400> SEQUENCE: 4

Gln Val Thr Leu Arg Gln Ser Gly Pro Ala Leu Val Lys Pro Thr Gln
1               5                   10                  15

Thr Leu Thr Leu Thr Cys Thr Val Ser Gly Leu Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 5
<211> LENGTH: 118
<212> TYPE: PRT
<213> ORGANISM: Artificial Sequence
<220> FEATURE:
<223> OTHER INFORMATION: Synthetic Construct

<400> SEQUENCE: 5

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 6
<211> LENGTH: 111
<212> TYPE: PRT
```

<213> ORGANISM: Artificial Sequence
<220> FEATURE:
<223> OTHER INFORMATION: Synthetic Construct

<400> SEQUENCE: 6

```
Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys
            100                 105                 110
```

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

```
Ala Tyr Ser Val Asn
1               5
```

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct

<400> SEQUENCE: 8

```
Met Ile Trp Gly Asp Gly Lys Ile Val Tyr Asn Ser Ala Leu Lys Ser
1               5                   10                  15
```

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

```
Asp Gly Tyr Tyr Pro Tyr Ala Met Asp Asn
1               5                   10
```

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

```
Arg Ala Ser Lys Ser Val Asp Ser Tyr Gly Asn Ser Phe Met His
1               5                   10                  15
```

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Leu Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Asn Asn Glu Asp Pro Arg Thr
1               5

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Asp Ile Val Leu Thr Gln Ser Pro Asp Ser Leu Ser Val Ser Leu Gly
1               5                   10                  15

Glu Arg Ala Thr Ile Asn Cys
            20

<210> SEQ ID NO 14
<211> LENGTH: 23
<212> TYPE: PRT
<213> ORGANISM: Artificial Sequence
<220> FEATURE:
<223> OTHER INFORMATION: Synthetic Construct

<400> SEQUENCE: 14

Asp Ile Val Met Thr Gln Ser Pro Asp Ser Leu Ser Val Ser Leu Gly
1               5                   10                  15

Glu Arg Ala Thr Ile Asn Cys
            20

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

Trp Tyr Gln Gln Lys Pro Gly Gln Pro Pro Lys Leu Leu Ile Tyr
1               5                   10                  15

<210> SEQ ID NO 16
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 16

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Phe Gly Gly Gly Thr Lys Val Glu Ile Lys
1               5                   10

<210> SEQ ID NO 18
<211> LENGTH: 30
<212> TYPE: PRT
<213> ORGANISM: Artificial Sequence
<220> FEATURE:
<223> OTHER INFORMATION: Synthetic Construct

<400> SEQUENCE: 18

Gln Val Thr Leu Arg Gln Ser Gly Pro Ala Leu Val Lys Pro Thr Gln
1               5                   10                  15

Thr Leu Thr Leu Thr Cys Thr Val Ser Gly Phe Ser Leu Ser
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic Construct

<400> SEQUENCE: 19

Gln Val Thr Leu Arg Glu Ser Gly Pro Ala Leu Val Lys Pro Thr Gln
1               5                   10                  15

Thr Leu Thr Leu Thr Cys Thr Val Ser Gly Leu Ser Leu Ser
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic Construct

<400> SEQUENCE: 20

Gln Val Thr Leu Arg Gln Ser Gly Pro Ala Leu Val Lys Pro Thr Gln
1               5                   10                  15

Thr Leu Thr Leu Thr Cys Thr Val Ser Gly Leu Ser Leu Ser
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic Construct
```

<400> SEQUENCE: 21

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser
            20                  25                  30

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Trp Ile Arg Gln Pro Pro Gly Lys Ala Leu Glu Trp Leu Ala
1               5                   10

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Gly
            20                  25                  30

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Trp Gly Gln Gly Ser Leu Val Thr Val Ser Ser
1               5                   10

<210> SEQ ID NO 25
<211> LENGTH: 31
<212> TYPE: DNA
<213> ORGANISM: Artificial Sequence
<220> FEATURE:
<223> OTHER INFORMATION: Synthetic Construct

<400> SEQUENCE: 25
tatgacgtcg attaatgcca aaagcggcag a                                31

<210> SEQ ID NO 26
<211> LENGTH: 31
<212> TYPE: DNA
<213> ORGANISM: Artificial Sequence
<220> FEATURE:
<223> OTHER INFORMATION: Synthetic Construct

<400> SEQUENCE: 26
tatagtactg attaatcgtc caggaagcta c                                31

<210> SEQ ID NO 27
<211> LENGTH: 23
<212> TYPE: DNA

```
<213> ORGANISM: Artificial Sequence
<220> FEATURE:
<223> OTHER INFORMATION: Synthetic Construct

<400> SEQUENCE: 27
ctattctcag aatgacttgg ttg                                    23

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28 atgctttct gtgactggtg                                         20

<210> SEQ ID NO 29
<211> LENGTH: 613
<212> TYPE: PRT
<213> ORGANISM: Escherichia coli

<400> SEQUENCE: 29
```

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
                275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
                340                 345                 350

Leu Thr Ile Glu Gln Val Lys Asp Ile Asn Arg Arg Met Ser Ile Gly
                355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
                500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
                580                 585                 590

Lys Ala Leu Arg Lys Leu Arg His Pro Ser Arg Ser Glu Val Leu Arg
    595                 600                 605

Ser Phe Leu Asp Asp
    610

<210> SEQ ID NO 30
<211> LENGTH: 292
<212> TYPE: PRT
<213> ORGANISM: Artificial Sequence
<220> FEATURE:
<223> OTHER INFORMATION: Synthetic Construct

<400> SEQUENCE: 30

Met Asn Lys Pro Trp Ser Glu Lys Leu His Asp Val Ser Glu Glu Val
1               5                   10                  15

His Arg Ala Leu Gln Lys Leu Gln Gln Ile Glu Glu Thr Gly Leu
                20                  25                  30

Thr Ile Glu Gln Val Lys Asp Ile Asn Arg Arg Met Ser Ile Gly Glu
        35                  40                  45

Ala Lys Ala Arg Arg Ala Lys Lys Glu Met Val Glu Ala Asn Leu Arg
    50                  55                  60

Leu Val Ile Ser Ile Ala Lys Lys Tyr Thr Asn Arg Gly Leu Gln Phe
65                  70                  75                  80

Leu Asp Leu Ile Gln Glu Gly Asn Ile Gly Leu Met Lys Ala Val Asp
                85                  90                  95

Lys Phe Glu Tyr Arg Arg Gly Tyr Lys Phe Ser Thr Tyr Ala Thr Trp
            100                 105                 110

Trp Ile Arg Gln Ala Ile Thr Arg Ser Ile Ala Asp Gln Ala Arg Thr
        115                 120                 125

Ile Arg Ile Pro Val His Met Ile Glu Thr Ile Asn Lys Leu Asn Arg
    130                 135                 140

Ile Ser Arg Gln Met Leu Gln Glu Met Gly Arg Glu Pro Thr Pro Glu
145                 150                 155                 160

Glu Leu Ala Glu Arg Met Leu Met Pro Glu Asp Lys Ile Arg Lys Val
                165                 170                 175

Leu Lys Ile Ala Lys Glu Ser Ile Ser Met Glu Thr Pro Ile Gly Asp
            180                 185                 190

Asp Lys Asp Ser His Leu Gly Asp Phe Ile Glu Asp Thr Thr Leu Glu
        195                 200                 205

Leu Pro Leu Asp Ser Ala Thr Thr Glu Ser Leu Arg Ala Ala Thr His
    210                 215                 220

Asp Val Leu Ala Gly Leu Thr Ala Arg Glu Ala Lys Val Leu Arg Met
225                 230                 235                 240

Arg Phe Gly Ile Asp Met Asn Thr Asp Tyr Thr Leu Glu Glu Val Gly
                245                 250                 255

Lys Gln Phe Asp Val Thr Arg Glu Arg Ile Arg Gln Ile Glu Ala Lys
            260                 265                 270

Ala Leu Arg Lys Leu Arg His Pro Ser Arg Ser Glu Val Leu Arg Ser
        275                 280                 285

Phe Leu Asp Asp
    290

<210> SEQ ID NO 31
<211> LENGTH: 47
<212> TYPE: PRT
<213> ORGANISM: Artificial Sequence
<220> FEATURE:
<223> OTHER INFORMATION: Synthetic Construct

<400> SEQUENCE: 31

Met Asn Thr Asp Phe Thr Leu Glu Glu Val Gly Lys Gln Phe Asp Val
1               5                   10                  15

Thr Arg Glu Arg Ile Arg Gln Ile Glu Ala Lys Ala Leu Arg Lys Leu
            20                  25                  30

Arg His Pro Ser Arg Ser Glu Val Leu Arg Ser Phe Leu Asp Asp
        35                  40                  45

<210> SEQ ID NO 32
<211> LENGTH: 613
<212> TYPE: PRT
<213> ORGANISM: Artificial Sequence
<220> FEATURE:

<223> OTHER INFORMATION: Synthetic Construct

<400> SEQUENCE: 32

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Leu Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr His Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Asp Leu Ala Pro
            165                 170                 175

Thr Ala Thr His Val Gly Ser Glu Leu Ser Gln Glu Asp Leu Asp Asp
        180                 185                 190

Asp Glu Asp Glu Asp Glu Glu Asp Gly Asp Asp Asp Ser Ala Asp Asp
    195                 200                 205

Asp Asn Ser Ile Asp Pro Glu Leu Ala Arg Glu Lys Phe Ala Glu Leu
210                 215                 220

Arg Ala Gln Tyr Ile Val Thr Arg Asp Thr Ile Asn Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Glu Thr Gly
            340                 345                 350

Leu Thr Ile Glu Gln Val Lys Asp Ile Asn Arg Arg Met Ser Ile Gly
        355                 360                 365

Glu Ala Lys Ala Arg Arg Ala Lys Lys Glu Met Val Glu Ala Asn Leu
    370                 375                 380

Arg Leu Val Ile Ser Ile Ala Lys Lys Tyr Thr Asn Arg Gly Leu Gln
385                 390                 395                 400
```

-continued

```
Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Ser Ile Ala Asp Gln Ala Arg
        435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Val Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
            515                 520                 525

Glu Leu Pro Leu Asp Ser Ala Thr Thr Glu Ser Leu Arg Ala Ala Thr
        530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
            595                 600                 605

Ser Phe Leu Asp Asp
    610
```

METHODS OF IDENTIFYING BACTERIA COMPRISING BINDING POLYPEPTIDES

SEQUENCE LISTING

The instant application contains a Sequence Listing which has been submitted electronically in ASCII format and is hereby incorporated by reference in its entirety. Said ASCII copy, created on Oct. 11, 2017, is named 50474-102002_Sequence_Listing_10.11.17_ST25 and is 26,399 bytes in size.

FIELD OF THE INVENTION

The present invention is directed to methods of identifying bacteria comprising binding polypeptides, methods of identifying binding polypeptides with improved expression, methods of identifying bacteria with improved expression of binding polypeptides, engineered bacteria suitable for use in the methods, compositions obtained using the methods, for example, antibodies with improved expression and/or stability (e.g., anti-interleukin-13 (IL-13) antibodies and anti-vascular endothelial growth factor (VEGF) antibodies with improved expression and/or stability), and libraries comprising binding polypeptide (e.g., antibody) variants.

BACKGROUND

Display of binding polypeptides (e.g., antibodies or fragments thereof) on the surface of bacteriophage or cells (e.g., bacterial, yeast, or mammalian cells) is a widely-used approach for protein engineering. While the rapid replication times of bacteria should offer bacterial display accelerated round-to-round progression compared to other cell display technologies, these advantages have been generally offset by compromises needed to retain a candidate binding polypeptide in the cell and maintain antigen accessibility. Displaying large molecules as fusions to bacterial outer membrane proteins can be difficult, limiting the application of these systems to peptides or small proteins. Another approach is the display of larger proteins in the periplasm. However, under most conditions, the outer membrane is impermeable to diffusion of hydrophilic molecules having a molecular weight greater than about 600 daltons into the periplasm (see, e.g., Decad et al. *J. Bacteriology* 128(1): 325-336, 1976). Current approaches of periplasmic display of binding polypeptides to larger ligands involve removal of the outer membrane, which necessitates tethering the binding polypeptide to the outer side of the inner membrane (e.g., by using fusion proteins or other tethers) to maintain the association of the binding polypeptide with the bacterial inner membrane. Further, destruction of the outer membrane results in cell death, which necessitates time-consuming molecular manipulation between rounds of bacterial display.

Therefore, there remains a need for improved methods for live-cell bacterial display that are compatible with full-length binding polypeptides (e.g., antibodies) and target molecules (e.g., antigens) which can be used, for example, to identify protein variants having desired characteristics (e.g., improved expression, stability, and/or affinity), as well as to identify bacteria having improved expression of binding polypeptides.

SUMMARY

The present invention is directed to methods of identifying bacteria that harbor desired binding polypeptides, methods of identifying binding polypeptides with improved expression, methods of identifying bacteria with improved expression of binding polypeptides, engineered bacteria suitable for use in the methods of the invention, compositions obtained using the methods, for example, antibodies (e.g., anti-IL-13 and anti-VEGF antibodies) with improved expression and/or stability, and libraries comprising binding polypeptide (e.g., antibody) variants.

In one aspect, the invention features a method for identifying a bacterium comprising a binding polypeptide that specifically binds a target molecule, the method comprising the steps of: (a) providing a bacterium having an outer membrane permeable to a molecule having a molecular weight greater than 10 kDa, the bacterium expressing a nucleic acid encoding a candidate binding polypeptide, wherein the candidate binding polypeptide is present within the periplasm of the bacterium; (b) contacting the bacterium with a detectably labeled target molecule; and (c) identifying the bacterium as comprising a binding polypeptide by the presence of the labeled target molecule within the periplasm, wherein the bacterium remains viable following step (c). In some embodiments, the target molecule has a molecular weight less than 250 kDa. In some embodiments, the target molecule has a molecular weight less than 150 kDa.

In another aspect, the invention features a method for identifying a bacterium with improved expression of a binding polypeptide that specifically binds a target molecule, the method comprising the steps of: (a) providing a bacterium having an outer membrane permeable to a molecule having a molecular weight greater than 10 kDa, the bacterium expressing a nucleic acid encoding a binding polypeptide, wherein the binding polypeptide is present within the periplasm of the bacterium; (b) contacting the bacterium with a detectably labeled target molecule; and (c) identifying the bacterium as having improved expression of the binding polypeptide by the presence of the labeled target molecule within the periplasm, wherein the bacterium remains viable following step (c). In some embodiments, the target molecule has a molecular weight less than 250 kDa. In some embodiments, the target molecule has a molecular weight less than 150 kDa.

In another aspect, the invention features a method for identifying a bacterium comprising a binding polypeptide that specifically binds a target molecule, the method comprising the steps of: (a) providing a bacterium comprising a mutation that allows for diffusion of membrane-impermeant molecules across the outer membrane into the periplasm, the bacterium expressing a nucleic acid encoding a candidate binding polypeptide, wherein the candidate binding polypeptide is present within the periplasm of the bacterium; (b) contacting the bacterium with a detectably labeled target molecule; and (c) identifying the bacterium as comprising a binding polypeptide by the presence of the labeled target molecule within the periplasm, wherein the bacterium remains viable following step (c).

In another aspect, the invention features a method for identifying a bacterium with improved expression of a binding polypeptide that specifically binds a target molecule, the method comprising the steps of: (a) providing a bacterium comprising a mutation that allows for diffusion of membrane-impermeant molecules across the outer membrane into the periplasm, the bacterium expressing a nucleic acid encoding a binding polypeptide, wherein the binding polypeptide is present within the periplasm of the bacterium; (b) contacting the bacterium with a detectably labeled target molecule; and (c) identifying the bacterium as having improved expression of the binding polypeptide by the presence of the labeled target molecule within the periplasm, wherein the bacterium remains viable following step (c).

In some embodiments of any of the preceding aspects, the method further comprises subjecting the bacterium to conditions that permeabilize the outer membrane of the bacterium prior to step (b). In some embodiments, the method further comprises resealing the outer membrane of the bacterium following contacting the bacterium with a detectably labeled target molecule.

In another aspect, the invention features a method for identifying a bacterium comprising a binding polypeptide that specifically binds a target molecule, the method comprising the steps of: (a) providing a bacterium expressing a nucleic acid encoding a candidate binding polypeptide, wherein the candidate binding polypeptide is present within the periplasm of the bacterium; (b) subjecting the bacterium to conditions that permeabilize the outer membrane of the bacterium; (c) contacting the bacterium with a detectably labeled target molecule; (d) resealing the outer membrane of the bacterium following step (c); and (e) identifying the bacterium as comprising a binding polypeptide by the presence of the labeled target molecule within the periplasm. In another aspect, the invention features a method for identifying a bacterium with improved expression of a binding polypeptide that specifically binds a target molecule, the method comprising the steps of: (a) providing a bacterium expressing a nucleic acid encoding a binding polypeptide, wherein the binding polypeptide is present within the periplasm of the bacterium; (b) subjecting the bacterium to conditions that permeabilize the outer membrane of the bacterium; (c) contacting the bacterium with a detectably labeled target molecule; (d) resealing the outer membrane of the bacterium following step (c); and (e) identifying the bacterium as having improved expression of the binding polypeptide by the presence of the labeled target molecule within the periplasm.

In some embodiments of any of the preceding aspects, the method further comprises repeating the steps of the method at least once without an intervening step of isolating the nucleic acid. In some embodiments, the method further comprises incubating the bacterium in growth medium prior to repeating the method.

In some embodiments of any of the preceding aspects, the bacterium comprises a mutation that allows for diffusion of membrane-impermeant molecules across the outer membrane into the periplasm. In some embodiments, the mutation is in a gene encoding an outer membrane protein or a protein that affects lipopolysaccharide (LPS) composition. In some embodiments, the outer membrane protein is major outer membrane lipoprotein Lpp (Lpp), a porin, or TolC. In some embodiments, the protein that affects LPS composition is selected from RfaD, RfaE, RfaH, RfaRd, TolA, TolB, and TolD.

In some embodiments of any of the preceding aspects, subjecting the bacterium to conditions that permeabilize the outer membrane of the bacterium comprises treating the bacterium with a permeabilization agent. In some embodiments, the permeabilization agent is selected from the group consisting of a divalent cation chelator, NaCl, sucrose, an antibiotic, a detergent, lysozyme, Tris, Tris-EDTA, ascorbate, polylysine, benzalkonium chloride, protamine, bactericidal/permeability increasing protein (BPI), serum, complement, and $Ca^{2+}$. In some embodiments, the divalent cation chelator is EDTA. In some embodiments, the antibiotic is selected from the group consisting of an aminoglycoside, polymyxin B, deacylated polymyxin, octapeptin, and benzyl penicillin.

In some embodiments of any of the preceding aspects, resealing the outer membrane of the bacterium comprises contacting the bacterium with a salt of a cation selected from $Mg^{2+}$, $Mn^{2+}$, $Ca^{2+}$, $Zn^{2+}$, $Fe^{2+}$, $Na^+$, or $K^+$. In some embodiments, the cation is $Mg^{2+}$. In some embodiments, the salt of $Mg^{2+}$ is $MgCl_2$.

In some embodiments of any of the preceding aspects, the contacting step further comprises contacting the bacterium with a nucleic acid dye. In some embodiments, the nucleic acid dye is selected from the group consisting of SYTO® 9, SYTO® 41, SYTO® 43, SYTO® 42, SYTO®44, SYTO® 40, and SYTO® 45. In some embodiments, the nucleic acid dye is SYTO® 9 or SYTO® 41.

In some embodiments of any of the preceding aspects, the detectably labeled target molecule comprises a fluorescent label. In some embodiments, the fluorescent label comprises a fluorescent dye or a fluorescent polypeptide. In some embodiments, the fluorescent dye is selected from the group consisting of: an ALEXA® dye or a DYLIGHT® dye. In some embodiments, the ALEXA® dye is ALEXA FLUOR® 488 or ALEXA FLUOR® 647. In some embodiments, the DYLIGHT® dye is DYLIGHT® 649.

In some embodiments of any of the preceding aspects, the method further comprises at least one wash step comprising resuspending the bacterium in a wash buffer following contacting the bacterium with the detectably labeled target molecule.

In some embodiments of any of the preceding aspects, the identifying step comprises flow cytometry. In some embodiments, the flow cytometry comprises sorting for single cells and sorting based on the signal of the detectably labeled target molecule. In some embodiments, the method further comprises sorting based on the signal of a nucleic acid dye. In some embodiments, the flow cytometry comprises sequentially (i) sorting based on the signal of a nucleic acid dye; (ii) sorting for single cells; and (iii) sorting based on the signal of the detectably labeled target molecule.

In some embodiments of any of the preceding aspects, the bacterium is a gram-negative bacterium. In some embodiments, the gram-negative bacterium is an *E. coli* bacterium.

In some embodiments of any of the preceding aspects, the binding polypeptide is expressed in soluble form in the periplasm of the bacterium.

In some embodiments of any of the preceding aspects, the binding polypeptide is an antibody. In some embodiments, the antibody is a full-length antibody. In some embodiments, the antibody is an IgG antibody. In some embodiments, the antibody is a half-antibody. In some embodiments, the antibody is an antibody fragment. In some embodiments, the antibody fragment is selected from the group consisting of Fab, Fab'-SH, Fv, scFv, and $(Fab')_2$ fragments.

In some embodiments of any of the preceding aspects, step (a) comprises providing a plurality of bacteria, wherein the plurality of bacteria comprise a library of nucleic acids, each encoding a candidate binding polypeptide. In some embodiments, the library comprises a plurality of nucleic acids encoding candidate antibody variants, wherein each candidate antibody variant comprises an amino acid residue alteration in an FR of the VH or VL as compared to a reference antibody, wherein the amino acid residue alteration: (a) was identified in a naturally occurring antibody having the same subtype as the reference antibody, and (b) is in a amino acid residue predicted to be buried. In some embodiments, the amino acid residue alteration in the naturally occurring antibody is due to somatic hypermutation. In some embodiments, the step of identifying a candidate binding polypeptide as having an increased expression level based on the amount of the labeled target molecule within the periplasm. In some embodiments, the method further comprises the step of identifying a candidate binding polypeptide as having increased stability based on the amount of the labeled target molecule within the periplasm.

In some embodiments of any of the preceding aspects, the method further comprises isolating the nucleic acid following the identifying step.

In some embodiments of any of the preceding aspects, the bacterium comprises a mutation affecting a transcription-regulating gene. In some embodiments, step (a) comprises providing a plurality of bacteria, wherein the plurality of bacteria comprise a library of nucleic acids, each encoding a mutant of the transcription-regulating gene. In some embodiments, the transcription-regulating gene is selected from a transcription initiation factor, an anti-sigma factor, an RNA polymerase subunit, or a transcription factor. In some embodiments, the transcription initiation factor is a sigma factor. In some embodiments, the sigma factor is selected from the group consisting of RpoD ($\sigma^{70}$), RpoE ($\sigma^{24}$), RpoH ($\sigma^{32}$), RpoS ($\sigma^{38}$), RpoN ($\sigma^{54}$), RpoF ($\sigma^{28}$), and FecI ($\sigma^{19}$). In some embodiments, the sigma factor is RpoD ($\sigma^{70}$). In some embodiments, the mutation affecting the transcription-regulating gene is present on a synthetic plasmid. In some embodiments, the mutation affecting the transcription-regulating gene is present in the endogenous bacterial genome. In some embodiments, the mutation affecting the transcription-regulating gene is due to error-prone PCR mutagenesis, chemical mutagenesis, transpositional mutagenesis, or targeted mutagenesis. In some embodiments, the mutation affecting the transcription-regulating gene is due to error-prone PCR mutagenesis. In some embodiments, the method identifies a bacterium having improved expression of the binding polypeptide.

In another aspect, the invention features a bacterium comprising (i) a loss-of-function mutation in a gene encoding Lpp; and (ii) an expression construct encoding an antibody. In some embodiments, the antibody is a full-length antibody. In some embodiments, the antibody is an IgG antibody. In some embodiments, the antibody is a half-antibody. In some embodiments, the antibody is an antibody fragment. In some embodiments, the antibody fragment is selected from the group consisting of Fab, Fab'-SH, Fv, scFv, and (Fab')$_2$ fragments. In some embodiments, the bacterium is a gram-negative bacterium. In some embodiments, the gram-negative bacterium is an *E. coli* bacterium. In some embodiments, the antibody is expressed in soluble form in the periplasm of the bacterium. In some embodiments, the loss-of-function mutation is a point mutation, an insertion mutation, or a deletion mutation. In some embodiments, the loss-of-function mutation is a deletion mutation. In some embodiments, the expression construct comprises a promoter operably linked to a gene encoding the antibody. In some embodiments, the expression construct comprises a synthetic plasmid. In some embodiments, the bacterium further comprises a mutation affecting a transcription-regulating gene. In some embodiments, the transcription-regulating gene is selected from a transcription initiation factor, an anti-sigma factor, an RNA polymerase subunit, or a transcription factor. In some embodiments, the transcription initiation factor is a sigma factor. In some embodiments, the sigma factor is selected from the group consisting of RpoD ($\sigma^{70}$), RpoE ($\sigma^{24}$), RpoH ($\sigma^{32}$), RpoS ($\sigma^{38}$), RpoN ($\sigma^{54}$), RpoF ($\sigma^{28}$), and FecI ($\sigma^{19}$). In some embodiments, the sigma factor is RpoD ($\sigma^{70}$). In some embodiments, the mutation affecting the transcription-regulating gene is present on a synthetic plasmid. In some embodiments, the mutation affecting the transcription-regulating gene is present in the endogenous bacterial genome. In some embodiments, the mutation affecting the transcription-regulating gene is due to error-prone PCR mutagenesis, chemical mutagenesis, transpositional mutagenesis, or targeted mutagenesis. In some embodiments, the mutation affecting the transcription-regulating gene is due to error-prone PCR mutagenesis.

In another aspect, the invention features a bacterium comprising (i) a mutation that allows for diffusion of membrane-impermeant molecules across the outer membrane into the periplasm; (ii) an expression construct encoding a binding polypeptide; and (iii) a mutation affecting a transcription-regulating gene. In some embodiments, the transcription-regulating gene is selected from a transcription initiation factor, an anti-sigma factor, an RNA polymerase subunit, or a transcription factor. In some embodiments, the transcription initiation factor is a sigma factor. In some embodiments, the sigma factor is selected from the group consisting of RpoD ($\sigma^{70}$), RpoE ($\sigma^{24}$), RpoH ($\sigma^{32}$), RpoS ($\sigma^{38}$), RpoN ($\sigma^{54}$), RpoF ($\sigma^{28}$), and FecI ($\sigma^{9}$). In some embodiments, the sigma factor is RpoD ($\sigma^{70}$). In some embodiments, the mutation affecting the transcription-regulating gene is present on a synthetic plasmid. In some embodiments, the mutation affecting the transcription-regulating gene is present in the endogenous bacterial genome. In some embodiments, the mutation affecting the transcription-regulating gene is due to error-prone PCR mutagenesis, chemical mutagenesis, transpositional mutagenesis, or targeted mutagenesis. In some embodiments, the mutation affecting the transcription-regulating gene is due to error-prone PCR mutagenesis. In some embodiments, the binding polypeptide is an antibody. In some embodiments, the antibody is a full-length antibody. In some embodiments, the antibody is an IgG antibody. In some embodiments, the antibody is a half-antibody. In some embodiments, the antibody is an antibody fragment. In some embodiments, the antibody fragment is selected from the group consisting of Fab, Fab'-SH, Fv, scFv, and (Fab')$_2$ fragments. In some embodiments, the bacterium is a gram-negative bacterium. In some embodiments, the gram-negative bacterium is an *E. coli* bacterium. In some embodiments, the antibody is expressed in soluble form in the periplasm of the bacterium. In some embodiments, the mutation that allows for diffusion of membrane-impermeant molecules across the outer membrane into the periplasm is in a gene encoding an outer membrane protein or a protein that affects LPS composition. In some embodiments, the outer membrane protein is major outer membrane lipoprotein Lpp (Lpp), a porin, or TolC. In some embodiments, the outer membrane protein is Lpp. In some embodiments, the protein that affects LPS composition is selected from EnvA, RfaD, RfaE, RfaH, RfaRd, TolA, TolB, and TolD.

In another aspect, the invention features an isolated antibody that specifically binds to interleukin-13 (IL-13), wherein the antibody comprises (a) a light chain variable region comprising the amino acid sequence of SEQ ID NO: 1 and (b) a heavy chain variable region comprising an amino acid sequence having at least 95% identity to the amino acid sequence of SEQ ID NO: 5.

In another aspect, the invention features an isolated antibody that specifically binds to IL-13, wherein the antibody comprises (a) a heavy chain variable region comprising the amino acid sequence of SEQ ID NO: 2 and (b) a light chain variable region comprising an amino acid sequence having at least 95% identity to the amino acid sequence of SEQ ID NO: 6.

In another aspect, the invention features an isolated antibody that specifically binds to IL-13, wherein the antibody comprises (a) a heavy chain variable region comprising the amino acid sequence of SEQ ID NO: 3 and (b) a light chain variable region comprising an amino acid sequence having at least 95% identity to the amino acid sequence of SEQ ID NO: 6.

In another aspect, the invention features an isolated antibody that specifically binds to IL-13, wherein the antibody comprises (a) a heavy chain variable region comprising the amino acid sequence of SEQ ID NO: 4 and (b) a light chain variable region comprising an amino acid sequence having at least 95% identity to the amino acid sequence of SEQ ID NO: 6.

In another aspect, the invention features an isolated antibody that specifically binds to IL-13, wherein the antibody comprises a light chain variable region comprising the amino acid sequence of SEQ ID NO: 1 and a heavy chain variable region comprising the amino acid sequence of SEQ ID NO: 5.

In another aspect, the invention features an isolated antibody that specifically binds to IL-13, wherein the antibody comprises a light chain variable region comprising the amino acid sequence of SEQ ID NO: 1 and a heavy chain variable region comprising the amino acid sequence of SEQ ID NO: 4.

In another aspect, the invention features an isolated antibody that specifically binds to IL-13, wherein the antibody comprises a light chain variable region comprising the amino acid sequence of SEQ ID NO: 6 and a heavy chain variable region comprising the amino acid sequence of SEQ ID NO: 2.

In another aspect, the invention features an isolated antibody that specifically binds to IL-13, wherein the antibody comprises a light chain variable region comprising the amino acid sequence of SEQ ID NO: 6 and the heavy chain variable region comprising the amino acid sequence of SEQ ID NO: 3.

In another aspect, the invention features an isolated antibody that specifically binds to IL-13, wherein the antibody comprises a light chain variable region comprising the amino acid sequence of SEQ ID NO: 6 and a heavy chain variable region comprising the amino acid sequence of SEQ ID NO: 4.

In some embodiments of any of the preceding aspects, the antibody further comprises the following six HVRs: (a) an HVR-H1 comprising the amino acid sequence of AYSVN (SEQ ID NO: 7); (b) an HVR-H2 comprising the amino acid sequence of MIWGDGKIVYNSALKS (SEQ ID NO: 8); (c) an HVR-H3 comprising the amino acid sequence of DGYYPYAMDN (SEQ ID NO: 9); (d) an HVR-L1 comprising the amino acid sequence of RASKSVDSYGNSFMH (SEQ ID NO: 10); (e) an HVR-L2 comprising the amino acid sequence of LASNLES (SEQ ID NO: 11); and (f) an HVR-L3 comprising the amino acid sequence of QQNNEDPRT (SEQ ID NO: 12).

In some embodiments, any one of the preceding antibodies specifically binds human IL-13 with a $K_D$ of about 1 nM or lower. In some embodiments, antibody specifically binds human IL-13 with a $K_D$ between about 1 pM and about 50 pM. In some embodiments, the antibody specifically binds human IL-13 with a $K_D$ of between about 29 pM and about 40 pM.

In some embodiments, any one of the preceding antibodies is monoclonal, human, humanized, or chimeric. In some embodiments, the antibody is a full-length antibody. In some embodiments, the antibody is an IgG antibody. In some embodiments, the antibody is a half-antibody. In some embodiments, the antibody is an antibody fragment that binds IL-13. In some embodiments, the antibody fragment is selected from the group consisting of Fab, Fab'-SH, Fv, scFv, and (Fab')$_2$ fragments. In some embodiments, the antibody is a monospecific antibody. In some embodiments, the antibody is a multispecific antibody. In some embodiments, the multispecific antibody is a bispecific antibody.

In another aspect, the invention features an isolated nucleic acid encoding any of the antibodies described herein. In another aspect, the invention features a vector (e.g., an expression vector) comprising the isolated nucleic acid for expressing the antibody. In another aspect, the invention features host cells comprising the preceding nucleic acids and/or vectors. In some embodiments, the host cell is a mammalian cell. In some embodiments, the host cell is a prokaryotic cell. In some embodiments, the prokaryotic cell is an *E. coli* cell.

In another aspect, the invention features a method of producing any of the antibodies described herein, the method comprising culturing a host cell that comprises any of the preceding vectors (e.g., expression vectors) in a culture medium. In some embodiments, the method further comprises recovering the antibody from the host cell or the culture medium.

In another aspect, the invention features a composition comprising any one of the preceding antibodies. In some embodiments, the composition further comprises a pharmaceutically acceptable carrier, excipient, or diluent. In some embodiments, the composition is a pharmaceutical composition.

In some aspects, any one of the preceding antibodies can be used as a medicament.

In some aspects, any one of the preceding antibodies can be used in treating an IL-13-mediated disorder.

In another aspect, the invention features a method of treating a patient suffering from asthmatic symptoms comprising administering to the patient an effective amount of any one of the preceding antibodies to reduce the asthmatic symptoms.

In another aspect, the invention features a method for inhibiting IgE antibody production in a patient comprising administering to the patient an effective amount of any one of the preceding antibodies. In some embodiments, the inhibition of IgE antibody production is intended to treat bronchial asthma, allergic rhinitis, allergic dermatitis, bronchial asthma, allergic rhinitis, urticaria, anaphylaxis, or atopic dermatitis.

In another aspect, the invention features a method of treating an IL-13-mediated disorder in a patient, comprising administering to the patient an effective amount of any one of the preceding antibodies. In some embodiments, the disorder is allergic asthma, non-allergic (intrinsic) asthma, allergic rhinitis, atopic dermatitis, allergic conjunctivitis, eczema, urticaria, food allergies, chronic obstructive pulmonary disease, ulcerative colitis, RSV infection, uveitis, scleroderma, or osteoporosis.

In another aspect, the invention features a method of treating an IgE-mediated disorder in a patient, comprising administering to the patient an effective amount of any one of the preceding antibodies. In some embodiments, the IgE-mediated disorder is bronchial asthma, allergic rhinitis, allergic dermatitis, urticaria, anaphylaxis, or atopic dermatitis.

In some embodiments of the preceding methods of treating, the antibody inhibits binding of IL-13 to its receptor and inhibits one or more functions associated with binding of IL-13 to its receptor.

In some embodiments of the preceding methods of treating, the antibody is administered by one or more of the routes selected from the group consisting of intravenous, intraperitoneal, inhalation, intramuscular, subcutaneous, and oral. In some embodiments, the route is subcutaneous.

In some embodiments of the preceding methods of treating, the patient is human.

In another aspect, the invention features a library comprising a plurality of nucleic acids encoding candidate antibody variants, wherein each candidate binding polypeptide variant comprises an amino acid residue alteration in an FR of the VH or VL as compared to a reference antibody, wherein the amino acid residue alteration: (a) was identified in a naturally occurring antibody having the same subtype as the reference antibody; and (b) is in an amino acid residue predicted to be buried. In some embodiments, the amino acid residue alteration in the naturally occurring antibody is due to somatic hypermutation.

BRIEF DESCRIPTION OF THE DRAWINGS

The application file contains at least one drawing executed in color. Copies of this patent or patent application with color drawings will be provided by the Office upon request and payment of the necessary fee.

FIG. 3C is a series of graphs showing enrichment of best-expressing variants from a pool of anti-VEGF.2 WT and three variants by BAD. The flow cytometry signal of the pool shifts in a more positive direction over two rounds by sorting for the top 1% VEGF-binding cells. The lowest-expressing anti-VEGF.2 WT and the best-expressing variant S24R.E6Q.M34I were analyzed in each round and are shown for comparison.

FIG. 3D is a series of pie charts showing anti-VEGF.2 variant enrichment over two rounds of sorting. 96 clones were sequenced, and the highest-expressing anti-VEGF.2 variants, F71Y.E6Q.M34I and S24R.E6Q.M34I, are enriched after two rounds, while the two lowest-expressing variants (anti-VEGF.2 WT and L4M.E6Q.M34I) are depleted.

FIG. 6 shows amino acid sequences of the light chain and heavy chain anti-IL-13 variable domains from an anti-IL-13 antibody. An antibody variable domain is composed of three hypervariable regions (HVR; overlined) that are nestled between four framework regions (FR). Somatic hypermutation can introduce changes into both the FR and HVR. Collating data from the Kabat database, all the amino acid changes that occur by somatic hypermutation within the framework of the Variable Kappa 4 ($V_K4$) and Heavy 2 ($V_H2$) subtypes were compiled, which were then narrowed to the non-solvent exposed residues (indicated by amino acid residues positioned beneath the sequences of SEQ ID NO: 5 and SEQ ID NO: 6). Single framework variants of anti-IL-13 half-antibody, 5 in light chain and 28 in heavy chain, were made and combined to screen by BAD.

DETAILED DESCRIPTION OF EMBODIMENTS OF THE INVENTION

I. Definitions

Figure 1A:
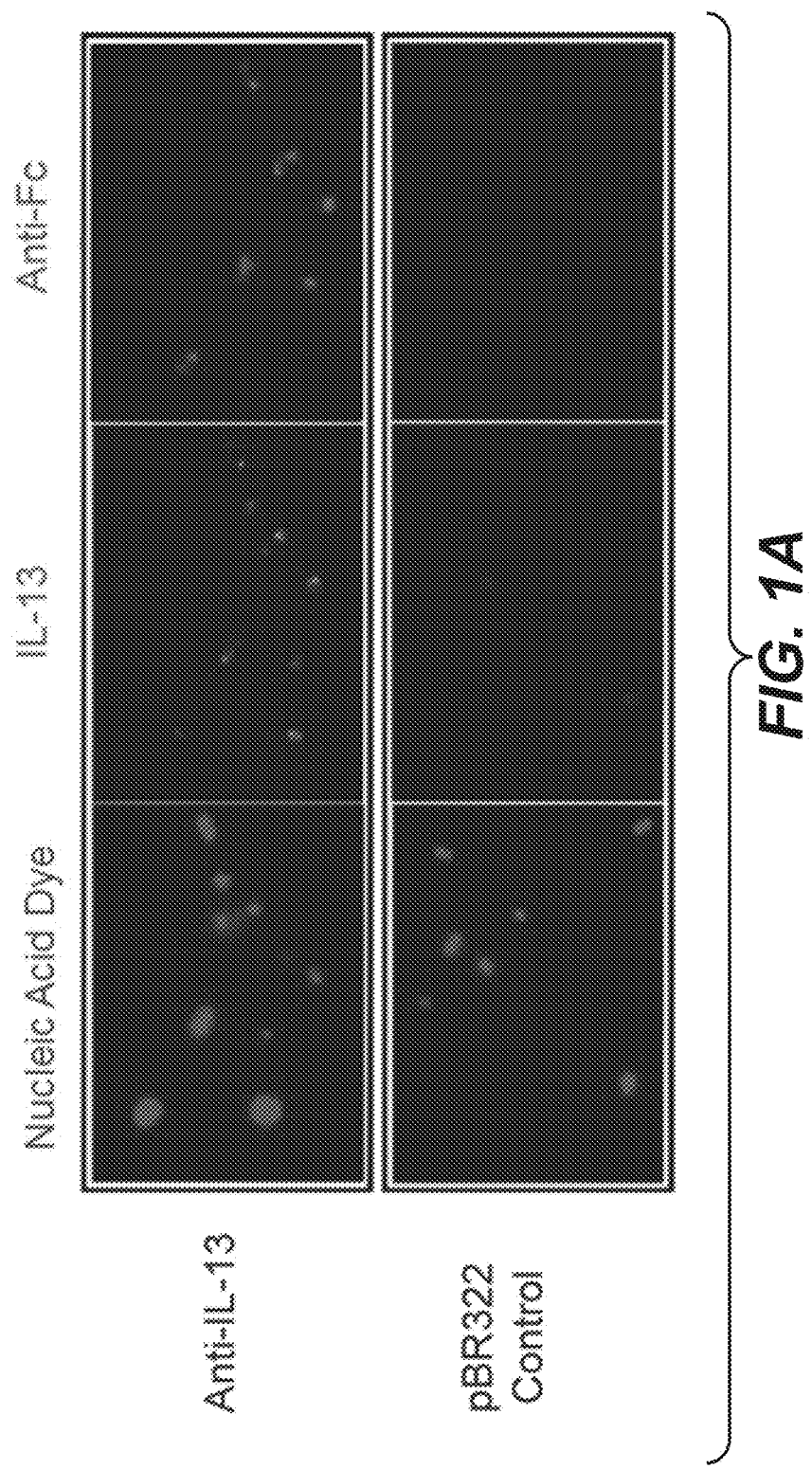
FIG. 1A is a panel of fluorescent micrographs showing specific staining of antibody-expressing bacterial cells with IL-13 antigen. Cells expressing an anti-IL-13 antibody or an empty vector control (pBR322) were stained with SYTO® 41 (nucleic acid dye), ALEXA FLUOR® 488-labeled IL-13, or DYLIGHT® 649-labeled anti-human Fc F(ab')$_2$ antibodies. Only cells expressing the antibody stain positive with IL-13 antigen and the anti-human Fc antibody.

The term "about" as used herein refers to the usual error range for the respective value readily known to the skilled person in this technical field. Reference to "about" a value or parameter herein includes (and describes) embodiments that are directed to that value or parameter per se.

A "bacterium" as used herein refers to a bacterial cell that includes an inner membrane (i.e., cytoplasmic membrane), a periplasm, and an outer membrane. The outer membrane is distinct from the inner membrane and may comprise, for example, lipopolysaccharide (LPS) and porins. In some embodiments, a bacterium is a gram-negative bacterium. Exemplary bacterial species include *Escherichia* species (e.g., *E. coli*), *Salmonella* species (e.g., *S. typhimurium* and *S. enterica*), and others known in the art.

The term "binding polypeptide" refers to a polypeptide that specifically binds a target molecule. In some embodiments, a binding polypeptide is an antibody. In other embodiments, a binding polypeptide is, for example, an antibody mimetic, a cell surface receptor, a cytokine, or a growth factor. The term "target molecule" refers to a specific binding target of a binding polypeptide. A target molecule is typically a small molecule, polypeptide, or polypeptide fragment. The target molecule can be, for example, an antigen if the binding polypeptide is an antibody.

With regard to the binding of a binding polypeptide (e.g., an antibody) to a target molecule, the term "specific binding" or "specifically binds" or is "specific for" a particular polypeptide or an epitope on a particular target molecule means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-8}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

As used herein, "library" refers to a plurality of binding polypeptides (e.g., antibody or antibody fragment) sequences, or the nucleic acids that encode these sequences. Exemplary libraries may have a size of between about 2 binding polypeptides to about $10^{14}$ binding polypeptides (e.g., about 2 to about 10, about 2 to about 20, about 2 to about 30, about 2 to about 40, about 2 to about 50, about 2 to about 60, about 2 to about 70, about 2 to about 70, about 2 to about 80, about 2 to about 100, about 2 to about $10^{14}$, about 2 to about $10^{13}$, about 2 to about $10^{12}$, about 2 to about $10^{11}$, about 2 to about $10^{10}$, about 2 to about $10^9$, about 2 to about $10^8$, about 20 to about $10^8$, about 30 to about $10^8$, about 40 to about $10^8$, about 50 to about $10^8$, about 60 to about $10^8$, about 70 to about $10^8$, about 80 to about $10^8$, about 90 to about $10^8$, about 100 to about $10^8$, about 200 to about $10^8$ binding, about 400 to about $10^8$, about 600 to about $10^8$, about 800 to about $10^8$, about $10^3$ to about $10^8$, about $10^4$ to about $10^8$, about $10^5$ to about $10^8$, about $10^6$ to about $10^8$, or about $10^7$ to about $10^8$ binding polypeptides).

A "variant" or "mutant" of a starting or reference binding polypeptide (e.g., a reference antibody), is a binding polypeptide that (1) has an amino acid sequence different from that of the starting or reference polypeptide and (2) was derived from the starting or reference polypeptide through either natural or artificial (man-made) mutagenesis. Such variants include, for example, deletions from, insertions into, and/or substitutions of, residues within the amino acid sequence of the binding polypeptide of interest, referred to herein as "amino acid residue alterations." Thus, a variant HVR refers to a HVR comprising a variant sequence with respect to a starting or reference polypeptide sequence (such as that of a source antibody or antigen-binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics (e.g., affinity, stability, and/or expression).

A "wild-type" or "reference" sequence or the sequence of a "wild-type" or "reference" protein/polypeptide, such as an HVR, FR, or variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

A "mutation" is a deletion, insertion, or substitution of a nucleotide(s) relative to a reference nucleotide sequence, such as a wild-type sequence.

The term "membrane-impermeant" refers to the inability of a molecule (e.g., a polypeptide) to diffuse across a biological membrane (e.g., the inner and/or outer membrane of a bacterium) or channel pore (e.g., a porin). In contrast, a "membrane-permeant" molecule is able to diffuse across a biological membrane. It is to be understood that under some conditions, for example, through methods of the invention, molecules that are normally membrane-impermeant (e.g., polypeptides) can diffuse into the periplasm of a bacterium, for example, if the integrity of the outer membrane is permanently or transiently compromised.

The term "permeability" as used herein refers to the rate of diffusion of a molecule across a biological membrane. A biological membrane is "permeable" to a given molecule if the molecule is substantially able to diffuse across the membrane. A biological membrane is "impermeable" to a given molecule if the molecule is not substantially able to diffuse across the membrane. The charge, polarity, and size of a molecule can affect whether a biological membrane is permeable or impermeable to the molecule. Typically, hydrophobic molecules and small uncharged polar molecules are permeant across a biological membrane, whereas most water-soluble (hydrophilic) molecules are impermeant. The outer membrane of a bacterium is typically impermeable to diffusion of hydrophilic molecules having a molecular weight of greater than about 600 daltons (see, e.g., Decad et al. J. Bacteriology 128(1): 325-336, 1976).

As used herein, "major outer membrane lipoprotein Lpp," also referred to in the art as "Lpp," "Braun lipoprotein," and "murein lipoprotein," refers to any native Lpp from any bacterial source, including *E. coli* or *S. typhimurium* (also known as IkyD), unless otherwise indicated. The term encompasses "full-length," unprocessed Lpp, as well as any form of Lpp that results from processing in the cell. Lpp interacts with peptidoglycan and contributes to the maintenance of the structural and functional integrity of the cell envelope. The amino acid sequence of an exemplary *E. coli* (strain K12) Lpp can be found, for example, under UniProtKB accession number P69776.

A "periplasm" is a space bordered by two selectively permeable barriers (e.g., biological membranes). In many species of bacteria, including *Escherichia coli*, the periplasm is the space bordered by the inner membrane and the outer membrane.

A "permeabilization agent" as used herein refers to a chemical that is capable of increasing the permeability of the bacterial outer membrane, for example, to a molecule that is typically membrane-impermeant (e.g., a polypeptide). Exemplary permeabilization agents include, for example, chelators, including divalent cation chelators (e.g., ethylenediaminetetraacetic acid (EDTA; also referred to as edetic acid or 2-[2-[bis(carboxymethyl)amino]ethyl-(carboxymethyl)amino]acetic acid), 2-[2-[2-[2-[bis(carboxymethyl) amino]phenoxy]ethoxy]-N-(carboxymethyl)anilino]acetic acid (BAPTA), and 2-[2-[2-[2-[bis(carboxymethyl)amino] ethoxy]ethoxy]ethyl-(carboxymethyl)amino]acetic acid (EGTA)), NaCl (Chen et al. *Nat. Biotech.* 19: 537-542, 2001), sucrose, antibiotics (e.g., aminoglycosides (e.g., streptomycin and gentamicin), polymyxin B, deacylated polymyxin, octapeptin, and benzyl penicillin), detergents, lysozyme, Tris, Tris-EDTA, ascorbate, polylysine, benzalkonium chloride, protamine, bactericidal/permeability-increasing protein (BPI), serum and/or complement, $Ca^{2+}$, or combinations thereof. See, for example, Hancock, *Ann. Rev. Microbiol.* 38: 237-264, 1984. In some embodiments, the permeabilization agent is EDTA.

"Permeabilize" as used herein means to increase the rate of diffusion of a molecule across a biological membrane, for example, the rate of diffusion of a molecule that is typically membrane-impermeant (e.g., a polypeptide) across a bacterial outer membrane.

"Polypeptide" refers to a peptide or protein containing two or more amino acids linked by peptide bonds, and includes peptides, oligomers, proteins, and the like. Polypeptides can contain natural, modified, or synthetic amino acids. Polypeptides can also be modified naturally, such as by post-translational processing, or chemically, such as amidation acylation, cross-linking, and the like.

A "plurality" of a substance, such as a polypeptide or polynucleotide of the invention, as used herein, generally refers to a collection of two or more types or kinds of the substance. There are two or more types or kinds of a substance if two or more of the substances differ from each other with respect to a particular characteristic, such as a variant amino acid found at a particular amino acid position. For example, there is a plurality of polypeptides of the invention if there are two or more polypeptides of the invention that are substantially the same, preferably identical, in sequence except for the sequence of a variant framework region (FR) or except for a variant amino acid at a particular non-solvent exposed amino acid position. In another example, there is a plurality of polynucleotides of the invention if there are two or more polynucleotides of the invention that are substantially the same, preferably identical, in sequence except for the sequence that encodes a variant FR or except for the sequence that encodes a variant amino acid for a particular non-solvent exposed amino acid position.

The term "reseal" as used herein refers to substantially restoring the membrane permeability barrier of a bacterial outer membrane. In some embodiments, resealing reverses a prior permeabilization of a bacterial outer membrane.

The term "transcription-regulating gene," as used herein, refers to any gene that affects transcription or other aspects of expression (e.g., translation, trafficking, or stability) of a gene encoding a binding polypeptide (e.g., an antibody), for example, globally (e.g., affecting transcription of a multitude of genes) or individually (e.g., affecting transcription of one or a few genes). Exemplary, non-limiting transcription-regulating genes include transcription initiation factors (e.g., sigma factors), anti-sigma factors, RNA polymerase subunits, and transcription factors. In some embodiments, the sigma factor is selected from the group consisting of RpoD ($\sigma^{70}$), RpoE ($\sigma^{24}$), RpoH ($\sigma^{32}$), RpoS ($\sigma^{38}$), RpoN ($\sigma^{54}$), RpoF ($\sigma^{23}$), and FecI ($\sigma^{19}$). In some embodiments, the sigma factor is RpoD ($\sigma^{70}$).

A "mutation affecting a transcription-regulating gene" refers to any mutation that affects the function, expression level, stability, or activity of a transcription-regulating gene. The mutation may be, for example, located in the transcription-regulating gene itself. In other embodiments, the mutation may reside in a regulatory nucleic acid sequence, e.g., a promoter or enhancer of the transcription-regulating gene. The mutation may be of any type known in the art, e.g., a point mutation, an insertion mutation, a deletion mutation, a frame-shift mutation, and the like.

An "expression construct" refers to any nucleic acid element capable of conferring expression of a gene (e.g., a binding polypeptide (e.g., an antibody) or a transcription-regulating gene) in bacteria. An expression construct may refer to a synthetic plasmid transformed into a bacterium, a synthetic nucleic acid sequence integrated into an endogenous bacterial genome, or any other suitable nucleic acid element. In some embodiments, and expression construct is a synthetic plasmid.

As used herein, the terms "improved" and "increased," with respect to expression and/or stability of a binding polypeptide, refer to an increase or enhancement relative to a reference expression level of the binding polypeptide and/or a reference stability of the binding polypeptide. In some embodiments, the reference expression level may be the expression level of a wild-type binding polypeptide. In other embodiments, the reference expression level may be the expression level of a variant binding polypeptide. In some embodiments, the reference expression level may be the expression level of the binding polypeptide in a wild-type bacterium. In some embodiments, the reference expression level may be the expression level of the binding polypeptide in a mutant bacterium. In some embodiments, the reference stability may be the stability of a wild-type binding polypeptide. In other embodiments, the reference stability may be the stability of a variant binding polypeptide.

A "synthetic plasmid" refers to any non-naturally occurring plasmid (e.g., a linear plasmid or circular plasmid) that may be used for purposes of gene expression, e.g., expression of a gene encoding a binding polypeptide or a transcription-regulating gene. A synthetic plasmid may include, for example, a promoter operably linked to the gene of interest, antibiotic resistance markers, multiple cloning sites, origin(s) of replication, or any other element known in the art.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity-matured" antibody is one with one or more alterations in one or more HVRs and/or framework regions which result in an improvement in the affinity of the antibody for antigen, compared to a parent antibody which does not possess those alteration(s). Preferred affinity-matured antibodies will have nanomolar or even picomolar affinities for the target antigen. Affinity-matured antibodies are produced by procedures known in the art. For example, Marks et al. *Bio/Technology* 10:779-783, 1992 describes affinity maturation by VH and VL domain shuffling. Random mutagenesis of HVR and/or framework residues is described by: Barbas et al. *Proc. Natl. Acad. Sci. USA* 91:3809-3813, 1994; Schier et al. *Gene* 169:147-155, 1995; Yelton et al. *J. Immunol.* 155:1994-2004, 1995; Jackson et al. *J. Immunol.* 154(7):3310-3319, 1995; and Hawkins et al. *J. Mol. Biol.* 226:889-896, 1992.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al. *Protein Eng.* 8(10):1057-1062, 1995); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light (L) chain along with the VH domain of the heavy (H) chain, and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having an additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest*, 5th Ed. Public Health Service, National Institutes of Health, Bethesda, Md., 1991.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three Hs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315, 1994.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al. *Proc. Natl. Acad. Sci. USA* 90:6444-6448, 1993.

A "blocking" antibody or an "antagonist" antibody is one which inhibits or reduces biological activity of the antigen it binds. Certain blocking antibodies or antagonist antibodies substantially or completely inhibit the biological activity of the antigen.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch et al. *Annu. Rev. Immunol.* 9:457-492, 1991. To assess ADCC activity of a molecule of interest, an in vitro ADCC assay, such as that described in U.S. Pat. Nos. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. *Proc. Natl. Acad. Sci. USA* 95:652-656, 1998.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234, 1997). FcRs are reviewed, for example, in Ravetch et al. *Annu. Rev. Immunol.* 9:457-492, 1991; Capel et al. *Immunomethods* 4:25-34, 1994; and de Haas et al. *J. Lab. Clin. Med.* 126:330-41, 1995. Other FcRs, including those to be identified in the future, are encompassed by the term "FcR" herein. The term also includes the neonatal receptor, FcRn, which is responsible for the transfer of maternal IgGs to the fetus (see, e.g., Guyer et al. *J. Immunol.* 117:587, 1976; and Kim et al. *J. Immunol.* 24:249, 1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al. *J. Immunol. Methods* 202:163, 1996, can be performed.

An "epitope" is the portion of the antigen to which the antibody specifically binds. For a polypeptide antigen, the epitope is generally a peptide portion of about 4-15 amino acid residues.

The terms "full-length antibody," "intact antibody," and "whole antibody" are used herein interchangeably to refer to an antibody having a structure substantially similar to a native antibody structure or having heavy chains that contain an Fc region as defined herein.

The term "half-antibody" as used herein refers to one immunoglobulin heavy chain associated with one immunoglobulin light chain. One skilled in the art will readily appreciate that a half-antibody may encompass a fragment thereof and may also have an antigen-binding domain consisting of a single variable domain, e.g., originating from a camelidae.

A "human antibody" is one which possesses an amino acid sequence which corresponds to that of an antibody produced by a human and/or has been made using any of the techniques for making human antibodies. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup (also referred to herein as a "subtype") of variable domain sequences. Generally, the subgroup of sequences is a subgroup as in Kabat et al. *Sequences of Proteins of Immunological Interest*, Fifth Edition, NIH Publication 91-3242, Bethesda Md., vols. 1-3, 1991. In one embodiment, for the VL, the subgroup is subgroup kappa III or kappa IV as in Kabat et al. supra. In one embodiment, for the VH, the subgroup is subgroup III as in Kabat et al. supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522-525, 1986; Riechmann et al. *Nature* 332:323-329, 1988; and Presta, *Curr. Op. Struct. Biol.* 2:593-596, 1992.

An "immunoconjugate" is an antibody conjugated to one or more heterologous molecule(s), including but not limited to a cytotoxic agent.

The term "isolated" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., sodium dodecyl sulfate polyacrylamide gel electrophoresis (SDS-PAGE), isoelectric focusing (IEF), capillary electrophoresis) or chromatographic (e.g., ion exchange or reverse phase HPLC) methods. For a review of methods for assessment of antibody purity, see, for example, Flatman et al. *J. Chromatogr. B* 848:79-87, 2007. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VHVL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

A "naked antibody" refers to an antibody that is not conjugated to a heterologous moiety (e.g., a cytotoxic moiety) or radiolabel. The naked antibody may be present in a pharmaceutical composition.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from e.g., around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al. supra) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia et al. *J. Mol. Biol.* 196:901-917, 1987. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al. supra). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "variable domain residue numbering as in Kabat" or "amino acid position numbering as in Kabat," and variations thereof, refers to the numbering system used for heavy chain variable domains or light chain variable domains of the compilation of antibodies in Kabat et al. supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al. supra). The "EU numbering system" or "EU index" is generally used when referring to a residue in an immunoglobulin heavy chain constant region (e.g., the EU index reported in Kabat et al. supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

As used herein, "interleukin-13 (IL-13)" refers to any native IL-13 from any vertebrate source, including mammals such as primates (e.g., humans) and rodents (e.g., mice and rats), unless otherwise indicated. IL-13 is a cytokine secreted by many cell types, including T helper type 2 (Th2) cells. The term encompasses "full-length," unprocessed IL-13, as well as any form of IL-13 that results from processing in the cell. The amino acid sequence of an exemplary human IL-13 can be found, for example, under UniProtKB accession number P35225. IL-13 binds to the IL-13 receptor, which can include IL-4 receptor alpha (IL4Rα) in complex with IL-13 receptor subunit alpha1 (IL13RA1) or IL-13 receptor subunit alpha2 (IL13RA2). For instance, IL-13 can bind to a complex of IL-4 receptor alpha and IL-13 receptor subunit alpha1.

The terms "anti-IL-13 antibody," an "antibody that binds to IL-13," and "antibody that specifically binds IL-13" refer to an antibody that is capable of binding IL-13 with sufficient affinity such that the antibody is useful as a diagnostic and/or therapeutic agent in targeting IL-13. In one embodiment, the extent of binding of an anti-IL-13 antibody to an unrelated, non-IL-13 protein is less than about 10% of the binding of the antibody to IL-13 as measured, e.g., by a radioimmunoassay (RIA). In certain embodiments, an antibody that binds to IL-13 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-IL-13 antibody binds to an epitope of IL-13 that is conserved among IL-13 from different species. Exemplary anti-IL-13 antibodies include, but are not limited to, lebrikizumab, 228B/C-1, 228A-4, 227-26, and 227-43 (see, for example, U.S. Pat. Nos. 7,674,459; 8,067,199: 8,088,618: 8,318,160: and 8,734,797, the entirety of which are incorporated herein by reference).

The term "vascular endothelial growth factor" or "VEGF" as used herein refers to the 165-amino acid human vascular endothelial cell growth factor and related 121-, 189-, and 206-amino acid human vascular endothelial cell growth factors, as described by Leung et al. *Science* 246: 1306, 1989, and Houck et al. *Mol. Endocrin.* 5: 1806, 1991, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, e.g., by a radioimmunoassay (RIA). In certain embodiments, an antibody that binds to VEGF has a dissociation constant (Kd) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-VEGF antibody binds to an epitope of VEGF that is conserved among VEGF from different species.

Non-limiting examples of anti-VEGF antibodies include, for example and without limitation, the anti-VEGF antibody "bevacizumab (BV or Bev)," also known as "rhuMAb VEGF," or "AVASTIN®", which is a recombinant humanized anti-VEGF monoclonal antibody generated according to Presta et al., *Cancer Res.* 57:4593-4599 (1997). Bevacizumab comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated. Other exemplary anti-VEGF antibodies include, for example, the antibodies described in U.S. Pat. No. 6,884,879 and WO 2005/044853. A further example includes the anti-VEGF antibody ranibizumab (LUCENTIS® antibody or rhuFab V2), which is a humanized, affinity-matured anti-human VEGF Fab fragment. Ranibizumab is produced by standard recombinant technology methods in *E. coli* expression vector and bacterial fermentation. Ranibizumab is not glycosylated and has a molecular mass of ~48,000 daltons. See WO 1998/45331 and US 2003/0190317.

As used herein, "administering" is meant a method of giving a dosage of a compound (e.g., an antibody of the invention or a nucleic acid encoding an antibody of the invention) or a composition (e.g., a pharmaceutical composition, e.g., a pharmaceutical composition including an antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intravitreally, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

"Angiogenesis" refers to the process through which new blood vessels form from pre-existing blood vessels. Angiogenesis is distinct from vasculogenesis, which is the de novo formation of endothelial cells from mesoderm cell precursors. Disorders associated with pathological angiogenesis can be treated by compositions and methods of the invention. These disorders include both non-neoplastic disorders and cell proliferative disorders. Cell proliferative disorders include but are not limited those described below. Non-neoplastic disorders include but are not limited to ocular conditions (non-limiting ocular conditions include, for example, retinopathy including proliferative diabetic retinopathy, choroidal neovascularization (CNV), age-related macular degeneration (AMD), diabetic and other ischemia-related retinopathies, diabetic macular edema (DME), pathologic myopia, von Hippel-Lindau disease, histoplasmosis of the eye, retinal vein occlusion (including central (CRVO) and branched (BRVO) forms), corneal neovascularization, retinal neovascularization, retinopathy of prematurity (ROP), familial exudative vitreoretinopathy (FEVR), Coats' disease, Norrie Disease, Osteoporosis-Pseudoglioma Syndrome (OPPG), subconjunctival hemorrhage, and hypertensive retinopathy), undesired or aberrant hypertrophy, arthritis, rheumatoid arthritis (RA), psoriasis, psoriatic plaques, sarcoidosis, atherosclerosis, atherosclerotic plaques, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/ trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or to the VEGF-A receptor (e.g., KDR receptor or Flt-1 receptor), anti-PDGFR inhibitors such as GLEEVEC™ (imatinib mesylate). Anti-angiogenesis agents also include native angiogenesis inhibitors, e.g., angiostatin, endostatin, etc. See, e.g., Klagsbrun and D'Amore, *Annu. Rev. Physiol.*, 53:217-39 (1991); Streit and Detmar, *Oncogene*, 22:3172-3179 (2003) (e.g., Table 3 listing anti-angiogenic therapy in malignant melanoma); Ferrara & Alitalo, *Nature Medicine* 5(12):1359-1364 (1999); Tonini et al., *Oncogene*, 22:6549-6556 (2003) (e.g., Table 2 listing known anti-angiogenic factors); and, Sato *Int. J. Clin. Oncol.*, 8:200-206 (2003) (e.g., Table 1 lists anti-angiogenic agents used in clinical trials).

"Asthma" refers to a chronic pulmonary disease that can involve airway inflammation, hyperresponsiveness and obstruction. Physiologically, airway hyperresponsiveness is documented by decreased bronchial airflow after bronchoprovocation with methacholine or histamine. Bronchial provocation with allergen induces a prompt early phase immunoglobulin E (IgE)-mediated decrease in bronchial airflow followed in many patients by a late-phase IgE-mediated reaction with a decrease in bronchial airflow for 4-8 hours. The early response is caused by acute release of inflammatory substances, such as histamine, PGD2, leukotriene, tryptase and platelet activating factor (PAF), whereas the late response is caused by de novo synthesized pro-inflammatory cytokines (e.g. TNFα, IL-4, IL-13) and chemokines (e.g. MCP-1 and MIP-1α) (Busse et al. *Allergy: Principles and Practice*, Ed. Middleston, 1173, 1998). In chronic asthmatic patients, persistent pulmonary symptoms are mediated by the heightened response of Th2 cells. Th2 cytokines are believed to play a vital role in the disease (Larche et al. *J. Allergy Clin. Immunol.* 111: 450, 2003), in particular, IL-13 and IL-4 produced by Th2 cells with NK phenotype (NKT) in the airway as indicated in a model of asthma in rodents (Akbari et al. *Nature Med.*, 9: 582, 2003). The gross pathology of asthmatic airways displays lung hyperinflation, smooth muscle hypertrophy, lamina reticularis thickening, mucosal edema, epithelial cell sloughing, cilia cell disruption, and mucus gland hypersecretion. Microscopically, asthma is characterized by the presence of increased numbers of eosinophils, neutrophils, lymphocytes, and plasma cells in the bronchial tissues, bronchial secretions, and mucus. Initially, there is recruitment of leukocytes from the bloodstream to the airway by activated CD4+ T-lymphocytes. The activated T-lymphocytes also direct the release of inflammatory mediators from eosinophils, mast cells, and lymphocytes. In addition, the Th2 cells produce IL-4, IL-5, IL-9 and IL-13. IL-4, in conjunction with IL-13, signals the switch from IgM to IgE antibodies.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include, but are not limited to, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, melanoma, superficial spreading melanoma, lentigo maligna melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lyrnphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic rnyeloblastic leukemia; and post-transplant lymphoproliferative disorder (PTLD), as well as abnormal vascular proliferation associated with phakomatoses, edema (such as that associated with brain tumors), and Meigs' syndrome.

The terms "cell proliferative disorder" and "proliferative disorder" refer to disorders that are associated with some degree of abnormal cell proliferation. In one embodiment, the cell proliferative disorder is cancer.

The terms "cancer", "cancerous", "cell proliferative disorder", "proliferative disorder" and "tumor" are not mutually exclusive as referred to herein.

"Tumor", as used herein, refers to all neoplastic cell growth and proliferation, whether malignant or benign, and all pre-cancerous and cancerous cells and tissues.

A "disorder" is any condition that would benefit from treatment, for example, with a therapeutic antibody. In some embodiments, a disorder may be an IL-13-mediated disorder or an IgE-mediated disorder. In other embodiments, a disorder may involve abnormal or pathological angiogenesis (e.g., excessive, inappropriate, or uncontrolled angiogenesis) or vascular permeability. A disorder can be chronic or acute.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramicle and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al. *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan: vindesine (ELDISINE®, FILDESIN®); dacarbazine: mannomustine: mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (TARCEVA™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafamib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: antiestrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgensiretinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

An "effective amount" of an agent, e.g., a pharmaceutical formulation, refers to an amount effective, at dosages and for periods of time necessary, to achieve the desired therapeutic or prophylactic result.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tarnoxifen, prednisone, dacarbazine, rnechlorethamine, cisplatin, methotrexate, 5-fluorouracil, and ara-C. Further information can be found in Mendelsohn et al. eds., *The Molecular Basis of Cancer*, Chapter 1, entitled "Cell cycle regulation, oncogenes, and antineoplastic drugs" by Murakami et al. (W. B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "IL-13-mediated disorder," as used herein, refers to any disorder or condition mediated by, or associated with, IL-13. In some embodiments, IL-13-mediated disorders are associated with excess IL-13 levels or activity in which atypical symptoms may manifest due to the levels or activity of IL-13 locally and/or systemically in the body. IL-13-mediated disorders include, for example, allergy, asthma (including allergic asthma, atopic asthma, severe asthma, and non-allergic (intrinsic) asthma), autoimmune disease (e.g., psoriasis, rheumatoid arthritis, juvenile chronic arthritis, inflammatory bowel disease (e.g., ulcerative colitis and Crohn's disease), or other inflammatory disease. For example, IL-13 mediated disorders include: allergic rhinitis (e.g., seasonal allergic rhinitis), atopic dermatitis, allergic conjunctivitis, eczema, urticaria, food allergies, food hypersensitivity, celiac disease, immune-mediated skin diseases (including, e.g., bullous skin diseases, erythema multiform, contact dermatitis), fibrosis, hepatic fibrosis, endomyocardial fibrosis, chronic bronchitis, bronchiectasis, idiopathic interstitial pneumonia, goblet cell metaplasia, lung inflammatory disorders, inflammatory and fibrotic lung diseases (including, e.g., cystic fibrosis, idiopathic pulmonary fibrosis, and chronic obstructive pulmonary disease (COPD)), gluten-sensitive enteropathy, Whipple's disease, immunologic diseases of the lung (including, e.g., eosinophilic pneumonia (e.g., chronic eosinophilic pneumonia), idiopathic pulmonary fibrosis, allergic bronchopulmonary aspergillosis, and hypersensitivity pneumonitis), Churg-Strauss syndrome (periarteritis nodosa plus atopy), eosinophilic myalgia syndrome, hypereosinophilic syndrome, edematous reactions (including, e.g., episodic angiodema, eosinophilic esophagitis, eosinophilic gastritis, eosinophilic gastroenteritis, eosinophilic enteritis and eosinophilic colitis), nasal micropolyposis and polyposis, RSV infection, uveitis, scleroderma, osteoporosis, and malignancies, including cancers or tumors associated with aberrant expression of IL-13 (including, e.g., Hodgkin's lymphoma).

The term "IgE-mediated disorder," as used herein, refers to any disorder or condition mediated by, or associated with, IgE. Exemplary IgE-mediated disorders include bronchial asthma, allergic rhinitis, allergic dermatitis, urticaria, anaphylaxis, or atopic dermatitis.

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachrornosornally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site, Eukaryotic cells are known to utilize promoters, polyadenylation signals, and enhancers.

The terms "level of expression" or "expression level" are used interchangeably and generally refer to the amount of a polynucleotide or an amino acid product or protein in a biological sample. "Expression" generally refers to the process by which gene-encoded information is converted into the structures present and operating in the cell. Therefore, according to the invention "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis, "Expressed genes" include those that are transcribed into a polynucleotide as mRNA and then translated into a protein, and also those that are transcribed into RNA but not translated into a protein (for example, transfer and ribosomal RNAs).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech. Inc. and the source code has been filed with user documentation in the U.S. Copyright Office, Washington D.C., 20559, where it is registered under U.S. Copyright Registration No. TXU510087. The ALIGN-2 program is publicly available through Genentech. Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The amino acid sequences described herein are contiguous amino acid sequences unless otherwise specified.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al. "Prodrugs: A Chemical Approach to Targeted Drug Delivery," *Directed Drug Delivery*, Borchardt et al. (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetarnide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor.

A "patient," "subject," or "individual" is a vertebrate, preferably a mammal, more preferably a human. Mammals include, but are not limited to, farm animals (such as cows, and sheep), sport animals, pets (such as cats, dogs and horses), primates (e.g., humans and non-human primates such as monkeys), and rodents (e.g., mice and rats).

The term "therapeutically effective amount" refers to an amount of an antibody or antibody fragment to treat a disease or disorder in a subject. In the case of an IL-13-mediated disorder, the therapeutically effective amount of the antibody or antibody fragment (e.g., an anti-IL-13 antibody) may ameliorate or treat the disease, or prevent, reduce, ameliorate, or treat symptoms associated with the disease. In the case of a disorder associated with pathological angiogenesis, the therapeutically effective amount of the antibody or antibody fragment (e.g., an anti-VEGF antibody) may ameliorate or treat the disease, or prevent, reduce, ameliorate, or treat symptoms associated with the disease. In the case of a proliferative disease (e.g., a solid tumor), the therapeutically effective amount of the antibody or antibody fragment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), duration of disease free survival (DFS), duration of progression free survival (PFS), the response rates (RR), duration of response, and/or quality of life.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

II. Methods and Compositions

In one aspect, the invention is based, in part, on novel methods of identifying bacteria comprising binding polypeptides, e.g., methods of screening for bacteria that express antibodies that bind to a labeled antigen. The methods of the invention are useful, for example, to screen for antibodies, for example, with improved expression, stability, and/or affinity. In another aspect, the invention is based, in part, on novel antibodies that bind to IL-13 or VEGF. Anti-IL-13 antibodies of the invention are useful, e.g., for the diagnosis and/or treatment of IL-13-mediated disorders. Anti-VEGF antibodies described herein are useful, e.g., for the diagnosis and/or treatment of disorders associated with pathological angiogenesis (e.g., cancer) and/or to inhibit vascular permeability.

A. Exemplary Methods of the Invention

The invention provides methods of identifying a bacterium comprising a binding polypeptide that specifically binds a target molecule. The invention also provides methods of identifying a bacterium having improved expression of a binding polypeptide. The invention also provides methods of identifying a binding polypeptide having improved expression and/or stability.

For example, in some instances, the invention provides a method for identifying a bacterium comprising a binding polypeptide that specifically binds a target molecule, the method comprising the following steps: (a) providing a bacterium having an outer membrane permeable to a molecule having a molecular weight greater than about 1 kDa (e.g., about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 25 kDa, 30 kDa, 40 kDa, 50 kDa, or higher), the bacterium expressing a nucleic acid encoding a candidate binding polypeptide, wherein the candidate binding polypeptide is present within the periplasm of the bacterium; (b) contacting the bacterium with a detectably labeled target molecule; and (c) identifying the bacterium as comprising a binding polypeptide by the presence of the labeled target molecule within the periplasm. In some embodiments, the bacterium remains viable following step (c). In some embodiments, the target molecule is labeled using a covalently attached label. In other embodiments, the target molecule is labeled using a non-covalently attached label.

In another example, in some instances, the invention provides a method for identifying a bacterium with improved expression of a binding polypeptide that specifically binds a target molecule, the method comprising the following steps: (a) providing a bacterium having an outer membrane permeable to a molecule having a molecular weight greater than about 1 kDa (e.g., about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 25 kDa, 30 kDa, 40 kDa, 50 kDa, or higher), the bacterium expressing a nucleic acid encoding a binding polypeptide, wherein the binding polypeptide is present within the periplasm of the bacterium; (b) contacting the bacterium with a detectably labeled target molecule; and (c) identifying the bacterium as having improved expression of the binding polypeptide by the presence of the labeled target molecule within the periplasm. In some embodiments, the bacterium remains viable following step (c). In some embodiments, the target molecule is labeled using a covalently attached label. In other embodiments, the target molecule is labeled using a non-covalently attached label.

In some instances of any of the preceding methods, the method further includes repeating the steps of the method at least once. For example, the method can further include repeating the steps of the method at least 1, 2, 3, 4, 5, 6, 7, 8, 9, or 10 or more times. In some embodiments, at least one step of the method is repeated. In some instances, all of the steps of the method may repeated at least once (e.g., repeated 1, 2, 3, 4, 5, 6, 7, 8, 9, or 10 or more times). In some instances, all of the steps of the method may be repeated sequentially at least once (e.g., repeated 1, 2, 3, 4, 5, 6, 7, 8, 9, or 10 or more times). In some instances, the steps of the method are repeated 2 times. In some instances, the steps of the method are repeated 3 times. In some instances, the following steps are repeated: (a) providing a bacterium having an outer membrane permeable to a molecule having a molecular weight greater than about 1 kDa (e.g., about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 25 kDa, 30 kDa, 40 kDa, 50 kDa, or higher), the bacterium expressing a nucleic acid encoding a candidate binding polypeptide, wherein the candidate binding polypeptide is present within the periplasm of the bacterium; (b) contacting the bacterium with a detectably labeled target molecule; and (c) identifying the bacterium as comprising a binding polypeptide by the presence of the labeled target molecule within the periplasm. In some instances, the method further comprises incubating the bacterium in growth medium prior to repeating the steps of the method. Examples of bacterial growth media include CRAP, SOC, Luria Broth (LB), or any other bacterial growth medium known in the art.

In some instances of any of the preceding methods, the target molecule has a molecular weight less than about 500 kDa (e.g., less than about about 500 kDa, about 480 kDa, about 460 kDa, about 440 kDa, about 420 kDa, about 440 kDa, about 420 kDa, about 400 kDa, about 380 kDa, about 360 kDa, about 340 kDa, about 320 kDa, about 300 kDa, about 280 kDa, about 260 kDa, about 250 kDa, about 220 kDa, about 200 kDa, about 180 kDa, about 160 kDa, about 150 kDa, about 130 kDa, about 120 kDa, about 110 kDa, about 100 kDa, about 80 kDa, about 60 kDa, about 40 kDa, or about 20 kDa). Exemplary target molecules have molecular weights in the ranges of about 1 kDa to about 500 kDa, about 1 kDa to about 400 kDa, about 1 kDa to about 300 kDa, about 1 kDa to about 250 kDa, about 1 kDa to about 230 kDa, about 1 kDa to about 220 kDa, about 1 kDa to about 200 kDa, about 1 kDa to about 180 kDa, about 1 kDa to about 160 kDa, about 1 kDa to about 140 kDa, about 1 kDa to about 120 kDa, about 1 kDa to about 100 kDa, about 1 kDa to about 80 kDa, about 1 kDa to about 60 kDa, about 1 kDa to about 40 kDa, about 1 kDa to about 20 kDa, about 1 kDa to about 10 kDa, about 8 kDa to about 500 kDa, about 8 kDa to about 400 kDa, about 8 kDa to about 300 kDa, about 8 kDa to about 250 kDa, about 8 kDa to about 220 kDa, about 8 kDa to about 200 kDa, about 8 kDa to about 180 kDa, about 8 kDa to about 160 kDa, about 8 kDa to about 140 kDa, about 8 kDa to about 120 kDa, about 8 kDa to about 100 kDa, about 8 kDa to about 80 kDa, about 8 kDa to about 60 kDa, about 8 kDa to about 40 kDa, or about 8 kDa to about 20 kDa.

In some instances of any of the preceding methods, the target molecule has a molecular weight of about 10 kDa or higher. For example, in some embodiments, the target molecule has a molecular weight in the range of about 10 kDa to about 700 kDa, about 10 kDa to about 600 kDa, about 10 kDa to about 500 kDa, about 10 kDa to about 480 kDa, about 10 kDa to about 470 kDa, about 10 kDa to about 460 kDa, about 10 kDa to about 450 kDa, about 10 kDa to about 440 kDa, about 10 kDa to about 430 kDa, about 10 kDa to about 420 kDa, about 10 kDa to about 410 kDa, about 10 kDa to about 400 kDa, about 10 kDa to about 390 kDa, about 10 kDa to about 380 kDa, about 10 kDa to about 370 kDa, about 10 kDa to about 360 kDa, about 10 kDa to about 350 kDa, about 10 kDa to about 340 kDa, about 10 kDa to about 330 kDa, about 10 kDa to about 320 kDa, about 10 kDa to about 310 kDa, about 10 kDa to about 300 kDa, about 10 kDa to about 290 kDa, about 10 kDa to about 280 kDa, about 10 kDa to about 270 kDa, about 10 kDa to about 260 kDa, about 10 kDa to about 250 kDa, about 10 kDa to about 240 kDa, about 10 kDa to about 230 kDa, about 10 kDa to about 220 kDa, about 10 kDa to about 210 kDa, about 10 kDa to about 200 kDa, about 10 kDa to about 190 kDa, about 10 kDa to about 180 kDa, about 10 kDa to about 170 kDa, about 10 kDa to about 160 kDa, about 10 kDa to about 150 kDa, about 10 kDa to about 140 kDa, about 10 kDa to about 130 kDa, about 10 kDa to about 120 kDa, about 10 kDa to about 110 kDa, about 10 kDa to about 100 kDa, about 10 kDa to about 90 kDa, about 10 kDa to about 80 kDa, about 10 kDa to about 70 kDa, about 10 kDa to about 60 kDa, about 10 kDa to about 50 kDa, about 10 kDa to about 40 kDa, about 10 kDa to about 30 kDa, about 10 kDa to about 20 kDa, or about 10 kDa to about 15 kDa.

In some instances, the invention provides a method for identifying a bacterium comprising a binding polypeptide that specifically binds a target molecule, the method comprising the following steps: (a) providing a bacterium comprising a mutation that allows for diffusion of membrane impermeant molecules across the outer membrane into the periplasm, the bacterium expressing a nucleic acid encoding a candidate binding polypeptide, wherein the candidate binding polypeptide is present within the periplasm of the bacterium; (b) contacting the bacterium with a detectably labeled target molecule; and (c) identifying the bacterium as comprising a binding polypeptide by the presence of the labeled target molecule within the periplasm. In some embodiments, the bacterium remains viable following step (c). In some instances, the method further comprises subjecting the bacterium to conditions that permeabilize the outer membrane of the bacterium prior to step (b). In some instances, the method further comprises resealing the outer membrane of the bacterium following contacting the bacterium with a detectably labeled target molecule.

In other instances, the invention provides a method for identifying a bacterium with improved expression of a binding polypeptide that specifically binds a target molecule, the method comprising the following steps: (a) providing a bacterium comprising a mutation that allows for diffusion of membrane impermeant molecules across the outer membrane into the periplasm, the bacterium expressing a nucleic acid encoding a binding polypeptide, wherein the binding polypeptide is present within the periplasm of the bacterium; (b) contacting the bacterium with a detectably labeled target molecule; and (c) identifying the bacterium as having improved expression of the binding polypeptide by the presence of the labeled target molecule within the periplasm. In some embodiments, the bacterium remains viable following step (c). In some instances, the method further comprises subjecting the bacterium to conditions that permeabilize the outer membrane of the bacterium prior to step (b). In some instances, the method further comprises resealing the outer membrane of the bacterium following contacting the bacterium with a detectably labeled target molecule.

In some instances of any of the preceding methods, the method further includes repeating the steps of the method at least once. For example, the method can further include repeating the steps of the method at least 1, 2, 3, 4, 5, 6, 7, 8, 9, or 10 or more times. In some embodiments, at least one step of the method is repeated. In some instances, all of the steps of the method may repeated at least once (e.g., repeated 1, 2, 3, 4, 5, 6, 7, 8, 9, or 10 or more times). In some instances, all of the steps of the method may be repeated sequentially at least once (e.g., repeated 1, 2, 3, 4, 5, 6, 7, 8, 9, or 10 or more times). In some instances, the steps of the method are repeated 2 times. In some instances, the steps of the method are repeated 3 times. In some instances, the following steps are repeated: (a) providing a bacterium comprising a mutation that allows for diffusion of membrane impermeant molecules across the outer membrane into the periplasm, the bacterium expressing a nucleic acid encoding a candidate binding polypeptide, wherein the candidate binding polypeptide is present within the periplasm of the bacterium; (b) contacting the bacterium with a detectably labeled target molecule; and (c) identifying the bacterium as comprising a binding polypeptide by the presence of the labeled target molecule within the periplasm. In some instances, the method further comprises incubating the bacterium in growth medium prior to repeating the steps of the method.

In other instances, the invention provides a method for identifying a bacterium comprising a binding polypeptide that specifically binds a target molecule, the method comprising the steps of: (a) providing a bacterium expressing a nucleic acid encoding a candidate binding polypeptide, wherein the candidate binding polypeptide is present within the periplasm of the bacterium; (b) subjecting the bacterium to conditions that permeabilize the outer membrane of the bacterium; (c) contacting the bacterium with a detectably labeled target molecule; (d) resealing the outer membrane of the bacterium following step (c); and (e) identifying the bacterium as comprising a binding polypeptide by the presence of the labeled target molecule within the periplasm. In some instances, the bacterium remains viable after step (e) of the method.

In yet other instances, the invention provides a method for identifying a bacterium with improved expression of a binding polypeptide that specifically binds a target molecule, the method comprising the steps of: (a) providing a bacterium expressing a nucleic acid encoding a binding polypeptide, wherein the binding polypeptide is present within the periplasm of the bacterium; (b) subjecting the bacterium to conditions that permeabilize the outer membrane of the bacterium; (c) contacting the bacterium with a detectably labeled target molecule; (d) resealing the outer membrane of the bacterium following step (c); and (e) identifying the bacterium as having improved expression of the binding polypeptide by the presence of the labeled target molecule within the periplasm. In some instances, the bacterium remains viable after step (e) of the method.

In some instances, the method further includes repeating the steps of the method at least once. For example, the method can further include repeating the steps of the method at least 1, 2, 3, 4, 5, 6, 7, 8, 9, or 10 or more times. In some embodiments, at least one step of the method is repeated. In some instances, all of the steps of the method may repeated at least once (e.g., repeated 1, 2, 3, 4, 5, 6, 7, 8, 9, or 10 or more times). In some instances, all of the steps of the method may be repeated sequentially at least once (e.g., repeated 1, 2, 3, 4, 5, 6, 7, 8, 9, or 10 or more times). In some instances, the steps of the method are repeated 2 times. In some instances, the steps of the method are repeated 3 times. In some instances, the following steps are repeated: (a) providing a bacterium expressing a nucleic acid encoding a candidate binding polypeptide, wherein the candidate binding polypeptide is present within the periplasm of the bacterium; (b) subjecting the bacterium to conditions that permeabilize the outer membrane of the bacterium; (c) contacting the bacterium with a detectably labeled target molecule; (d) resealing the outer membrane of the bacterium following step (c); and (e) identifying the bacterium as comprising a binding polypeptide by the presence of the labeled target molecule within the periplasm.

In any of the preceding methods, the bacterium may have improved expression of the binding polypeptide by at least about 1%, about 5% about 10%, about 20%, about 30%, about 40%, about 50%, about 60%, about 70%, about 80%, about 90%, about 100%, about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, about 40-fold, about 45-fold, about 50-fold, about 100-fold, or more. In some instances, the bacterium may have between a 1- and 10-fold improved expression, between a 1- and 7-fold improved expression, between a 1- and 6-fold improved expression, between a 1- and 5-fold improved expression, between a 1- and 4-fold improved expression, between a 1- and 3-fold improved expression, between a 2- and 10-fold improved expression, between a 2- and 8-fold improved expression, or between a 2- and 6-fold improved expression. In some embodiments, the improvement is relative to the expression level of the binding polypeptide in a wild-type bacterium. In other embodiments, the improvement is relative to the expression level of the binding polypeptide in a mutant bacterium.

In any of the preceding methods, the bacterium may remain viable after the steps of the method have been performed. In some instances, the bacterium may undergo cell division at least 1, 2, 3, 4, 5, 6, 7, 8, 9, 10, 11, 12, 13, 14, 15, 16, 17, 18, 19, or 20 times or more after the steps of the method have been performed. In some instances, viability is measured using a viability stain, e.g., SYTOX® Green, propidium iodide, or other viability stains known in the art. In some instances, viability is measured using a live/dead staining kit such as LIVE/DEAD® cell viability assays from Life Technologies. In some instances, viability is measured by plating the bacterium on a bacterial medium plate. In some instances, a viable cell will give rise to a colony following plating on a bacterial medium plate.

In any of the preceding methods, the bacterium may comprise a mutation that allows for diffusion of membrane irnpermeant molecules across the outer membrane into the periplasm. Mutations that may allow for diffusion of membrane impermeant molecules across the outer membrane into the periplasm (which in some cases may also be referred to as "periplasmic-leaky" or "Iky" mutants) are described, for example, in Hancock, *Ann. Rev. Microbial.* 38: 237-264, 1984, including but not limited to deep-rough (heptose-deficient) mutants of *E. coli* and *S. typhimurium* (e.g., rfaD, rfaE, rfaH, and rfaRd), which may affect lipopolysaccharide (LPS) composition in the outer membrane, env mutants (e.g., envA, envB, envM-T), and colicin-tolerant mutants in *E. coli* (e.g, to/C and to/A,B). In some instances, the mutation is in a gene encoding an outer membrane protein and/or a protein that affects lipopolysaccharide (LPS) composition. In some instances, the mutation is in a gene encoding an outer membrane protein, for example, major outer membrane lipoprotein Lpp (Lpp), a porin, or TolC. In some instances, the outer membrane protein is Lpp. Any suitable mutation in the gene encoding Lpp may be used. Exemplary lpp mutations include, but are not limited to, lpp-1; lpp-21; lpp-3; lpp5508; lpp-6; lpp::Tn5KAN-2; lppD70E, G, or S; lppK75S or T; lppK78R; lppR77D or L; lppS22D; lppY76C, D, E, G, N, P, or S; lppY76F, H, I, or L; Δlpp, Δlpp-254, and Δlpp-752::kan, or those described herein. Such lpp mutations may be may be acquired from, for example, a repository such as the CGSC (The *Coli Genetic Stock Center*). In other instances, a mutation in the gene encoding Lpp may be made using standard molecular genetics approaches. In some embodiments, the mutation is in a gene encoding a protein that affects LPS composition, for example, Env proteins (e.g., EnvA, EnvB, and EnvM), RfaD, RfaE, RfaH, RfaRd, TolA, TolB, and TolD.

In any of the preceding methods, the method may comprise subjecting the bacterium to conditions that permeabilize the outer membrane. In some instances, the conditions that permeabilize the outer membrane comprise treating the bacterium with a permeabilization agent. In some instances, a permeabilization agent is selected from chelators (including divalent cation chelators (e.g., EDTA, BAPTA, and EGTA)), NaCl, sucrose, antibiotics (e.g., aminoglycosides (e.g., streptomycin and gentamicin), polymyxin B, deacylated polymyxin, octapeptin, and benzyl penicillin), detergents, lysozyme, Tris, Tris-EDTA, ascorbate, polylysine, benzalkoniurn chloride, protamine, bactericidal/permeability-increasing protein (BPI), serum and/or complement, $Ca^{2+}$, or combinations thereof. In some embodiments, the permeabilization agent comprises a chelator. In some instances, the chelator is a divalent cation chelator (including, e.g., EDTA, BAPTA, and EGTA). In some embodiments, the divalent cation chelator is EDTA. In some instances, the concentration of the chelator, for example, EDTA, is between about 1 µM and about 15 mM, e.g., about 1 µM, 10 µM, 100 µM, 500 µM, 1 mM, 2 mM, 3 mM, 4 mM, 5 mM, 6 mM, 7 mM, 8 mM, 9 mM, 10 mM, 11 mM, 12 mM, 13 mM, 14 mM, or 15 mM. In some instances, the concentration of EDTA is 5 mM. In some instances, the permeabilization agent further includes a buffering agent, for example, phosphate buffered saline (PBS). In some instances, the permeabilization agent further comprises bovine serum albumin. In some instances, the BSA is present at between 1% (w/v) to about 10% (w/v), e.g., 1%, 2%, 3%, 4%, 5%, 6%, 7%, 8%, 9%, or 10%.

In any of the preceding methods, the method may comprise resealing the outer membrane of the bacterium. The outer membrane may, but need not, be completely resealed. Partial resealing to a level that allows for cell viability is sufficient for the methods of the invention. In some instances, the outer membrane is resealed if the membrane permeability barrier is restored to within 50%, 60%, 70%, 80%, 90%, 95%, 99%, or 100% as compared to a reference or wild-type bacterial outer membrane (e.g., the outer membrane of an *E. coli* 62A7 cell). In some instances, substantially resealing the outer membrane of the bacterium comprises contacting the bacterium with a salt of $Mg^{2+}$, $Mn^{2+}$, $Ca^{2+}$, $Zn^{2+}$, $Fe^{2+}$, $Na^+$, $K^+$ and the like, for instance, salts of the preceding cations with anions such as $SO_4^{2-}$, $F^-$, $Cl_2^-$, $SO_3^{2-}$, $PO_4^{3-}$, and the like. In some instances, substantially resealing the outer membrane of the bacterium comprises contacting the bacterium with $MgCl_2$. In some embodiments, the concentration of $MgCl_2$ is between about 1 mM and about 50 mM, e.g., about 1 mM, 2 mM, 5 mM, 10 mM, 15 mM, 20 mM, 25 mM, 30 mM, 35 mM, 40 mM, 45 mM, or 50 mM.

In any of the preceding methods, the step of contacting the bacterium with a detectably labeled target molecule may further comprise contacting the bacterium with a nucleic acid dye. In some instances, the nucleic acid dye is selected from the group consisting of Hoechst 33342 (also referred to as Hoechst stain), 4',6-diamidino-2-phenylindole (DAPI), SYTO® 9, SYTO® 11, SYTO® 12, SYTO® 13, SYTO® 14, SYTO® 15, SYTO® 16, SYTO® 17, SYTO® 41, SYTO® 43, SYTO® 42, SYTO®44, SYTO® 40, SYTO® 45, SYTO® 59, SYTO® 60, SYTO® 61, SYTO® 62, and SYTO® 63, SYTO® 64. In some embodiments, a nucleic acid dye that stains bacterial cells with an efficiency of at least about 60% (e.g., 60%, 65%, 70%, 75%, 80%, 85%, 90%, 95%, 99%, or more) is used. In some embodiments, a nucleic acid dye that stains bacterial cells with an efficiency of at least about 85% is used.

In any of the preceding methods, the detectably labeled target molecule may comprise a fluorescent label (also referred to as a fluorophore). In some embodiments, any fluorescent label compatible with flow cytometry (e.g., FACS™) detection may be used. For example, any fluorescent label with a quantum yield that allows sorting by flow cytometry (e.g., FACS™) may be used. In some instances, the fluorescent label includes a fluorescent dye or a fluorescent polypeptide. Various fluorescent labels are commercially available from a variety of distributors, for example, Life Technologies. A fluorescent label may be selected based on its excitation and emission profiles.

Non-limiting examples of fluorescent dyes that may be used include but are not limited to ALEXA® dyes (e.g., ALEXA FLUOR® 488, ALEXA FLUOR® 514, ALEXA FLUOR® 532, ALEXA FLUOR® 555, ALEXA FLUOR® 546, ALEXA FLUOR® 568, ALEXA FLUOR® 594, ALEXA FLUOR® 610, ALEXA FLUOR® 633, ALEXA FLUOR® 647 ALEXA FLUOR® 660, ALEXA FLUOR® 680, ALEXA FLUOR® 700, ALEXA FLUOR® 750, and ALEXA FLUOR® 790), DYLIGHT® dyes (e.g., DYLIGHT® 350, DYLIGHT® 405, DYLIGHT® 488, DYLIGHT® 550, DYLIGHT® 594, DYLIGHT® 633, DYLIGHT® 650, DYLIGHT® 680, DYLIGHT® 755, and DYLIGHT® 800), cyanine dyes (e.g., CY®2, CY®3, and CY®5), BODIPY, TEXAS RED®, fluorescein and its derivatives (e.g., fluorescein isothiocyanate, FITC), and rhodamine and its derivatives (e.g., tetramethylrhodamine, TRITC). In some instances, the fluorescent dye is selected from the group consisting of: ALEXA FLUOR® 488, ALEXA FLUOR® 647, and DYLIGHT® 649.

Exemplary fluorescent polypeptides that may be used include but are not limited to blue/UV fluorescent proteins (including TagBFP, rnTagBFP2, Azurite, EBFP2, mKalama1, Sirius, Sapphire, and T-Sapphire), cyan fluorescent proteins (e.g., ECFP, Cerulean, SCFP3A, mTurquoise, mTurquoise2, monomeric Midoriishi-Cyan, TagCFP, and mTFP1), green fluorescent proteins (e.g., GFP, EGFP, Emerald, Superfolder GFP, monomeric Azami Green, TagGFP2, mUKG, mWasabi, Clover, and mNeonGreen), yellow fluorescent proteins (e.g., EYFP, Citrine, Venus, SYFP2, and TagYFP), orange fluorescent proteins (e.g., monomeric Kusabira-Orange, mKOk, mKO2, mOrange, and mOrange2), red fluorescent proteins (e.g., mRaspberry, mCherry, mStrawberry, mTangerine, tdTomato, RFP, TagRFP, TagRFP-T, mApple, mRuby, and mRuby2), far-red fluorescent proteins (e.g. mPlum, HcRed-Tandem, mKate2, mNeptune, NirFP), photoactivatable fluorescent proteins (e.g., PA-GFP, PAmCherry1, and PATagRFP), and photoconvertible fluorescent proteins (e.g., Kaede, KikGR1, PS-CFP2, mEos2, mEos3.2, and pSmOrange).

In some embodiments, the bacterium is contacted with a detectably labeled target molecule at a temperature of about 4° C. to about 25° C. (e.g., about 4° C., 5° C., 6° C., 7° C., 8° C., 9° C., 10° C., 12° C., 14° C., 16° C., 18° C., 20° C., 22° C., 24° C., or 25° C.). In some embodiments, the temperature is about 4° C.

Any of the preceding methods may further include at least one wash step (e.g., 1, 2, 3, 4, 5, 6, 7, 8, 9, or 10 wash steps), which involve resuspending the bacterium in a wash buffer. In some instances, the at least one wash step is performed following contacting the bacterium with a detectably labeled target molecule. In some instances, the wash buffer includes a buffering agent, e.g., PBS. In some instances, the wash buffer comprises phosphate buffered saline. In some instances, the wash buffer further comprises $MgCl_2$. In some instances, the wash buffer comprises between 1 mM and 50 mM $MgCl_2$ (e.g., 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 30 mM, 40 mM, or 50 mM $MgCl_2$.

In any of the preceding methods, the selecting step may further include flow cytometry (e.g., FACS™). In some instances, the flow cytometry includes sorting for single cells and sorting based on the signal of the detectably labeled target molecule. In some instances, the flow cytometry includes sorting based on the signal of a nucleic acid dye. In some instances, the flow cytometry comprises sequentially (i) sorting based on the signal of a nucleic acid dye; (ii) sorting for single cells; and (iii) sorting based on the signal of the detectably labeled target molecule. In some embodiments, the cells are at a concentration of between about $1\times10^5$ to about about $1\times10^{12}$ cells/ml, e.g., about $1\times10^5$ cells/ml, about $1\times10^6$ cells/ml, about $1\times10^7$ cells/ml, about $1\times10^6$ cells/ml, about $1\times10^9$ cells/ml, about $1\times10^{10}$ cells/ml, about $1\times11$ cells/ml, or about $1\times10^{12}$ cells/ml.

In any of the preceding methods, the bacterium may be a bacterium that includes an inner membrane, a periplasm, and outer membrane. In some embodiments, the bacterium is a gram-negative bacterium. For example, in some instances, the bacterium is an E. coli. Any suitable strain or genetic background of E. coli may be used. Commonly-used strains and genetic backgrounds of E. coli are well known in the art Exemplary E. coli strains include, but are not limited to, laboratory strains such as K-12 and its substrains (e.g., Clifton wild type, W3110, DH5αE, and the like), and E. coli B and its substrains (e.g., BL21, BL21(DE3), and the like). In some embodiments, the E. coli is derived from strain 62A7. In some embodiments, the E. coli is derived from strain 33D3, In some embodiments, the E. coli is derived from strain 66C4.

In any of the preceding methods, the binding polypeptide may be expressed in soluble form in the periplasm of the bacterium.

In any of the preceding methods, the binding polypeptide may be expressed as a fusion protein in the periplasm of the bacterium. In some instances, the binding polypeptide is expressed as a fusion protein with a protein, or a fragment thereof, that localizes to the outer face of the inner membrane. It is to be understood that additional polypeptide sequences, for example, linker polypeptides, may be added to the fusion protein. Such a fusion protein may be used to anchor the binding polypeptide to the outer face of the inner membrane. In some embodiments, a leader peptide and the first six amino acids of an inner membrane lipoprotein (e.g., NlpA) may be included in the fusion protein. Such a fusion protein may serve as an N-terminal anchor of the binding polypeptide to the outer face of the inner membrane. In some instances, the fusion protein includes an inner membrane protein or fragment thereof selected from Aas, AcrE (EnvC), AmiC, AmiD, ArtM, AraH, ArtQ, BtuC, CheY, CysT, CysW, DppB, DppC, DsbB, DsbD, ExbD, ExbB, FecC, FecD, FecR, FepD, FhuB, GlnP, HisM, HisQ, LacY, a lipoprotein, LivH, LivM, LivA, LivE, MalF, MalG, MalC, MalD, MglC, ModB, NikB, NikC, NosY, OppB, phage-encoded celB, PhnM, PotB, PotC, PotH, PotI, ProW, PstA, PstC, pullulanase of K. pneumoniae, RbsC, SecY, TatC, TraB TolC, TonB, UgpA, or UgpE. In some embodiments, any lipoprotein or fragment thereof which includes a signal sequence and an aspartate at amino acid position 2 (either present in the wild-type protein or added by mutagenesis (e.g., site-directed mutagenesis) may be included in the fusion protein. In some embodiments, a single transmembrane loop of any cytoplasmic protein may be used as a membrane anchor. The fusion protein may be an N-terminal fusion or a C-terminal fusion.

In some instances, the bacterium expresses a fusion protein that localizes to the outer face of the inner membrane that comprises a domain or fragment thereof that can specifically bind to the binding polypeptide. For example, if the binding polypeptide is an antibody, an antibody-binding domain or fragment thereof may be included in a fusion protein with an inner membrane protein or fragment thereof as described above. In some instances, the antibody-binding domain may be derived from allergen Asp fl 1, Asp fl2, or Asp fl3 of Aspergillus flavus, Fc-gamma RI, Fc-gamma RII, Fc-gamma RII-a, Fc-gamma RII-b, Fc-gamma RII-c, FC-gamma RIII, Fc-gamma RIII-a, Fc-gamma RIII-b, FcRn, MRP protein of Streptococcus pyogenes, protein A of S. aureus (spa), protein B of Streptococcus agalactiae, protein G of Streptococcus sp, group G (spg), protein H of Streptococcus pyogenes, or protein sbi of S. aureus. In some instances, the domain is derived from protein A of S. aureus (e.g., the ZZ domain, which binds to the Fc region of IgG. For other binding polypeptides, protein-protein interaction domains and/or epitope tags that bind to the binding polypeptide may be included in the fusion protein.

In any of the preceding methods, step (a) may include providing a plurality of bacteria, wherein the bacteria include a library of nucleic acids, each encoding a candidate binding polypeptide. In some instances, the library of nucleic acids may include two or more nucleic acids encoding polypeptides that are substantially the same, preferably identical, in sequence except for the sequence of a variant at one or more particular positions. For example, in some instances, the library comprises a plurality of nucleic acids encoding candidate binding polypeptide variants having one or more (e.g., 1, 2, 3, 4, 5, 6, 7, 8, 9, 10, 20, 30, 40, 50, 60, 70, 80, or more) amino acid residue alterations as compared to a reference binding polypeptide.

For instance, in any of the preceding methods, the library may include a plurality of nucleic acids encoding candidate antibody variants, wherein each candidate antibody variant comprises one or more amino acid residue alterations (e.g., 1, 2, 3, 4, 5, 6, 7, 8, 9, 10, 15, 20, 25, 30, 35, 40, 45, 50, 60, 70, 80, or more) as compared to a reference antibody. The amino acid residue alteration may be in any position of the antibody, for instance, the VH and/or VL and/or a constant domain. For example, in some instances, the candidate antibody variant includes one or more amino acid residue alterations in an HVR and/or an FR of the VH and/or VL. In some instances, the candidate antibody variant includes one or more amino acid residue alterations in an HVR (e.g., HVR-H1, HVR-H2, and/or HVR-H3) and/or an FR (e.g., FR-H1, FR-H2, FR-H3, and/or FR-H4) of the VH. In some instances, the candidate antibody variant includes one or more amino acid residue alterations in an HVR (e.g., HVR-H1, HVR-H2, and/or HVR-H3) of the VH. In some instances, the candidate antibody variant includes one or more amino acid residue alterations in an FR (e.g., FR-H1, FR-H2, FR-H3, and/or FR-H4) of the VH. In other instances, the candidate antibody variant includes one or more amino acid residue alterations in an HVR (e.g., HVR-L1, HVR-L2, and/or HVR-L3) and/or FR (e.g., FR-L1, FR-L2, FR-L3, and/or FR-L4) of the VL. In some instances, the candidate antibody variant includes one or more amino acid residue alterations in an HVR (e.g., HVR-L1, HVR-L2, and/or HVR-L3) of the VL. In some instances, the candidate antibody variant includes one or more amino acid residue alterations in an FR (e.g., FR-L1, FR-L2, FR-L3, and/or FR-L4) of the VL. The amino acid residue alterations may be in a surface-exposed residue or a buried residue. In any of the preceding methods, the library may include a plurality of nucleic acids encoding candidate antibody variants, wherein each candidate antibody variant comprises an amino acid residue alteration in an FR of the VH or VL as compared to a reference antibody, wherein the amino acid residue alteration: (a) was identified in a naturally occurring antibody having the same subtype as the reference antibody, and/or (b) is in a amino acid residue predicted to be buried. For example, in some instances, the library may include a plurality of nucleic acids encoding candidate antibody variants, wherein each candidate antibody variant comprises an amino acid residue alteration in an FR of the VH or VL as compared to a reference antibody, wherein the amino acid residue alteration: (a) was identified in a naturally occurring antibody having the same subtype as the reference antibody, and (b) is in a amino acid residue predicted to be buried. In some instances, the amino acid residue alteration in the naturally occurring antibody is due to somatic hypermutation.

An amino acid residue may be predicted and/or determined to be buried (e.g., not solvent accessible) or surface-exposed (e.g., solvent accessible) using any method known in the art. For example, an amino acid residue may be predicted to be buried using any of a number of algorithms known in the art. Preferably, solvent accessible positions are determined using coordinates from a three-dimensional model of an antibody, preferably using a computer program such as the InsighfH Program (Accelrys, San Diego, Calif.). Buried positions can also be predicted using algorithms known in the art (e.g., Lee et al. *J. Mol. Biol.* 55: 379, 1971 and Connolly, *J. Appl. Cryst.* 16: 548, 1983). Prediction of buried positions can be performed using software suitable for protein modeling and three-dimensional structural information obtained from an antibody. Software that can be utilized for these purposes includes SYBYL Biopolymer Module software (Tripos Associates). Generally, where an algorithm (program) requires a user input size parameter, the "size" of a probe which is used in the calculation is set at about 1.4 Angstrom or smaller in radius. In addition, determination of buried and/or surface-exposed regions and area methods using software for personal computers has been described by Pacios, *Comput. Chem.* 18(4): 377-386, 1994 and *J. Mol. Model.* 1: 46-53, 1995.

In any of the preceding methods, the library may include from about 2 binding polypeptides to about $10^{14}$ or more binding polypeptides (e.g., about 2, about 5, about 10, about 15, about 20, about 40, about 50, about 60, about 70, about 80, about 90, about 100, about 200, about 500, about $10^3$, about $10^4$, about $10^5$, about $10^6$, about $10^7$, about $10^8$, about $10^9$, about $10^{10}$, about $10^{11}$, about $10^{12}$, about $10^{13}$, or about $10^{14}$ binding polypeptides). In some instances, the library may include about $10^8$ binding polypeptides.

Any of the preceding methods may include a step of identifying a candidate binding polypeptide as having an increased expression level based on the amount of labeled target molecule within the periplasm. In some instances, the increased expression level is determined by Western blot, IHC, mass spectrometry, enzyme linked immunosorbent assay (ELISA), or by other methods known in the art. In some instances, the candidate binding polypeptide has between a 1- and 20-fold increase in expression, e.g., 1-fold, 2-fold, 3-fold, 4-fold, 5-fold, 6-fold, 7-fold, 8-fold, 9-fold, 10-fold, 11-fold, 13-fold, 14-fold, 15-fold, 16-fold, 17-fold, 18-fold, 19-fold, or 20-fold increase in expression, as compared to a reference or wild-type binding polypepticle. For example, the candidate binding polypeptide may have between a 1- and 10-fold increase in expression, between a 1- and 7-fold increase in expression, between a 1- and 6-fold increase in expression, between a 1- and 5-fold increase in expression, between a 1- and 4-fold increase in expression, between a 1- and 3-fold increase in expression, between a 2- and 10-fold increase in expression, between a 2- and 8-fold increase in expression, or between a 2- and 6-fold increase in expression. In some embodiments, the candidate binding polypeptide has increased expression in both bacterial (e.g., *E. coli*) and mammalian cells. In some embodiments, the increase is relative to the expression level of a wild-type binding polypeptide. In other embodiments, the increase is relative to the expression level of a variant binding polypeptide.

Any of the preceding methods may include a step of identifying a candidate binding polypeptide as having increased stability based on the amount of labeled target molecule within the periplasm. In some instances, the increased stability is determined by differential scanning fluorimetry, circular dichroism, spectroscopy, or other methods known in the art. In some instances, the candidate binding polypeptide has an increased melting temperature ($T_m$) of between 1° C. and 20° C., e.g., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C., as compared to a reference or wild-type binding polypeptide. In some instances, the candidate binding polypeptide has an increased $T_m$ of between 1° C. and 10° C., between 1° C. and 9° C., between 1° C. and 8° C., between 1° C. and 7° C., between 1° C. and 6° C., between 1° C. and 5° C., between 1° C. and 4° C., between 1° C. and 3° C., between 1° C. and 2° C., between 2° C. and 10° C., between 2° C. and 9° C., between 2° C. and 8° C., between 2° C. and 7° C., between 2° C. and 6° C., between 2° C. and 5° C., between 2° C. and 4° C., or between 2° C. and 3° C. In some embodiments, the candidate binding polypeptide has increased stability in both bacterial (e.g., *E. coli*) and mammalian cells. In some embodiments, the candidate binding polypeptide has both increased stability and increased expression. In some embodiments, the increase is relative to the expression level of a wild-type binding polypeptide. In other embodiments, the increase is relative to the expression level of a variant binding polypeptide.

Any of the preceding methods may include a step of identifying a candidate binding polypeptide having increased binding affinity to a target molecule based on the amount of labeled target molecule within the periplasm. In some embodiments, the candidate binding polypeptide may have a 1.5-, 2-, 3-, 4-, 5-, 6-, 7-, 8-, 9-, 10-, 15-, or 20-fold increase in binding affinity to the target molecule compared to a reference binding polypeptide. For example, the method may include screening for an antibody with increased affinity compared to a reference antibody.

In any of the preceding methods, the binding polypeptide may be an antibody. In some instances, the antibody of any of the above methods is a monoclonal antibody, including a chimeric, humanized, or human antibody. In some instances, the antibody is an antibody fragment, e.g., a Fv, Fab, Fab', scFv, diabody, or F(ab')$_2$ fragment. In other instances, the antibody is a full length antibody, e.g., an intact IgG1 antibody, an intact IgG4 antibody, or other antibody class or isotype as defined herein. In another embodiment, the antibody is a half-antibody, for instance, a knob-into-hole half-antibody. See, for example, U.S. Pat. No. 5,731,168 for a description of knob-into-hole technology. In any of the preceding methods, the antibody may be a therapeutic antibody (e.g., a neutralizing antibody).

In any of the preceding methods, the binding polypeptide may be an antibody mimetic, for example, an affibody, an affilin, an affimer, an affitin, an alphabody, an anticalin, an avimer, a designed ankyrin repeat protein (DARPin), a fynomer, a Kunitz domain peptide, or a monobody. In other embodiments, the binding polypeptide may be a bacterial protein that localizes to the periplasm. In other embodiments, the binding polypeptide may be a mammalian protein. For example, in some embodiments, the binding polypeptide may be a cell surface receptor, a cytokine, or a growth factor.

Any of the preceding methods may further include isolating the nucleic acid following the selecting step. In some instances, the method further comprises determining the sequence of the nucleic acid.

In some aspects of any of the preceding methods, the bacterium may include a mutation affecting a gene that affects expression of the binding polypeptide, e.g., a transcription-regulating gene. In some instances, step (a) comprises providing a plurality of bacteria, wherein the plurality of bacteria comprise a library of nucleic acids, each encoding a mutant of the transcription-regulating gene. In some instances, the transcription-regulating gene is selected from a transcription initiation factor, an anti-sigma factor, an RNA polymerase subunit, or a transcription factor. In some instances, the transcription initiation factor is a sigma factor. In some instances, the sigma factor is selected from the group consisting of RpoD ($\sigma^{70}$), RpoE ($\sigma^{24}$), RpoH ($\sigma^{32}$), RpoS ($\sigma^{38}$), RpoN ($\sigma^{54}$), RpoF ($\sigma^{28}$), and FecI ($\sigma^{19}$). In particular instances, the sigma factor is RpoD ($\sigma^{70}$). In some instances, the mutation affecting the transcription-regulating gene is present on a synthetic plasmid. In other instances, the mutation affecting the transcription-regulating gene is present in the endogenous bacterial genome. In some instances, mutation affecting the transcription-regulating gene is due to error-prone PCR mutagenesis, chemical mutagenesis, transpositional mutagenesis, or targeted mutagenesis. In particular instances, the mutation affecting the transcription-regulating gene is due to error-prone PCR mutagenesis.

Any of the preceding methods may be used to identify a bacterium having improved expression of the binding polypeptide. In some instances, the bacterium may have improved expression of the binding polypeptide by at least about 1%, about 5% about 10%, about 20%, about 30%, about 40%, about 50%, about 60%, about 70%, about 80%, about 90%, about 100%, about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, about 40-fold, about 45-fold, about 50-fold, about 100-fold, or more. In some instances, the bacterium may have between a 1- and 10-fold improved expression, between a 1- and 7-fold improved expression, between a 1- and 6-fold improved expression, between a 1- and 5-fold improved expression, between a 1- and 4-fold improved expression, between a 1- and 3-fold improved expression, between a 2- and 10-fold improved expression, between a 2- and 8-fold improved expression, or between a 2- and 6-fold improved expression. In some embodiments, the improvement is relative to the expression level of the binding polypeptide in a wild-type bacterium. In other embodiments, the improvement is relative to the expression level of the binding polypeptide in a mutant bacterium.

B. Libraries

The invention provides libraries comprising a plurality of nucleic acids encoding binding polypeptides. For example, in some instances, the library comprises a plurality of nucleic acids encoding candidate binding polypeptide variants having one or more (e.g., 1, 2, 3, 4, 5, 6, 7, 8, 9, 10, 20, 30, 40, 50, 60, 70, 80, or more) amino acid residue alterations as compared to a reference binding polypeptide.

The candidate binding polypeptide may be a candidate antibody variant. In some instances, the candidate antibody variant is a monoclonal antibody, including a chimeric, humanized, or human antibody. In some instances, the candidate antibody variant is an antibody fragment, e.g., a Fv, Fab, Fab', scFv, diabody, or F(ab')$_2$ fragment. In other instances, the candidate antibody variant is a full-length antibody, e.g., an intact IgG1 antibody, an intact IgG4 antibody, or other antibody class or isotype as defined herein. In another embodiment, the candidate antibody variant is a half-antibody, for instance, a knob-into-hole half-antibody. In any of the preceding methods, the candidate antibody variant may be a therapeutic antibody (e.g., a neutralizing antibody).

In other instances, the candidate binding polypeptide may be an antibody mimetic, for example, an affibody, an affilin, an affimer, an affitin, an alphabody, an anticalin, an avimer, a designed ankyrin repeat protein (DARPin), a fynomer, a Kunitz domain peptide, or a monobody. In other embodiments, the binding polypeptide may be a bacterial protein that localizes to the periplasm. In other embodiments, the binding polypeptide may be a mammalian protein. For example, in some embodiments, the binding polypeptide may be a cell surface receptor, a cytokine, or a growth factor.

In some instances, the library may include a plurality of nucleic acids encoding candidate antibody variants, wherein each candidate antibody variant comprises one or more amino acid residue alterations (e.g., 1, 2, 3, 4, 5, 6, 7, 8, 9, 10, 15, 20, 25, 30, 35, 40, 45, 50, 60, 70, 80, or more) as compared to a reference antibody. The amino acid residue alteration may be in any position of the antibody, for instance, the VH and/or VL and/or a constant domain. For example, in some instances, the candidate antibody variant includes one or more amino acid residue alterations in an HVR and/or an FR of the VH and/or VL. In some instances, the candidate antibody variant includes one or more amino acid residue alterations in an HVR (e.g., HVR-H1, HVR-H2, and/or HVR-H3) and/or an FR (e.g., FR-H1, FR-H2, FR-H3, and/or FR-H4) of the VH. In some instances, the candidate antibody variant includes one or more amino acid residue alterations in an HVR (e.g., HVR-H1, HVR-H2, and/or HVR-H3) of the VH. In some instances, the candidate antibody variant includes one or more amino acid residue alterations in an FR (e.g., FR-H1, FR-H2, FR-H3, and/or FR-H4) of the VH. In other instances, the candidate antibody variant includes one or more amino acid residue alterations in an HVR (e.g., HVR-L1, HVR-L2, and/or HVR-L3) and/or FR (e.g., FR-L1, FR-L2, FR-L3, and/or FR-L4) of the VL. In some instances, the candidate antibody variant includes one or more amino acid residue alterations in an HVR (e.g., HVR-L1, HVR-L2, and/or HVR-L3) of the VL. In some instances, the candidate antibody variant includes one or more amino acid residue alterations in an FR (e.g., FR-L1, FR-L2, FR-L3, and/or FR-L4) of the VL. The amino acid residue alterations may be in a surface-exposed residue or a buried residue.

In some instances, the library may include a plurality of nucleic acids encoding candidate antibody variants, wherein each candidate antibody variant includes one or more amino acid residue alterations in an FR of the VH and/or VL as compared to a reference antibody, wherein the amino acid residue alteration: (a) was identified in a naturally occurring antibody having the same subtype as the reference antibody, and/or (b) is in a amino acid residue predicted to be buried. In some instances, the library may include a plurality of nucleic acids encoding candidate antibody variants, wherein each candidate antibody variant includes one or more amino acid residue alterations in an FR of the VH and/or VL as compared to a reference antibody, wherein the amino acid residue alteration: (a) was identified in a naturally occurring antibody having the same subtype as the reference antibody, and (b) is in a amino acid residue predicted to be buried. In some instances, each candidate antibody variant includes 1 amino acid residue alteration as compared to a reference antibody.

For example, in some instances, the library may include a plurality of nucleic acids encoding candidate antibody variants, wherein each candidate antibody variant comprises an amino acid residue alteration in an FR of the VH (e.g., FR-H1, FR-H2, FR-H3, or FR-H4) as compared to a reference antibody, wherein the amino acid residue alteration: (a) was identified in a naturally occurring antibody having the same subtype as the reference antibody, and (b) is in a amino acid residue predicted to be buried. In other instances, the library may include a plurality of nucleic acids encoding candidate antibody variants, wherein each candidate antibody variant comprises an amino acid residue alteration in an FR (e.g., FR-L1, FR-L2, FR-L3, or FR-L4) of the VL as compared to a reference antibody, wherein the amino acid residue alteration: (a) was identified in a naturally occurring antibody having the same subtype as the reference antibody, and (b) is in a amino acid residue predicted to be buried. In some instances, the amino acid residue alteration in the naturally occurring antibody is due to somatic hypermutation.

Naturally occurring antibodies having a VH and/or VL belonging to the same subtype as a reference antibody may readily be found in an antibody database, for example, the Kabat database, IMGT® (the international immunogenetics information system), Protein Data Bank (PDB), V BASE, or others known in the art.

In any of the preceding embodiments, the library may include from about 2 binding polypeptides to about $10^{14}$ or more binding polypeptides (e.g., about 2 to about 10, about 2 to about 20, about 2 to about 30, about 2 to about 40, about 2 to about 50, about 2 to about 60, about 2 to about 70, about 2 to about 70, about 2 to about 80, about 2 to about 100, about 2 to about $10^{14}$, about 2 to about $10^{13}$, about 2 to about $10^{12}$, about 2 to about $10^{11}$, about 2 to about $10^{10}$, about 2 to about $10^9$, about 2 to about $10^8$, about 20 to about $10^8$, about 30 to about $10^8$, about 40 to about $10^8$, about 50 to about $10^8$, about 60 to about $10^8$, about 70 to about $10^8$, about 80 to about $10^8$, about 90 to about $10^8$, about 100 to about $10^8$, about 200 to about $10^8$ binding, about 400 to about $10^8$, about 600 to about $10^8$, about 800 to about $10^8$, about $10^3$ to about $10^8$, about $10^4$ to about $10^8$, about $10^5$ to about $10^8$, about $10^6$ to about $10^8$, or about $10^7$ to about $10^8$ binding polypeptides). In some instances, the library may include about $10^8$ binding polypeptides.

C. Exemplary Anti-IL-13 Antibodies

The invention provides isolated antibodies that bind to IL-13. In some instances, the anti-IL-13 antibody may include at least one, two, or three HVRs selected from: (a) an HVR-H1 comprising the amino acid sequence of AYSVN (SEQ ID NO: 7); (b) an HVR-H2 comprising the amino acid sequence of MIWGDGKIVYNSALKS (SEQ ID NO: 8); and (c) an HVR-H3 comprising the amino acid sequence of DGYYPYAMDN (SEQ ID NO: 9), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 7-9.

In some instances, the anti-IL-13 antibody may further include one, two, three, or four of the following heavy chain framework regions: (a) an FR-H1 comprising the amino acid sequence of QVTLRQSGPALVKPTQTLTLTCTVSGFSLS (SEQ ID NO: 18), QVTLRESGPALVKPTQTLTLTCTVSGLSLS (SEQ ID NO: 19), QVTLRQSGPALVKPTQTLTLTCTVSGLSLS (SEQ ID NO: 20), or QVTLRESGPALVKPTQTLTLTCTVSGFSLS (SEQ ID NO: 21); (b) an FR-H2 comprising the amino acid sequence of WIRQPPGKALEWLA (SEQ ID NO: 22); (c) an FR-H3 comprising the amino acid sequence of RLTISKDTSKNQWLTMTNMDPVDTATYYCAG (SEQ ID NO: 23); and (d) an FR-H4 comprising the amino acid sequence of WGQGSLVTVSS (SEQ ID NO: 24).

In some instances, the anti-IL-13 antibody may further include at least one, two, or three HVRs selected from: (a) an HVR-L1 comprising the amino acid sequence of RASKSVDSYGNSFMH (SEQ ID NO: 10); (b) an HVR-L2 comprising the amino acid sequence of LASNLES (SEQ ID NO: 11); and (c) an HVR-L3 comprising the amino acid sequence of QQNNEDPRT (SEQ ID NO: 12), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 10-12.

In some instances, the anti-IL-13 antibody may further include one, two, three, or four of the following light chain framework regions: (a) an FR-L1 comprising the amino acid sequence of DIVLTQSPDSLSVSLGERATINC (SEQ ID NO: 13) or DIVMTQSPDSLSVSLGERATINC (SEQ ID NO: 14); (b) an FR-L2 comprising the amino acid sequence of WYQQKPGQPPKLLIY (SEQ ID NO: 15); (c) an FR-L3 comprising the amino acid sequence of GVPDRFSGSGSGTDFTLTISSLQAEDVAVYYC (SEQ ID NO: 16); and (d) an FR-L4 comprising the amino acid sequence of FGGGTKVEIK (SEQ ID NO: 17).

In some instances, the anti-IL-13 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 2-5: (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 1 or SEQ ID NO: 6; or (c) a VH domain as in (a) and a VL domain as in (b). For example, in some instances, the antibody comprises a VH domain comprising the amino acid sequence of SEQ ID NO: 2 and a VL domain comprising the amino acid sequence of SEQ ID NO: 6. In some instances, the antibody comprises a VH domain comprising the amino acid sequence of SEQ ID NO: 3 and a VL domain comprising the amino acid sequence of SEQ ID NO: 6. In some instances, the antibody comprises a VH domain comprising the amino acid sequence of SEQ ID NO: 3 and a VL domain comprising the amino acid sequence of SEQ ID NO: 6. In some instances, the antibody comprises a VH domain comprising the amino acid sequence of SEQ ID NO: 4 and a VL domain comprising the amino acid sequence of SEQ ID NO: 6. In some instances, the antibody comprises a VH domain comprising the amino acid sequence of SEQ ID NO: 5 and a VL domain comprising the amino acid sequence of SEQ ID NO: 1. In some instances, the antibody comprises a VH domain comprising the amino acid sequence of SEQ ID NO: 4 and a VL domain comprising the amino acid sequence of SEQ ID NO: 1. In some instances, the antibody comprises a VH domain comprising the amino acid sequence of SEQ ID NO: 3 and a VL domain comprising the amino acid sequence of SEQ ID NO: 1. In some instances, the antibody comprises a VH domain comprising the amino acid sequence of SEQ ID NO: 2 and a VL domain comprising the amino acid sequence of SEQ ID NO: 1.

In a further aspect of the invention, an anti-IL-13 antibody according to any of the above embodiments is a monoclonal antibody, including a chimeric, humanized, or human antibody. In one embodiment, an anti-IL-13 antibody is an antibody fragment, e.g., a Fv, Fab, Fab', scFv, diabody, or F(ab')$_2$ fragment. In another embodiment, the antibody is a full length antibody, e.g., an intact IgG1 antibody, an intact IgG4 antibody, or other antibody class or isotype as defined herein. In another embodiment, the antibody is a half-antibody, for instance, a knob-into-hole half-antibody. See, for example, U.S. Pat. No. 5,731,168 for a description of knob-into-hole technology.

In a further aspect, an anti-IL-13 antibody according to any of the above embodiments may incorporate any of the features, singly or in combination, as described in Sections 1-7 below:

1. Antibody Affinity

In certain embodiments, an antibody provided herein has a dissociation constant ($K_D$) of ≤1 μM, ≤100 nM, ≤10 nM, ≤1 nM, ≤0.1 nM, ≤0.01 nM, ≤1 pM, or ≤0.1 pM (e.g., $10^{-6}$ M or less, e.g., from $10^{-6}$ M to $10^{-9}$ M or less, e.g., from $10^{-9}$ M to $10^{-13}$ M or less).

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293:865-881, 1999). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN®-20) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/l (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in phosphate buffered saline (PBS) with 0.05% polysorbate 20 (TWEEN®-20) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al. (*J. Mol. Biol.* 293: 865-881, 1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134, 2003; and Hollinger et al. *Proc. Natl. Acad. Sci. USA* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (see. e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA,* 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:1619-1633, 2008, and are further described, e.g., in Riechmann et al. *Nature* 332:323-329, 1988; Queen et al. *Proc. Natl. Acad. Sci. USA* 86:10029-10033, 1989; U.S. Pat. Nos. 5,821,337, 7,527,791, 6,982,321, and 7,087,409; Kashmiri et al. *Methods* 36:25-34, 2005 (describing specificity determining region (SDR) grafting); Padlan, *Mol. Immunol.* 28:489-498, 1991 (describing "resurfacing"); Dall'Acqua et al. *Methods* 36:43-60, 2005 (describing "FR shuffling"); and Osbourn et al. *Methods* 36:61-68, 2005 and Klimka et al. *Br. J. Cancer,* 83:252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Natl. Acad. Sci. USA,* 89:4285, 1992; and Presta et al. *J. Immunol.,* 151:2623, 1993); human mature (somatically mutated) framework regions or human germline framework regions (see, e.g., Almagro et al. *Front. Biosci.* 13:1619-1633, 2008); and framework regions derived from screening FR libraries (see, e.g., Baca et al. *J. Biol. Chem.* 272:10678-10684, 1997 and Rosok et al. *J. Biol. Chem.* 271:22611-22618, 1996).

4. Human Antibodies

In certain embodiments, an antibody provided herein is a human antibody. Human antibodies can be produced using various techniques known in the art. Human antibodies are described generally in van Dijk et al. *Curr. Opin. Phannacol.* 5:368-74, 2001 and Lonberg, *Curr. Opin. Immunol.* 20:450-459, 2008.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125, 2005. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001, 1984; Brodeur et al. *Monoclonal Antibody Production Techniques and Applications*, pp. 51-63 (Marcel Dekker, Inc., New York, 1987); and Boerner et al. *J. Immunol.* 147: 86, 1991). Human antibodies generated via human B-cell hybridoma technology are also described in Li et al. *Proc. Natl. Acad. Sci. USA,* 103:3557-3562, 2006. Additional methods include those described, for example, in U.S. Pat. No. 7,189,826 (describing production of monoclonal human IgM antibodies from hybridoma cell lines) and Ni, *Xiandai Mianyixue,* 26(4):265-268, 2006 (describing human-human hybridomas). Human hybridoma technology (Trioma technology) is also described in Vollmers et al. *Histology and Histopathology* 20(3):927-937, 2005 and Vollmers et al. *Methods and Findings in Experimental and Clinical Pharmacology* 27(3):185-91, 2005.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al. *Nature* 348:552-554, 1990; Clackson et al. *Nature* 352: 624-628, 1991; Marks et al. *J. Mol. Biol.* 222: 581-597, 1992; Marks et al. in *Methods in Molecular Biology* 248:161-175 (Lo, ed., Human Press, Totowa, N.J., 2003); Sidhu et al. *J. Mol. Biol.* 338(2): 299-310, 2004; Lee et al. *J. Mol. Biol.* 340(5): 1073-1093, 2004; Fellouse, *Proc. Natl. Acad. Sci. USA* 101(34):12467-12472, 2004; and Lee et al. *J. Immunol. Methods* 284(1-2): 119-132, 2004.

In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.*, 12: 433-455, 1994. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. *EMBO J.* 12: 725-734, 1993. Finally, naive libraries can also be made synthetically by cloning unrearranged V-gene segments from stern cells, and using PCR primers containing random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, for example, a bispecific antibody. Multispecific antibodies are monoclonal antibodies that have binding specificities for at least two different sites. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein et al. *Nature* 305: 537, 1983; WO 93/08829; and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules WO 2009/089004A1); cross-linking two or more antibodies or fragments (see, e.g., U.S. Pat. No. 4,676,980, and Brennan et al. *Science*, 229: 81, 1985); using leucine zippers to produce bispecific antibodies (see, e.g., Kostelny et al. *J. Immunol.*, 148(5):1547-1553, 1992); using "diabody" technology for making bispecific antibody fragments (see, e.g., Hollinger et al. *Proc. Natl. Acad. Sci. USA* 90:6444-6448, 1993); and using single-chain Fv (scFv) dimers (see, e.g. Gruber et al. *J. Immunol* 152:5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g., US 2006/0025576A1).

The antibody or fragment herein also includes a "Dual Acting Fab" or "DAF" comprising an antigen binding site that binds to IL-13 or VEGF as well as another, different antigen (see, e.g., US 2008/0069820).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding, expression, and/or stability.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |

TABLE 1-continued

| Original Residue | Exemplary Substitutions | Preferred Substitutions |
| --- | --- | --- |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln:
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196, 2008), and/or residues that contact antigen, with the resulting variant VH or VL being tested for binding affinity. Affinity maturation by constructing and reselecting from secondary libraries has been described, e.g., in Hoogenboorn et al. in *Methods in Molecular Biology* 178:1-37 (O'Brien et al. ed., Human Press, Totowa, N.J., 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science* 244:1081-1085, 1989, In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32, 1997. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. 2003/0157108 and 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al. *J. Mol. Biol.* 336:1239-1249, 2004; Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249:533-545, 1986; US 2003/0157108; and WO 2004/056312 A1 especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4):680-688, 2006; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3, or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch et al. *Annu. Rev. Immunol.* 9:457-492, 1991. Non-limiting examples of in vitro assays to assess ADCC activity of a molecule of interest is described in U.S. Pat. No. 5,500,362 (see, e.g. Hellstrom et al. *Proc. Natl. Acad. Sci. USA* 83:7059-7063, 1986 and Hellstrom et al. *Proc. Natl. Acad. Sci. USA* 82:1499-1502, 1985; U.S. Pat. No. 5,821,337 (see Bruggernann et al. *J. Exp. Med.* 166; 1351-1361, 1987). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al. *Proc. Natl. Acad. Sci. USA* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods* 202:163, 1996; Cragg et al. *Blood* 101:1045-1052, 2003; and Cragg et al. *Blood* 103:2738-2743, 2004). FcRn binding and in vivo clearance/half life determinations can also be performed using methods known in the art (see, e.g., Petkova et al. *Intl. Immunol.* 18(12):1759-1769, 2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312; and Shields et al. *J. Biol. Chem.* 9(2): 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117:587, 1976 and Kim et al. *J. Immunol.* 24:249, 1994), are described in US2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan et al. *Nature* 322:738-40, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, for example, "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

D. Recombinant Methods and Compositions

Antibodies may be produced using recombinant methods and compositions, for example, as described in U.S. Pat. No. 4,816,567. In one embodiment, isolated nucleic acid encoding an anti-IL-13 antibody described herein is provided. In another embodiment, isolated nucleic acid encoding an anti-VEGF antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell, 293 cell, or lymphoid cell (e.g., Y0, NS0, Sp20 cell). In one embodiment, a method of making an anti-IL-13 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-IL-13 antibody or an anti-VEGF antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. (See also Charlton Methods in Molecular Biology, Vol. 248 (B.K.C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross *Nat. Biotech.* 22:1409-1414, 2004 and Li et al. *Nat. Biotech.* 24:210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59, 1977); baby hamster kidney cells (BHK); mouse sertoli cells (TM4 cells as described, e.g., in *Mather Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68, 1982; MRC 5 cells; and FS4 cells. Other useful mammalian host cell lines include Chinese hamster ovary (CHO) cells, including DHFR⁻ CHO cells (Urlaub et al. *Proc. Natl. Acad. Sci. USA* 77:4216, 1980); and myeloma cell lines such as Y0, NS0 and Sp2/0. For a review of certain mammalian host cell lines suitable for antibody production, see, e.g., Yazaki et al. *Methods in Molecular Biology, Vol.* 248 (B. K. C. Lo, ed., Humana Press, Totowa, N.J.), pp. 255-268, 2003.

E. Assays

Any of the antibodies described herein (e.g., anti-IL-13 antibodies or anti-VEGF antibodies) may be identified, screened for, or characterized for their physical/chemical properties and/or biological activities by various assays known in the art.

1. Binding Assays and Other Assays

In one aspect, any of the antibodies described herein (e.g., an anti-IL-13 antibody or an anti-VEGF antibody) is tested for its antigen-binding activity, for example, by known methods such as ELISA, Western blot, etc.

In another aspect, competition assays may be used to identify an antibody that competes with an anti-IL-13 antibody of the invention for binding to IL-13. In another aspect, competition assays may be used to identify an antibody that competes with an anti-VEGF antibody described herein for binding to VEGF. In certain embodiments, such a competing antibody binds to the same epitope (e.g., a linear or a conformational epitope) that is bound by an anti-IL-13 antibody of the invention. In certain embodiments, such a competing antibody binds to the same epitope (e.g., a linear or a conformational epitope) that is bound by an anti-VEGF antibody described herein. Detailed exemplary methods for mapping an epitope to which an antibody binds are provided in Morris "Epitope Mapping Protocols," in *Methods in Molecular Biology Vol.* 66 (Humana Press, Totowa, N.J.), 1996.

In an exemplary competition assay, immobilized IL-13 is incubated in a solution comprising a first labeled antibody that binds to IL-13 and a second unlabeled antibody that is being tested for its ability to compete with the first antibody for binding to IL-13. The second antibody may be present in a hybridoma supernatant. As a control, immobilized IL-13 is incubated in a solution comprising the first labeled antibody but not the second unlabeled antibody. After incubation under conditions permissive for binding of the first antibody to IL-13, excess unbound antibody is removed, and the amount of label associated with immobilized IL-13 is measured. If the amount of label associated with immobilized IL-13 is substantially reduced in the test sample relative to the control sample, then that indicates that the second antibody is competing with the first antibody for binding to IL-13. See Harlow et al. *Antibodies: A Laboratory Manual* Ch. 14 (Cold Spring Harbor Laboratory, Cold Spring Harbor, N.Y.), 1988.

In another exemplary competition assay, immobilized VEGF is incubated in a solution comprising a first labeled antibody that binds to VEGF and a second unlabeled antibody that is being tested for its ability to compete with the first antibody for binding to VEGF. The second antibody may be present in a hybridoma supernatant. As a control, immobilized VEGF is incubated in a solution comprising the first labeled antibody but not the second unlabeled antibody. After incubation under conditions permissive for binding of the first antibody to VEGF, excess unbound antibody is removed, and the amount of label associated with immobilized VEGF is measured. If the amount of label associated with immobilized VEGF is substantially reduced in the test sample relative to the control sample, then that indicates that the second antibody is competing with the first antibody for binding to VEGF.

2. Activity Assays

In one aspect, assays are provided for identifying anti-IL-13 antibodies thereof having biological activity. Biological activity may include, for example, binding to IL-13 (e.g., IL-13 in the blood stream), or a peptide fragment thereof, either in vivo, in vitro (e.g., displayed in the periplasm of a bacterium), or ex vivo. In other embodiments, biological activity may include blocking or neutralizing IL-13, or preventing IL-13 from binding to a ligand, for example, a receptor (e.g., interleukin-13 receptor). Antibodies having such biological activity in vivo and/or in vitro are also provided. In certain embodiments, an antibody of the invention is tested for such biological activity.

In another aspect, assays are provided for identifying anti-VEGF antibodies thereof having biological activity. Biological activity may include, for example, binding to VEGF (e.g., VEGF in the blood stream), or a peptide fragment thereof, either in vivo, in vitro (e.g., displayed in the periplasm of a bacterium), or ex vivo. In other embodiments, biological activity may include blocking or neutralizing VEGF, or preventing VEGF from binding to a ligand, for example, a receptor (e.g., Tie2, KDR, and/or Flt-1). Antibodies having such biological activity in vivo and/or in vitro are also provided. In certain embodiments, an antibody of the invention is tested for such biological activity.

F. Immunoconjugates

The invention also provides immunoconjugates comprising any of the antibodies described herein (e.g., anti-IL-13 antibodies or anti-VEGF antibodies) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064, and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such as daunomycin or doxorubicin (see Kratz et al. *Current Med. Chem.* 13:477-523, 2006; Jeffrey et al. *Bioorganic & Med. Chem. Letters* 16:358-362, 2006; Torgov et al. *Bioconj. Chem.* 16:717-721, 2005; Nagy et al. *Proc. Natl. Acad. Sci. USA* 97:829-834, 2000; Dubowchik et al. *Bioorg. & Med. Chem. Letters* 12:1529-1532, 2002; King et al, *J. Med. Chem.* 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates.

Examples include $At^{211}$, $I^{131}$, $I^{125}$, $Y^{90}$, $Re^{185}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example technetium-99m (tc99m) or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science* 238:1098, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (see, e.g., Chari et al. *Cancer Res.* 52:127-131, 1992; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfa-EMCS, sulfo-GMBS, sulfo-KMUS, sulfo-MBS, sulfo-SIAB, sulfa-SMCC, and sulfa-SMPB, and SVSB (succinimidyl-(4-vinylsulfone)benzoate) which are commercially available (e.g., from Pierce Biotechnology, Inc., Rockford, Ill., U.S.A.).

G. Methods and Compositions for Diagnostics and Detection

In certain embodiments, any of the anti-IL-13 antibodies provided herein is useful for detecting the presence of IL-13 in a biological sample. The term "detecting" as used herein encompasses quantitative or qualitative detection. In certain embodiments, a biological sample comprises a cell or tissue, such as T helper type 2 (Th2) cells, mast cells, B cells, monocytes, macrophages, and non-hematopoietic cells, including smooth muscle cells, epithelial cells, endothelial cells, or fibroblast cells.

In one embodiment, an anti-IL-13 antibody for use in a method of diagnosis or detection is provided. In a further aspect, a method of detecting the presence of IL-13 in a biological sample is provided. In certain embodiments, the method comprises contacting the biological sample with an anti-IL-13 antibody as described herein under conditions permissive for binding of the anti-IL-13 antibody to IL-13, and detecting whether a complex is formed between the anti-IL-13 antibody and IL-13. Such method may be an in vitro or in vivo method. In one embodiment, an anti-IL-13 antibody is used to select subjects eligible for therapy with an anti-IL-13 antibody, for example, where IL-13 is a biomarker for selection of patients.

Exemplary disorders that may be diagnosed using an anti-IL-13 of the invention include IL-13-mediated disorders or IgE-mediated disorders. In some instances, the IL-13-mediated disorder is, for example, allergy, asthma (e.g., allergic asthma, atopic asthma, severe asthma, and non-allergic (intrinsic) asthma), autoimmune disease (e.g., psoriasis, rheumatoid arthritis, juvenile chronic arthritis, and inflammatory bowel disease (e.g., ulcerative colitis and Crohn's disease), inflammatory disease, allergic rhinitis (including seasonal allergic rhinitis), atopic dermatitis, allergic conjunctivitis, eczema, urticaria, food allergies, food hypersensitivity, celiac disease, immune-mediated skin diseases (e.g., bullous skin diseases, erythema multiform, contact dermatitis), scleroderma, fibrosis, hepatic fibrosis, endomyocardial fibrosis, chronic bronchitis, bronchiectasis, idiopathic interstitial pneumonia, goblet cell metaplasia, lung inflammatory disorders, inflammatory and fibrotic lung diseases (e.g., cystic fibrosis, idiopathic pulmonary fibrosis, and chronic obstructive pulmonary disease (COPD)), gluten-sensitive enteropathy, Whipple's disease, immunologic diseases of the lung (e.g., eosinophilic pneumonia (including chronic eosinophilic pneumonia), idiopathic pulmonary fibrosis, allergic bronchopulmonary aspergillosis, and hypersensitivity pneumonitis), Churg-Strauss syndrome (periarteritis nodosa plus atopy), eosinophilic myalgia syndrome, hypereosinophilic syndrome, edematous reactions (e.g., episodic angioderna, eosinophilic esophagitis, eosinophilic gastritis, eosinophilic gastroenteritis, eosinophilic enteritis and eosinophilic colitis), nasal micropolyposis and polyposis, RSV infection, uveitis, osteoporosis, and malignancies, including cancers or tumors associated with aberrant expression of IL-13 (e.g., Hodgkin's lymphoma). In some embodiments, the disorder is allergic asthma, non-allergic (intrinsic) asthma, allergic rhinitis, atopic dermatitis, allergic conjunctivitis, eczema, urticaria, food allergies, chronic obstructive pulmonary disease, ulcerative colitis, RSV infection, uveitis, scleroderma, or osteoporosis. In some instances, the IgE-mediated disorder is bronchial asthma, allergic rhinitis, allergic dermatitis, urticaria, anaphylaxis, or atopic dermatitis.

In certain embodiments, the invention provides a method of diagnosing a disorder associated with VEGF (e.g., increased expression of VEGF). In certain embodiments, the method comprises contacting a test cell with an anti-VEGF antibody as described herein; determining the level of expression (either quantitatively or qualitatively) of VEGF by the test cell by detecting binding of the anti-VEGF antibody to VEGF; and comparing the level of expression of VEGF by the test cell with the level of expression of VEGF by a control cell (e.g., a normal cell of the same tissue origin as the test cell or a cell that expresses VEGF at levels comparable to such a normal cell), wherein a higher level of expression of VEGF by the test cell as compared to the control cell indicates the presence of a disorder associated with increased expression of VEGF. In certain embodiments, the test cell is obtained from an individual suspected of having a disorder associated with increased expression of VEGF. In certain embodiments, the disorder is a tumor, cancer, and/or cell proliferative disorder.

Exemplary disorders that may be diagnosed using an anti-VEGF antibody described herein include, but not limited to, squamous cell cancer, small-cell lung cancer, non-small cell lung cancer, adenocarcinoma of the lung, squamous carcinoma of the lung, cancer of the peritoneum, hepatocellular cancer, gastric cancer, gastrointestinal cancer, gastrointestinal stromal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, melanoma, superficial spreading melanoma, lentigo maligna melanoma, acral lentiginous melanomas, nodular melanomas, B-cell lymphoma, chronic lymphocytic leukemia (CLL); acute lymphoblastic leukemia (ALL); Hairy cell leukemia; chronic myeloblastic leukemia; post-transplant lymphoproliferative disorder (PTLD), abnormal vascular proliferation associated with phakomatoses, edema associated with brain tumors, and Meigs' syndrome.

In another aspect, the invention provides a method of detecting the presence of VEGF in a biological sample. In certain embodiments, the method comprises contacting the biological sample with an anti-VEGF antibody under conditions permissive for binding of the anti-VEGF antibody to VEGF, and detecting whether a complex is formed between the anti-VEGF antibody and VEGF.

Anti-VEGF antibodies can be used for the detection of VEGF in any one of a number of well known detection assay methods. For example, a biological sample may be assayed for VEGF by obtaining the sample from a desired source, admixing the sample with anti-VEGF antibody to allow the antibody to form antibody/VEGF complex with any VEGF present in the mixture, and detecting any antibody/VEGF complex present in the mixture. The biological sample may be prepared for assay by methods known in the art which are suitable for the particular sample. The methods of admixing the sample with antibodies and the methods of detecting antibody/VEGF complex are chosen according to the type of assay used.

Labeled anti-IL-13 or anti-VEGF antibodies are described herein. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

H. Pharmaceutical Formulations

Pharmaceutical formulations of any of the antibodies described herein (e.g., anti-IL-13 or anti-VEGF antibodies) are prepared by mixing such antibody having the desired degree of purity with one or more optional pharmaceutically acceptable carriers (see, e.g., *Remington's Pharmaceutical Sciences* 16th edition, Osol, A. Ed., 1980), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carrier's herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The composition herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile. Sterility may be readily accomplished, for example, by filtration through sterile filtration membranes.

I. Therapeutic Methods and Compositions

Any of the antibodies described herein (e.g., anti-IL-13 or anti-VEGF antibodies) may be used in therapeutic methods.

In one aspect, an anti-IL-13 antibody for use as a medicament is provided. In further aspects, an anti-IL-13 antibody for use in treating IL-13-mediated disorders is provided. In certain embodiments, an anti-IL-13 antibody for use in a method of treatment is provided. In certain embodiments, the invention provides an anti-IL-13 antibody for use in a method of treating an individual having an IL-13-mediated disorder comprising administering to the individual an effective amount of the anti-IL-13 antibody. In one such embodiment, the method further comprises administering to the individual an effective amount of at least one additional therapeutic agent, for example, as described below. An "individual" according to any of the above embodiments is preferably a human.

In a further aspect, the invention provides for the use of an anti-IL-13 antibody in the manufacture or preparation of a medicament. In one embodiment, the medicament is for treatment of an IL-13-mediated disorder. In a further embodiment, the medicament is for use in a method of treating IL-13-mediated disorder comprising administering to an individual having IL-13-mediated disorder an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating an IL-13-mediated disorder, including, for example allergy, asthma (e.g., allergic asthma, atopic asthma, severe asthma, and non-allergic (intrinsic) asthma), autoimmune disease (e.g., psoriasis, rheumatoid arthritis, juvenile chronic arthritis, and inflammatory bowel disease (e.g., ulcerative colitis and Crohn's disease), inflammatory disease, allergic rhinitis (including seasonal allergic rhinitis), atopic dermatitis, allergic conjunctivitis, eczema, urticaria, food allergies, food hypersensitivity, celiac disease, immune-mediated skin diseases (e.g., bullous skin diseases, erythema multiform, contact dermatitis), scleroderma, fibrosis, hepatic fibrosis, endomyocardial fibrosis, chronic bronchitis, bronchiectasis, idiopathic interstitial pneumonia, goblet cell metaplasia, lung inflammatory disorders, inflammatory and fibrotic lung diseases (e.g., cystic fibrosis, idiopathic pulmonary fibrosis, and chronic obstructive pulmonary disease (COPD)), gluten-sensitive enteropathy, Whipple's disease, immunologic diseases of the lung (e.g., eosinophilic pneumonia (including chronic eosinophilic pneumonia), idiopathic pulmonary fibrosis, allergic bronchopulmonary aspergillosis, and hypersensitivity pneumonitis), Churg-Strauss syndrome (periarteritis nodosa plus atopy), eosinophilic myalgia syndrome, hypereosinophilic syndrome, edematous reactions (e.g., episodic angioderma, eosinophilic esophagitis, eosinophilic gastritis, eosinophilic gastroenteritis, eosinophilic enteritis and eosinophilic colitis), nasal micropolyposis and polyposis, RSV infection, uveitis, osteoporosis, and malignancies, including cancers or tumors associated with aberrant expression of IL-13 (e.g., Hodgkin's lymphoma). In some embodiments, the disorder is allergic asthma, non-allergic (intrinsic) asthma, allergic rhinitis, atopic dermatitis, allergic conjunctivitis, eczema, urticaria, food allergies, chronic obstructive pulmonary disease, ulcerative colitis, RSV infection, uveitis, scleroderma, or osteoporosis. In some embodiments, the method further comprises administering to the individual an effective amount of at least one additional therapeutic agent, as described below. An "individual" according to any of the above embodiments may be a human.

In some instances, the invention provides a method of treating a patient suffering from asthmatic symptoms comprising administering an amount of the any of the anti-IL-13 antibodies of the invention effective to reduce the asthmatic symptoms.

In some instances, the invention provides a method for inhibiting IgE antibody production in a patient comprising administering to the patient an IgE antibody production inhibiting effective amount of any of the anti-IL-13 antibodies of the invention. In some instances, the inhibition of IgE antibody production is intended to prevent bronchial asthma, to prevent allergic rhinitis, to prevent allergic dermatitis, to treat bronchial asthma, to treat allergic rhinitis, to treat urticaria, to prevent anaphylaxis, or to treat atopic dermatitis.

In other instances, the invention provides a method of treating an IgE-mediated disorder in a patient, comprising administering to the patient an effective amount of an anti-IL-13 antibody of the invention. In some instances, the IgE-mediated disorder is bronchial asthma, allergic rhinitis, allergic dermatitis, urticaria, anaphylaxis, or atopic dermatitis.

In a further aspect, the invention provides pharmaceutical formulations comprising any of the anti-IL-13 antibodies provided herein, e.g., for use in any of the above therapeutic methods. In one embodiment, a pharmaceutical formulation comprises any of the anti-IL-13 antibodies provided herein and a pharmaceutically acceptable carrier. In another embodiment, a pharmaceutical formulation comprises any of the anti-IL-13 antibodies provided herein and at least one additional therapeutic agent, for example, as described below.

Anti-IL-13 antibodies of the invention can be used either alone or in combination with other agents in a therapy. For example, anti-IL-13 antibodies of the invention may be advantageously utilized in combination with other monoclonal or chimeric antibodies, or with lymphokines or hernatopoietic growth factors (such as, e.g., IL-2, IL-3, IL-5, IL-7, IFN), for example, which serve to increase the number or activity of effector cells which interact with the antibodies. The antibodies of the invention may be administered alone or in combination with other types of treatments, such as immunotherapy, bronchodilators, anti-IgE molecules, anti-histamines, or anti-leukotrienes.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-IL-13 antibody and administration of an additional therapeutic agent occur within about one month, or within about one, two or three weeks, or within about one, two, three, four, five, or six days, of each other. Antibodies of the invention can also be used in combination with radiation therapy.

In one aspect, an anti-VEGF antibody for use as a medicament is described herein. In further aspects, an anti-VEGF antibody for use in treating a disorder associated with pathological angiogenesis is described herein. In certain embodiments, an anti-VEGF antibody for use in a method of treatment is described herein. In certain embodiments, an anti-VEGF antibody for use in a method of treating an individual having a disorder associated with pathological angiogenesis comprising administering to the individual an effective amount of the anti-VEGF antibody is described herein. In one such embodiment, the method further comprises administering to the individual an effective amount of at least one additional therapeutic agent, for example, as described below. An "individual" according to any of the above embodiments is preferably a human.

In a further aspect, the use of an anti-VEGF antibody in the manufacture or preparation of a medicament is described herein. In one embodiment, the medicament is for treatment of a disorder associated with pathological angiogenesis. In a further embodiment, the medicament is for use in a method of treating a disorder associated with pathological angiogenesis comprising administering to an individual having a disorder associated with pathological angiogenesis an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides pharmaceutical formulations comprising any of the anti-VEGF antibodies described herein, e.g., for use in any of the above therapeutic methods. In one embodiment, a pharmaceutical formulation comprises any of the anti-VEGF antibodies described herein and a pharmaceutically acceptable carrier. In another embodiment, a pharmaceutical formulation comprises any of the anti-VEGF antibodies described herein and at least one additional therapeutic agent, for example, as described below.

In another aspect, the invention provides a method of reducing or inhibiting angiogenesis, for example, in a subject having a disorder associated with pathological angiogenesis, comprising administering to the subject an effective amount of an anti-VEGF antibody described herein thereby reducing or inhibiting angiogenesis in the subject. In certain embodiments, the disorder associated with pathological angiogenesis is non-neoplastic. In certain embodiments, the disorder associated with pathological angiogenesis is cancer. In one such embodiment, the method further comprises administering to the individual an effective amount of at least one additional agent, for example, as described below.

In another aspect, the invention provides a method of treating a tumor, a cancer, or a cell proliferative disorder, the method comprising administering an effective amount of an anti-VEGF antibody described herein. In one such embodiment, the method further comprises administering to the individual an effective amount of at least one additional agent, for example, as described below.

Anti-VEGF antibodies described herein can be used either alone or in combination with other agents in a therapy. For instance, an anti-VEGF antibody may be co-administered with at least one additional agent. In certain embodiments, an additional agent is a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, a growth-inhibitory agent, an apoptotic agent, anti-tubulin agent, or other agent, such as a epidermal growth factor receptor (EGFR) antagonist (e.g., a tyrosine kinase inhibitor), HER1/EGFR inhibitor (e.g., erlotinib (TARCEVA™), platelet derived growth factor inhibitor (e.g., GLEEVEC™ (Imatinib Mesylate)), a COX-2 inhibitor (e.g., celecoxib), interferon, cytokine, an antibody that binds to a target other than VEGF, or another bioactive or organic chemical agent.

Such combination therapies noted above encompass combined administration (where two or more agents are included in the same or separate compositions), and separate administration, in which case, administration of the antibody of the invention can occur prior to, simultaneously, and/or following, administration of the additional agent or agents. In one embodiment, administration of the anti-VEGF antibody and administration of an additional agent occur within about one month, or within about one, two or three weeks, or within about one, two, three, four, five, or six days, of each other. Anti-VEGF antibodies described herein can also be used in combination with radiation therapy.

An anti-IL-13 antibody or an anti-VEGF antibody described herein (and any additional therapeutic agent) can be administered by any suitable means, including intramuscularly, intravenously, intradermally, percutaneously, intraarterially, intraperitoneally, intralesionally, intracranially, intraarticularly, intraprostatically, intravitreally, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

Antibodies would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg to 10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg, Thus, one or more doses of about 0.5 mg/kg, 2.0 mg/kg, 4.0 mg/kg or 10 mg/kg (or any combination thereof) may be administered to the patient. Such doses may be administered intermittently, e.g. every week, every two weeks, every three weeks, or every four weeks (e.g., such that the patient receives from about two to about twenty, or e.g., about six doses of the antibody). For example, a dose may be administered once per month, (e.g., by subcutaneous injection). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate in place of or in addition to an anti-IL-13 antibody or an anti-VEGF antibody.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

J. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-IL-13 antibody or' an anti-VEGF antibody.

K. Engineered Bacteria

The invention provides engineered bacteria. The bacteria of the invention may be used, for example, in any of the methods of the invention, for example, the methods described above in Section A or in the working Examples.

In one example, the invention provides a bacterium that includes (i) a mutation that allows for diffusion of membrane-impermeant molecules across the outer membrane into the periplasm; and (ii) an expression construct encoding a binding polypeptide.

In some instances, the mutation that allows for diffusion of membrane-impermeant molecules across the outer membrane into the periplasm is in a gene encoding an outer membrane protein and/or a protein that affects lipopolysaccharide (LPS) composition. In some instances, the mutation is in a gene encoding an outer membrane protein, for example, major outer membrane lipoprotein Lpp (Lpp), a porin, or TolC. In some instances, the outer membrane protein is Lpp. In some embodiments, the mutation is in a gene encoding a protein that affects LPS composition, for example, Env proteins (e.g., EnvA, EnvB, and EnvM), RfaD, RfaE, RfaH, RfaRd, TolA, TolB, and TolD.

In some instances, the binding polypeptide may be an antibody. In some instances, the antibody of any of the above methods is a monoclonal antibody, including a chimeric, humanized, or human antibody. In some instances, the antibody is an antibody fragment, e.g., a Fv, Fab, Fab', scFv, diabody, or F(ab')$_2$ fragment. In other instances, the antibody is a full-length antibody, e.g., an intact IgG1 antibody, an intact IgG4 antibody, or other antibody class or isotype as defined herein. In another embodiment, the antibody is a half-antibody, for instance, a knob-into-hole half-antibody. See, for example, U.S. Pat. No. 5,731,168 for a description of knob-into-hole technology. In any of the preceding methods, the antibody may be a therapeutic antibody (e.g., a neutralizing antibody).

In other instances, the binding polypeptide may be an antibody mimetic, for example, an affibody, an affilin, an affimer, an affitin, an alphabody, an anticalin, an avimer, a designed ankyrin repeat protein (DARPin), a fynomer, a Kunitz domain peptide, or a monobody. In other embodiments, the binding polypeptide may be a bacterial protein that localizes to the periplasm. In other embodiments, the binding polypeptide may be a mammalian protein. For example, in some embodiments, the binding polypeptide may be a cell surface receptor, a cytokine, or a growth factor.

For example, the invention provides a bacterium that includes (i) a loss-of-function mutation in a gene encoding major outer membrane lipoprotein Lpp (Lpp); and (ii) an expression construct encoding an antibody. In some instances, the antibody is a full-length antibody. In some instances, the antibody is an IgG antibody. In some instances, the antibody is a half-antibody. In some instances, the antibody is an antibody fragment. In some instances, the antibody fragment is selected from the group consisting of Fab, Fab'-SH, Fv, scFv, and (Fab')$_2$ fragments.

Any of the bacteria described above may include any suitable mutation (e.g., loss of function mutation) in the gene encoding Lpp. Exemplary lpp mutations include, but are not limited to, lpp-1; lpp-21; lpp-3; lpp5508; lpp-6; lpp::Tn5KAN-2; lppD70E, G, or S; lppK75S or T; lppK78R;

1ppR77D or L; 1ppS22D; lppY76C, D, E, G, N, P, or S; lppY76F, H, I, or L; Δlpp, Δlpp-254, and Δlpp-752::kan, or those described herein. Such lpp mutations may be may be acquired from, for example, a repository such as the CGSC (The *Coli* Genetic Stock Center). In other instances, a mutation in the gene encoding Lpp may be made using standard molecular genetics approaches. In some instances, the loss-of-function mutation in a gene encoding Lpp is selected from a point mutation, an insertion mutation, or a deletion mutation. In some instances, the loss-of-function mutation is a deletion mutation.

Any of the bacteria described above may include an inner membrane, a periplasm, and outer membrane. In some instances, the bacterium is a gram-negative bacterium. For example, in some instances, the bacterium is an *E. coli*. Any suitable strain or genetic background of *E. coli* may be used. Commonly used strains and genetic backgrounds of *E. coli* are well known in the art Exemplary *E. coli* strains include, but are not limited to, laboratory strains, such as K-12 and its substrains (e.g., Clifton wild type, W3110, DH5αE, and the like), and *E. coli* B and its substrains (e.g., BL21, BL21(DE3), and the like). In some embodiments, the *E. coli* is derived from strain 62A7. In some embodiments, the *E. coli* is derived from strain 33D3. In some embodiments, the *E. coli* is derived from strain 66C4.

In some instances, any of the preceding bacteria may include a mutation affecting a transcription-regulating gene. In some instances, the transcription-regulating gene is selected from a transcription initiation factor, an anti-sigma factor, an RNA polymerase subunit, or a transcription factor. In some instances, the transcription initiation factor is a sigma factor. In some instances, the sigma factor is selected from the group consisting of RpoD ($\sigma^{70}$), RpoE ($\sigma^{24}$, RpoH ($\sigma^{32}$), RpoS ($\sigma^{38}$), RpoN ($\sigma^{54}$), RpoF ($\sigma^{28}$), and FecI ($\sigma^{19}$). In particular instances, the sigma factor is RpoD ($\sigma^{70}$). In some instances, the mutation affecting the transcription-regulating gene is present on a synthetic plasmid. In other instances, the mutation affecting the transcription-regulating gene is present in the endogenous bacterial genome. In some instances, the mutation affecting the transcription-regulating gene is due to error-prone PCR mutagenesis, chemical mutagenesis, transpositional mutagenesis, or targeted mutagenesis. In some instances, the mutation affecting the transcription-regulating gene is due to error-prone PCR mutagenesis.

In some instances, the invention provides a plurality of any of the preceding bacteria. In some embodiments, the plurality of bacteria may include a library of the invention, for example, any library described herein in Section B, above, or in the working Examples. In some instances, the plurality of bacteria may include a library of nucleic acids, each encoding a mutant of a transcription-regulating gene (e.g., a sigma factor, e.g., RpoD ($\sigma^{70}$)).

Any of the preceding bacteria may have improved expression of the binding polypeptide (e.g., antibody) by at least about 1%, about 5% about 10%, about 20%, about 30%, about 40%, about 50%, about 60%, about 70%, about 80%, about 90%, about 100%, about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, about 40-fold, about 45-fold, about 50-fold, about 100-fold, or more. In some instances, the bacterium may have between a 1- and 10-fold improved expression, between a 1- and 7-fold improved expression, between a 1- and 6-fold improved expression, between a 1- and 5-fold improved expression, between a 1- and 4-fold improved expression, between a 1- and 3-fold improved expression, between a 2- and 10-fold improved expression, between a 2- and 8-fold improved expression, or between a 2- and 6-fold improved expression. In some embodiments, the improvement is relative to the expression level of the binding polypeptide in a wild-type bacterium. In other embodiments, the improvement is relative to the expression level of the binding polypeptide in a mutant bacterium.

III. Examples

The following are examples of methods and compositions of the invention. It is understood that various other embodiments may be practiced, given the general description provided above.

Example 1

Development of a Live-Cell Bacterial Antibody Display System Compatible with Full-Length Polypeptides Methods of live-cell bacterial antibody display were developed that are compatible with full-length binding polypeptides and ligands, for example, full-length antibodies and antigens. To overcome the limitations of previous bacterial display systems, novel ways to deliver the ligand (e.g., the antigen bound by an antibody) past the bacterial outer membrane into the periplasm without substantially compromising the viability of the bacterial cells were developed.

Deletion of the major outer membrane protein (murein lipoprotein, Lpp) renders the outer membrane semi-permeable. EDTA was utilized to further permeabilize the outer membrane (Leive et al. *J. Biol. Chem.* 243: 6384-6391, 1968; Hancock, *Annu. Rev. Microbiol.* 38: 237-264, 1984). The Δlpp genetic background has been used to leak proteins from the periplasmic space into the media to facilitate purification (Kanamori et al. *Gene* 66: 295-300, 1988). However, this genetic background could in principle also be used to allow ligands that are normally excluded by the outer membrane permeability barrier to diffuse into the periplasm.

Figure 1B:
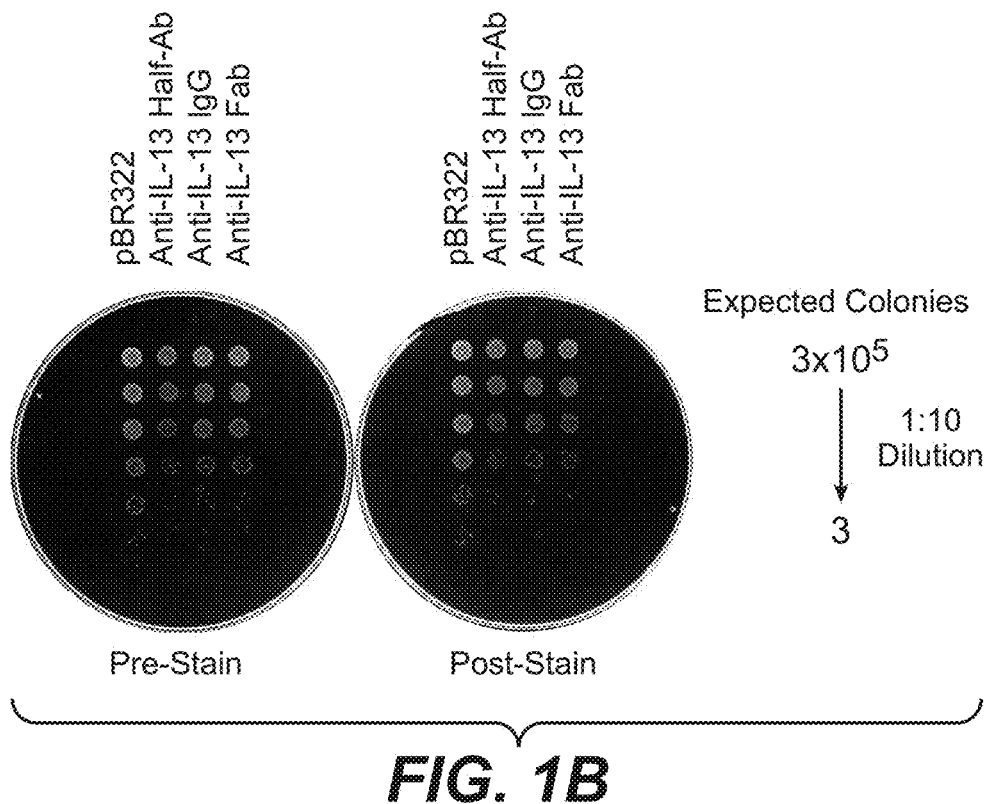
FIG. 1B shows images of bacterial media plates spotted with serial dilutions of cells expressing different anti-IL-13 antibody formats or an empty control vector (pBR322) before ("Pre-Stain") and after ethylenediaminetetraacetic acid (EDTA) treatment, antigen staining, and MgCl$_2$ addition ("Post-Stain"). No substantial difference in viability was observed between the unstained and stained cells.

To demonstrate the functionality of this system, an anti-IL-13 IgG (Spiess et al. *J. Biol. Chem.* 288: 26583-26593, 2013) was expressed in a Δlpp background, and fluorescent microscopy was used to determine whether cells treated with EDTA could bind exogenously-added fluorescently-labeled IL-13 cytokine. Only cells expressing antibody retained antigen (FIG. 1A), indicating that a membrane tether is not required to efficiently retain antibody in the cells. While IL-13 antigen has a molecular weight of ~15 kDa, staining with an anti-Fc F(ab')$_2$ indicates that antigens having a size of at least 100 kDa could efficiently enter and be retained in the periplasm of permeabilized cells. In other experiments, cells were successfully stained with a full-length antibody, indicating that molecules having a size of at least 150 kDa can efficiently enter and be retained in the periplasm of permeabilized cells. However, use of EDTA to permeabilize the cells resulted in decreased cell viability. To overcome the viability decrease, MgCl$_2$ was added after staining with antigen and EDTA, which restored the viability to levels seen before EDTA treatment (FIG. 1B).

Figure 1C:
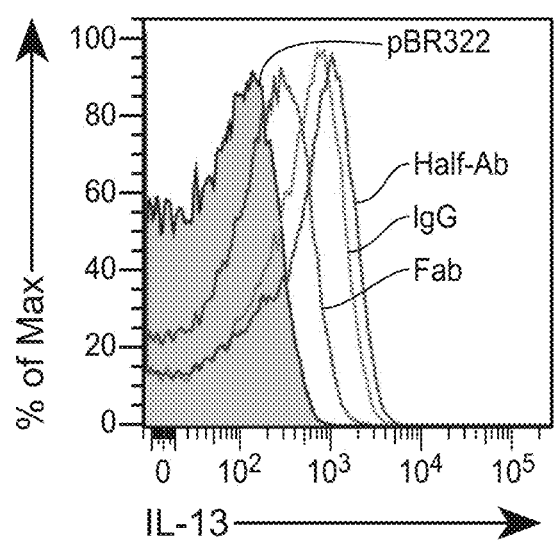
FIG. 1C is a graph showing flow cytometric analysis of cells expressing different formats of an anti-IL-13 antibody (IgG, half-antibody (Half-Ab), and Fab) or control cells transformed with the empty control vector pBR322 (black line, shaded) following staining with fluorescently-labeled IL-13. All formats showed a shift of IL-13 signal above the pBR322 control.

Next, other antibody formats were tested to determine whether they could be efficiently retained in the periplasm to bind antigen. Similar to the full-length antibody, both the Fab and half-antibody formats could be expressed and stained with antigen without impacting viability (FIG. 1B). While empty vector control (pBR322) cells showed autofluorescence by flow cytometry that contributed to a background signal, all tested antibody formats gave an antigen-specific signal above this background that enabled efficient sorting (FIG. 1C). Half-antibodies with knobs-into-holes Fc technology are of interest as they can be used to generate full-length bispecific antibodies (Spiess et al. *Nat. Biotechnol.* 31: 753-758, 2013). For all following display experiments, half-antibody constructs were utilized.

Figure 1D:
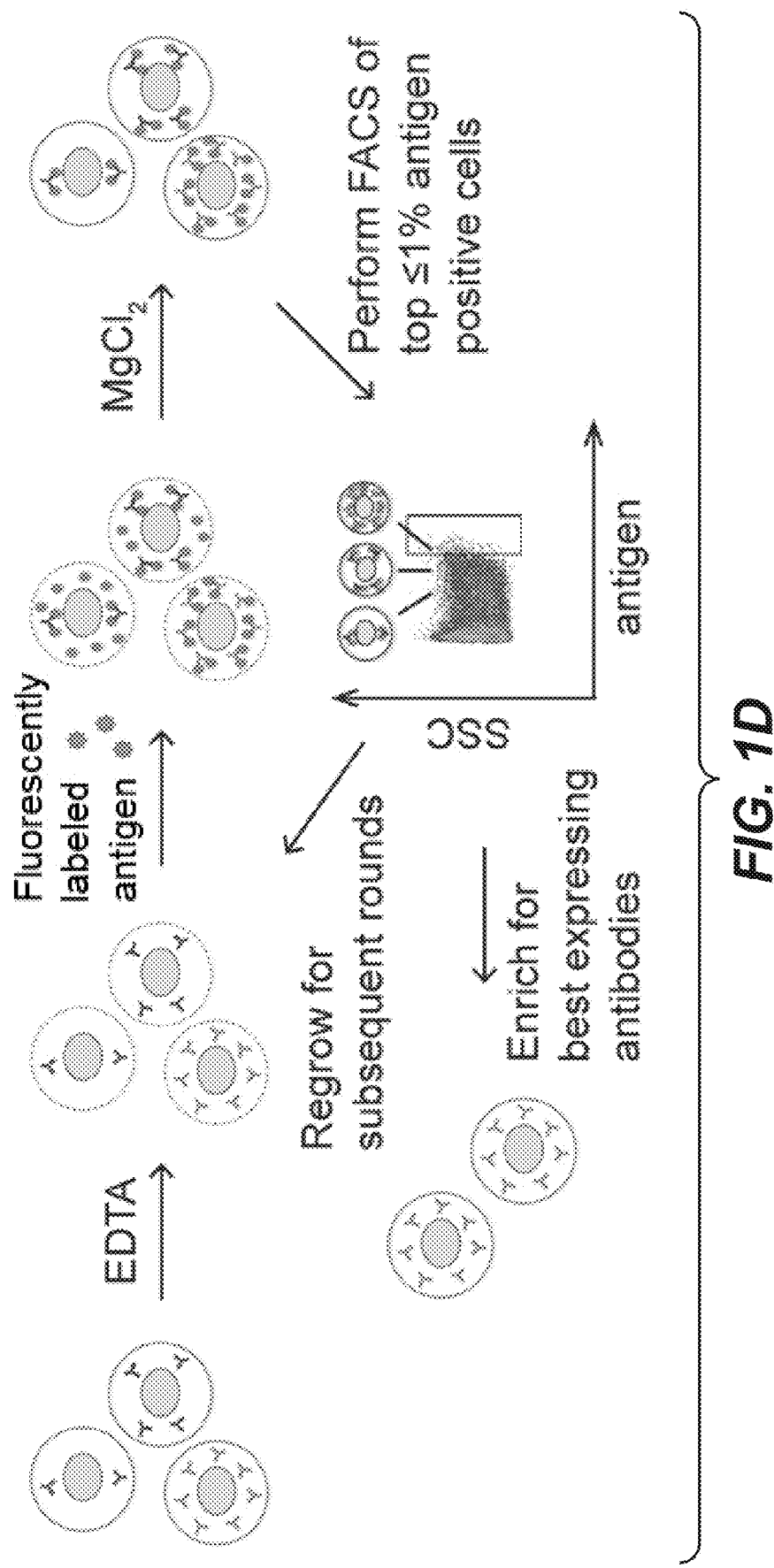
FIG. 1D is a schematic diagram of an exemplary method of the invention. Cells are permeabilized by treatment with EDTA, incubated with fluorescently-labeled antigen, and the integrity of the outer membrane restored by addition of MgCl$_2$. The top ≤1% antigen-positive cells are sorted by flow cytometry and either progress, after regrowth, into a subsequent round for further enrichment or are collected for analysis. SSC, side scatter.
Figure 2A:
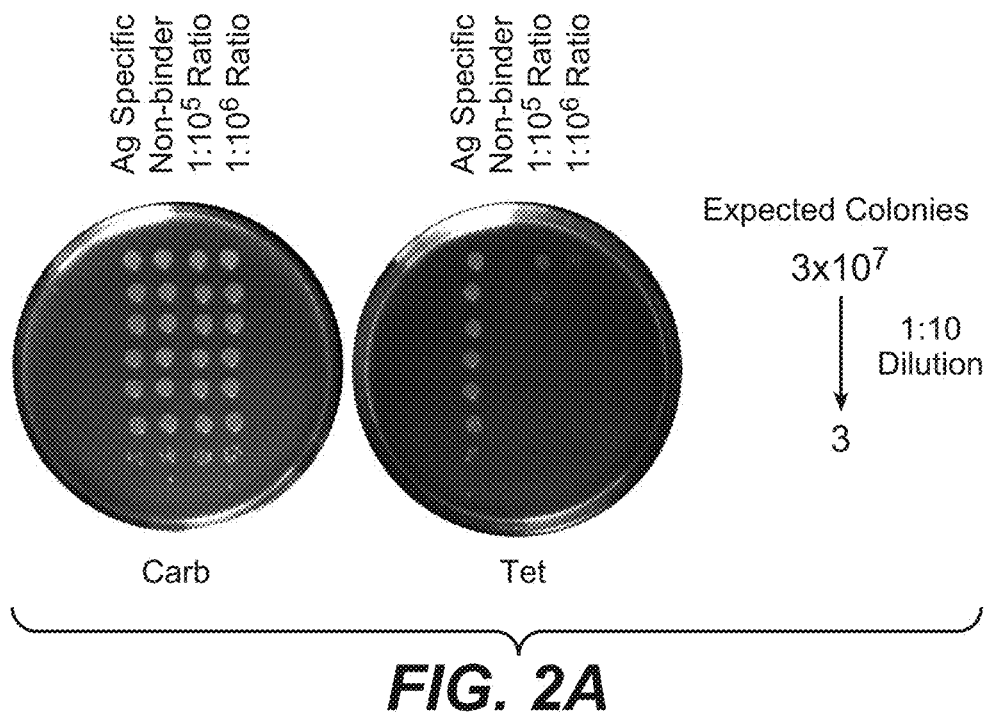
FIG. 2A shows images of bacterial media plates spotted with serial dilutions of bacteria carrying a plasmid encoding an anti-IL-13 antibody that confers carbenicillin (Carb) and tetracycline (Tet) resistance spiked 1:10$^5$ or 1:10$^6$ into bacteria transformed with a plasmid coding for an anti-VEGF antibody conferring carbenicillin resistance. The existence of rare anti-IL-13 expressing bacteria was visualized by plating serial dilutions onto carbenicillin (total bacterial count) and tetracycline (bacteria carrying anti-IL-13 plasmid only) containing plates, confirming the expected ratios.
Figure 2B:
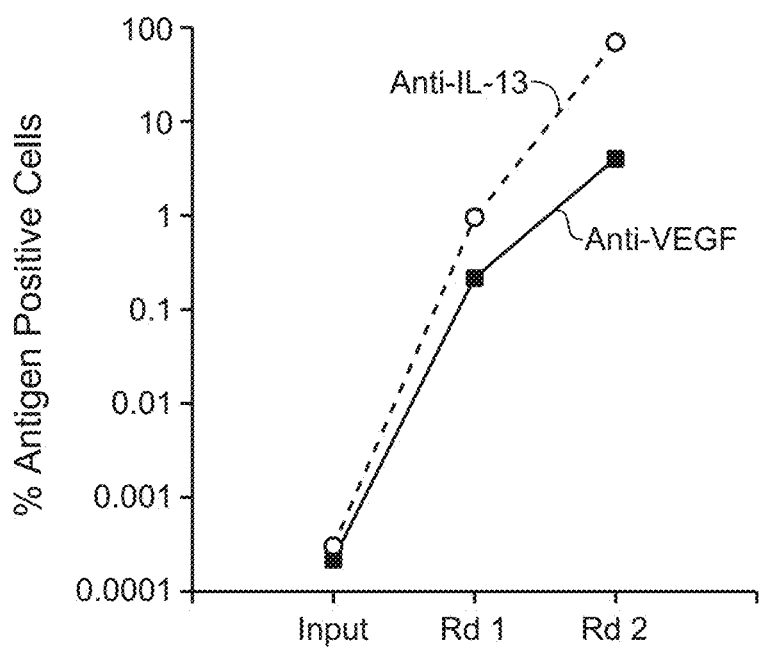
FIG. 2B is a graph showing the percentage of antigen-positive cells after 1 or 2 rounds (Rd) of bacterial antibody display (BAD). Spiked cultures were BAD sorted with ALEXA FLUOR® 647-labeled antigen. Cells displaying an anti-IL-13 (circle) or anti-VEGF-antibody (square) spiked into a pool of cells displaying non-binding antibodies at a ratio of 1:10$^6$ are rapidly enriched over the course of two rounds of BAD sorting.
Figure 2C:
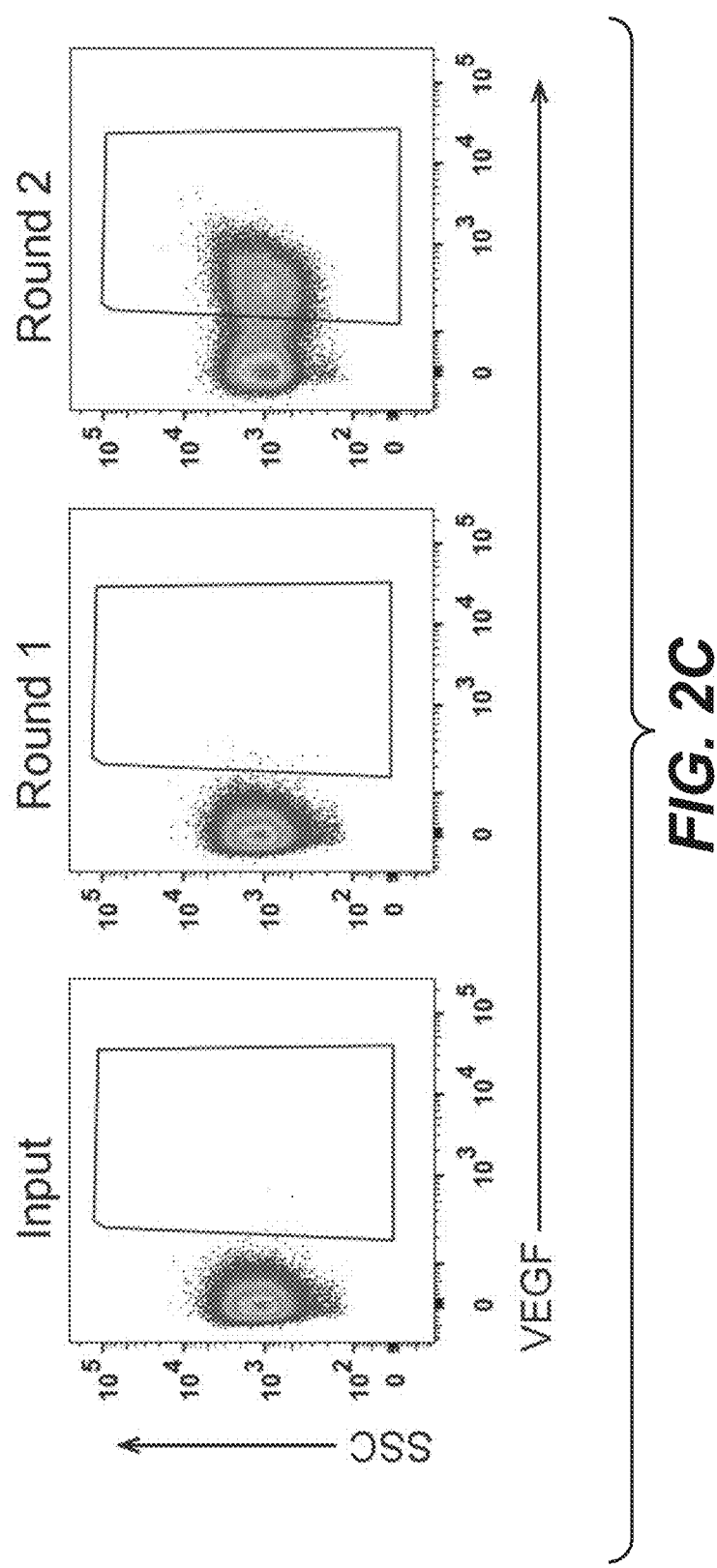
FIG. 2C is a series of graphs showing flow cytometric analysis of the anti-VEGF spiking experiment shown in FIG. 2B. A significant portion of the population binds to VEGF antigen after two rounds of sorting.

As described below, the technology (sometimes referred to herein as Bacterial Antibody Display or "BAD" in a broad and non-limiting sense) overcomes the current limits of bacterial display by delivering full-length antigen into live cells, allowing rapid round-to-round progression using flow cytometry (e.g., FACS™) selection (FIG. 1D). It is to be understood that BAD can be used not only with antibodies but also with any suitable binding polypeptide. In a first step, enrichment of a binding antibody from a pool of non-binders was tested using BAD. Cells expressing an anti-IL-13 antibody were spiked into a pool of cells expressing anti-VEGF antibodies. To track the ratios of each antibody in the mixture, a plasmid conferring only carbenicillin resistance was used to express anti-VEGF, while the plasmid used to express anti-IL-13 confers both carbenicillin and tetracycline resistance. Accuracy of spiking was initially determined by spot plating serial dilutions of the mixed culture at $1:10^5$ and $1:10^6$ ratios on carbenicillin or tetracycline containing plates, which confirmed that the anti-IL-13 antibody was represented in the pool at the anticipated frequency (FIG. 2A). For more accurate quantification of the sorting experiments that followed, larger volumes were plated and colony counts taken to calculate the ratio of anti-IL-13 to anti-VEGF in each sample. Starting with a $1:10^6$ ratio of anti-IL-13:anti-VEGF, two rounds of BAD were performed by sorting for the anti-IL-13-positive cells and achieved a 235,000-fold enrichment (FIG. 2B). To ensure that a separate antigen/antibody pair could be enriched, the converse experiment was performed, resulting in a 19,500-fold enrichment of the binding anti-VEGF antibody after two rounds of FACS™ (FIG. 2B). This enrichment corresponded to a large VEGF-positive shift in the population after the second round of FACS™ (FIG. 2C). These experiments confirmed that binding clones could be rapidly and highly enriched by the BAD system.

Figure 3A:
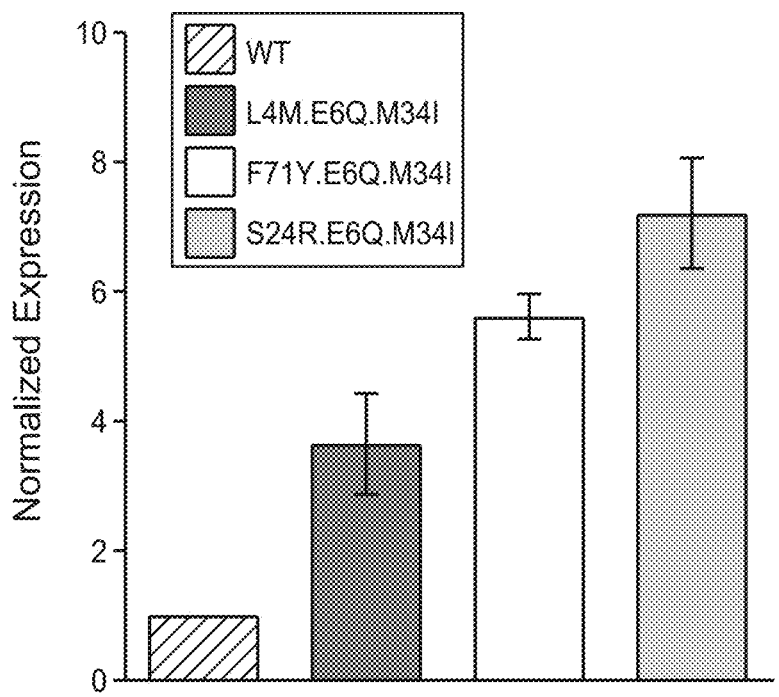
FIG. 3A is a graph showing expression levels of anti-VEGF.2 variants as determined by Western blot. Non-reduced soluble samples were detected with an anti-human Fc antibody and quantified using a LI-COR ODYSSEY® instrument. The signal was normalized to the half-antibody band of anti-VEGF.2 WT (wild-type). n=3 experiments. All variants have increased expression levels compared to WT.
Figure 3B:
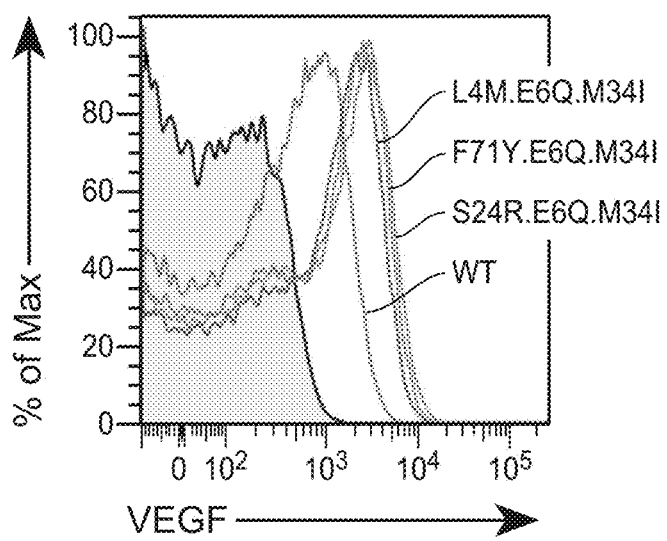
FIG. 3B is a graph showing flow cytometric analysis of individual anti-VEGF.2 variants. Anti-VEGF.2 WT has a higher shift than unstained cells (black, shaded). All variants have higher shifts than WT, and correlate to the expression rankings as determined by Western blot (see FIG. 3A). Anti-VEGF.2 WT, L4M.E6Q.M34I, F71Y.E6Q.M34I, and S24R.E6Q.M34I are indicated.

Next, the BAD system was tested for its ability to enrich for the best expression or folding variants of the same antibody. To test the resolution of the system, a half-antibody based on anti-VEGF.2 antibody along with three variants that have different expression levels were used. The variants included different combinations of light chain (L4M, S24R, F71Y) and heavy chain (E6Q, M34I) mutations. Non-reduced soluble samples were detected with an anti-human Fc antibody by Western blot and expression levels were normalized to anti-VEGF.2 half-antibody wild-type (WT) (FIG. 3A). Anti-VEGF.2 WT had the lowest functional expression, while L4M.E6Q.M34I, F71Y.E6Q.M34I, and S24R.E6Q.M34I had 3.7-, 5.6-, and 7.2-fold increases in expression levels, respectively. To ensure that expression and FACS™ shift were in agreement, BAD was used to determine the individual FACS™ shifts for anti-VEGF.2 WT and variants stained with fluorescently labeled VEGF (FIG. 3B). The FACS™ mean fluorescence intensities ranked in the same order as the expression levels, with L4M.E6Q.M34I, F71Y.E6Q.M34I, and S24R.E6Q.M34I having 1.25+/−0.2, 1.37+/−0.2, and 1.4+/−0.3 fold-increases compared to WT anti-VEGF.2. Thus, these antibodies were good candidates for testing if BAD could select for the best expressing antibodies.

A BAD screen combining anti-VEGF.2 WT with the three variants was performed. Two rounds of FACS™ were performed and the top 1% of VEGF-binding clones was sorted in each round. The FACS™ shift of the four combined anti-VEGF.2 antibodies was monitored over two rounds of sorting (FIG. 3C). A bimodal distribution of cells was observed in some of the samples, which was attributed to partial cell permeabilization and background autofluorescence of *E. coli*. The VEGF binding signal of the pooled variants overlayed after two rounds of sorting with the best expression variant, S24R.E6Q.M34I, suggesting that the better expressing antibodies were being enriched. The input sequencing shows that all four anti-VEGF.2 antibodies were present at the start of the sort, while anti-VEGF.2 WT and L4M.E6Q.M34I were partially depleted after Round 1 (FIG. 3D). After Round 2, anti-VEGF.2 WT and L4M.E6Q.M34I were not detected, and only F71Y.E6Q.M34I and S24R.E6Q.M34I was enriched. These data demonstrate that despite small expression differences, BAD can successfully enrich for the best-expressing antibodies.

The methods described above are useful in many applications. With respect to antibody engineering, it may be used with larger libraries for Fc-engineering, antibody discovery, or affinity maturation. Beyond antibodies, the BAD system could be applicable as a general high-throughput tool to study protein export, folding, or localization in the *E. coli* periplasm, as it offers a true readout in a cellular host environment. A major strength of this system is the non-tethered approach that allows for use of a native protein format, rendering fusion partners, reporter proteins, or membrane tethers unnecessary. Furthermore, the live-cell setting approach enables exceptionally rapid screening for desired host characteristics, a significant improvement over previous display technologies.

Materials

Plasmid Construction and Expression

Antibodies were cloned by standard molecular biology techniques into *E. coli* expression vectors (Simmons et al. *J. Immunol. Methods* 263: 133-147, 2002; Carter et al. *Biotechnology* (N.Y.) 10: 13-167, 1992) or mammalian expression vectors (Eaton et al. *Biochemistry* 25: 8343-8347, 1986) as previously described. Antibody expression was carried out using 50 mL *E. coli* cell cultures (Spiess et al. *J. Biol. Chem.* 288: 26583-26593, 2013) or 30 mL transient transfection cultures of CHO (Wong et al. *Biotechnol. Bioeng.* 106: 751-763, 2010) or HEK293T (Bos et al. *J. Biotechnol.* 180: 10-16, 2014) cells as previously described.

Antibody Purification

For purification of Fab protein from *E. coli*, protein was expressed as described earlier (Spiess et al. *Nat. Biotechnol.* 31: 753-758, 2013) in strain 64B4 (Reilly et al. *Antibody Engineering*, Springer Berlin Heidelberg, pp, 331-344, 2010) with a chromosomal lpp gene deletion. After growth of a 500 mL CRAP culture for 24 hours at 30° C., EDTA pH 8.0 was added to 10 mM final concentration. Incubation continued for 1 hr at 30° C. at 200 rpm, before $MgCl_2$ was added to 20 mM final concentration. Cell debris was removed by centrifugation (20 min, 4,500 rcf, 4° C.), followed by addition of 400 µg deoxyribonuclease I (Sigma-Aldrich, USA) before the supernatant was filtered through a GF/F filter (Whatman, England) and 0.2µ PES filter (Thermo Fischer Scientific, USA). 1.5 mL Protein G SEPHAROSE® slurry (GE Healthcare, USA) was added to 50 mL lysate and incubated overnight at room temperature. Unbound proteins were removed by washing with PBS, Fab protein was eluted with 4 ml 50 mM phosphoric acid pH 3, neutralized with 20× PBS, and concentrated with an AMICON® Ultra-4 concentrator (10,000 MW cutoff) (Merck Millipore, Ireland).

Human IgG1 was purified from mammalian culture supernatants by MABSELECT SURE™ (GE Healthcare, USA) according to the manufacturer's protocol. For human Fab purification from mammalian culture supernantants, a FLAG tag was added to the C-terminus of the heavy chain and the Fab was purified with anti-FLAG resin according to the manufacturer's protocol (Sigma-Aldrich, USA). Protein yields were quantified by determining the absorbance at 280 nm and using the protein specific extinction coefficient.

Antigens

Expression and purification of human $VEGF_{8-109}$ was described previously (Muller et al. *Proc. Natl. Acad. Sci. USA* 94: 7192-7197k 1997). Unizyme-tagged human $IL-13_{33-146}$ was expressed in *E. coli*, purified by Ni-NTA chromatography (Qiagen, Germany) under denaturing conditions and refolded. Proteins were fluorescently labeled with ALEXA FLUOR® 488 or ALEXA FLUOR® 647 succinimidyl ester (Invitrogen, USA) according to the manufacturer's protocol. DYLIGHT® 649 labeled goat anti-human IgG Fc F(ab')$_2$-fragment was obtained from Jackson Immuno Research, USA.

Bacterial Antibody Display and Flow Cytometry

For bacterial display, antibodies were expressed in a Lpp deletion (Δlpp) of strain 62A7. 62A7 was derived from the parental strain 33D3 by curing the kanamycin resistance of strain 33D3 (Simmons et al. *J. Immunol. Methods* 263: 133-147, 2002). For spiking experiments or experiments with individual framework variants, cells were individually transformed with the respective plasmids, grown as overnight cultures at 30° C., combined in the ratios described or equally by volume and used ata 1:100 dilution to inoculate 50 mL CRAP cultures. After 24 hours at 30° C., 1 OD aliquots were harvested and pelleted by centrifugation (4 minutes, 6500 rcf). Cells were resuspended in 100 μL PBS pH 7.4 with 2% BSA and 5 mM EDTA and incubated at 4° C. for 30 minutes. After initial incubation, SYTO® 41 or 9 nucleic acid stain (Molecular Probes, USA) was added to a final dilution of 1:100, and ALEXA$^{468}$- or ALEXA$^{647}$-labeled antigen added to a final concentration of 1-2 μM. Incubation was continued at 4° C. in darkness for 1 hour, at which time $MgCl_2$ was added to 10-20 mM final concentration. Unbound proteins were removed by washing 3 times with 1 mL volumes of PBS pH 7.4+20 mM $MgCl_2$. Stained cells were resuspended in SOC medium (New England Biolabs, USA) to a final concentration of 1×10 cellsiml for analysis and 1×10$^6$ cells/ml for sorting using a BD FACSARIA™ II Flow Cytometer. The FACS™ gating strategy included cells that were SYTO® dye-positive. Doublet discrimination gates were used to remove doublets and finally antigen-positive cells were sorted. Cells were sorted into SOC media, recovered at 30° C. overnight, and used to reinoculate expression cultures or frozen as glycerol stocks.

Microscopy

Expression and staining of cells for fluorescent microscopy was performed identically to the bacterial display protocol described above. Following the PBS with 20 mM $MgCl_2$ wash steps, cells were resuspended in 100 μL PBS with 20 mM $MgCl_2$ and mixed with 1% gelatin at 37° C. for slide preparation. Fluorescent microscopy was performed using a Zeiss Axio Imager A1.

Immunoblots

Immunoblotting was performed as described previously (Spiess et al. *Nat. Biotechnol*, 31: 753-758, 2013), except antibodies were expressed in a derivative strain of 33D3 cured of kanamycin resistance, Protein Stability Measurements by Differential Scanning Fluorimetry Protein stability was determined in a Biorad CFX96 Real-Time System (Bio-Rad, USA) with a final dilution of 1:500 of the SYPRO® Orange dye stock (Molecular Probes, USA), Fluorescence of a 25 μL sample in PBS was recorded from 20-100° C. (0.2° C. increments, 10 seconds hold per step).

Periplasmic Extract

To generate periplasmic extract for Biacore analysis, 40 mL of *E. coli* expression broth, from the bacterial antibody display strain, was pelleted by centrifugation at 5,000 rpm for 5 minutes. Pellets were resuspended in 1.5 mL of cold 50 mM Tris pH 8.0, 1 mM EDTA, and 500 mM sucrose and incubated on ice for 30 min with shaking. After centrifugation of the sample at 9000 rpm for 10 min, the supernatant was collected as the periplasmic extract.

Surface Plasmon Resonance

The binding kinetics of the anti-IL-13 and anti-VEGF antibodies was measured using surface plasmon resonance on a BIACORE™ 3000 or T200 instrument (GE Healthcare), respectively. All kinetics experiments were performed at a flow rate of 30 μL/min, at 25° C., and with a running buffer of 10 mM HEPES, pH 7.4, 150 mM NaCl, and 0.005% Tween-20. For anti-IL-13, Fab Binder from the Human Fab Capture Kit (GE Healthcare) was immobilized on a CMS sensor chip via amine-based coupling to capture anti-IL-13 half antibodies from *E. coli* periplasmic extracts. Human IL-13 binding to the antibody was measured using a two-fold concentration series of cytokine with a range of 1.56 to 50 nM. Sensorgrams for binding of IL-13 were recorded using an injection time of 120 seconds followed by 1000 seconds of dissociation time and regeneration of the surface between cycles with glycine pH 2.1. For anti-VEGF, human VEGF was immobilized on a CM5 sensor chip via amine-based coupling. A three-fold concentration series of anti-VEGF Fabs ranging from 6.17 to 500 nM was used to analyze binding to VEGF. Single cycle kinetics sensorgrams were recorded using an injection time of 120 seconds followed by 300 seconds of dissociation time and regeneration of the surface between cycles with 20 mM HCl. All sensorgrams observed for antigen binding to antibodies were analyzed using a 1:1 Langmuir binding model to calculate the kinetics and binding constants.

Example 2

Optimization of Cell Sorting Using Bacterial Antibody Display

Figure 8:
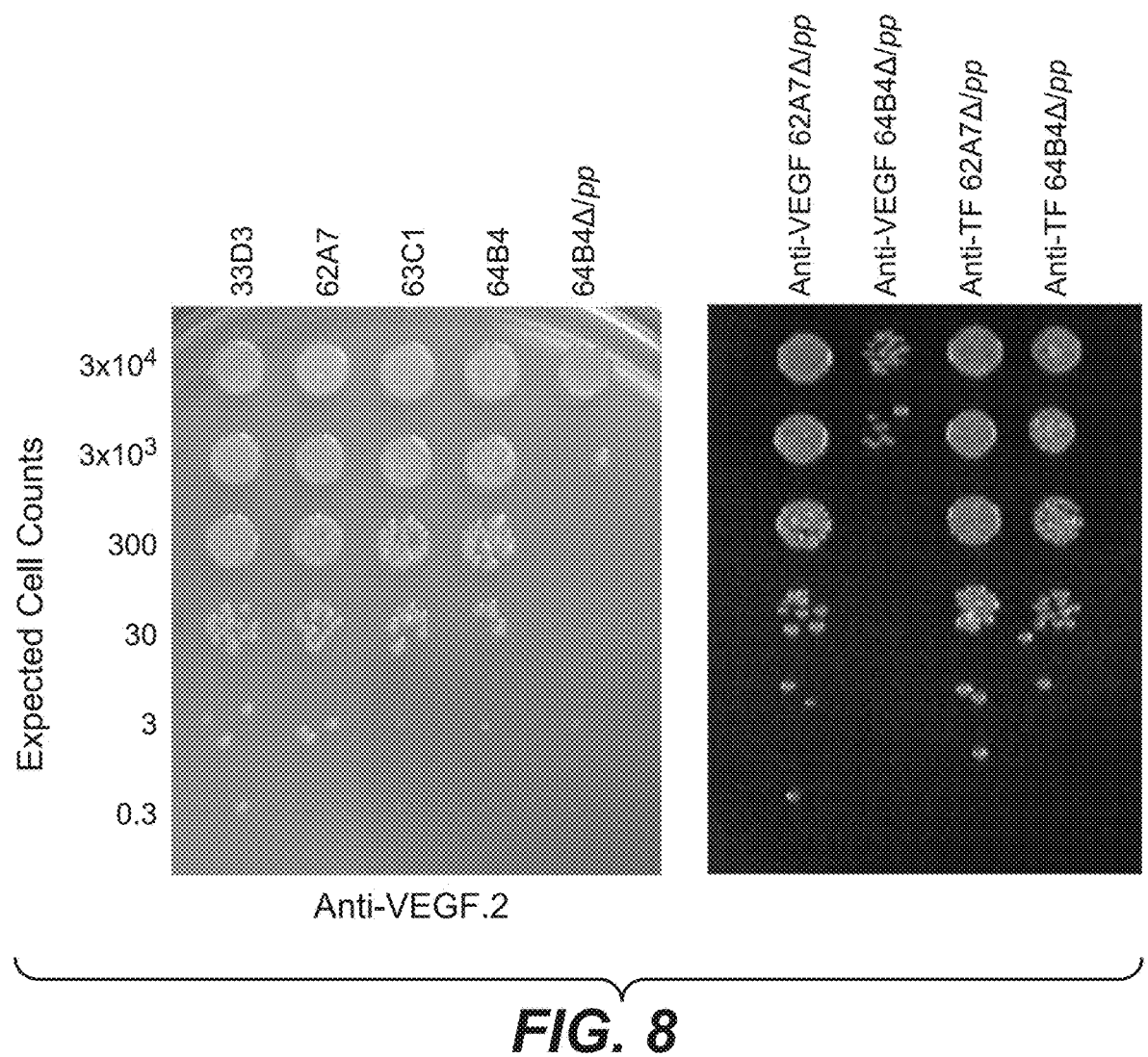
FIG. 8 shows images of bacterial media plates spotted with the indicated bacterial strains after expression of anti-VEGF.2 antibody. 1 OD/mL of cells was serially diluted and plated onto LB/Carbenicillin plates to visualize cell viability. Various wild-type expression strains showed differing degrees of viability after expression of an anti-VEGF antibody (left panel). The 62A7 strain showed a 1-log increase in viability compared to strain 64B4. Deletion of lpp in the 64B4 strain background led to a 3-log decrease in viability. The 62A7Δlpp strain showed increased viability compared to the 64B4Δlpp strain in cells that expressed anti-VEGF or anti-tissue factor (TF) antibodies (right panel).

In order to maximize cell viability during the sorting process to facilitate the speed and efficiency of round-to-round sorting using BAD, d the viability of different wild-type *E. coli* strains after expression of an antibody was compared. *E. coli* expression strains had variable viabilities after the expression of an antibody; for example, wild-type 64B4 cells had an approximate 1-fold decrease in cell viability compared to other wild-type strains, including 62A7 cells (FIG. 8). Further, 62A7 cells deleted for Lpp (62A7Δlpp) had greater viability than 64B4Δlpp cells (FIG. 8). 62A7Δlpp cells remained viable after FACS™ sorting following antibody expression and incubation with labeled antigen and could undergo multiple rounds of labeling and sorting. Therefore, choice of strain background is one factor that can be used to optimize the cell sorting process during BAD. In methods that use the Δlpp deletion, the method is compatible with any wild-type genetic background capable of expressing antibodies.

Figure 9:
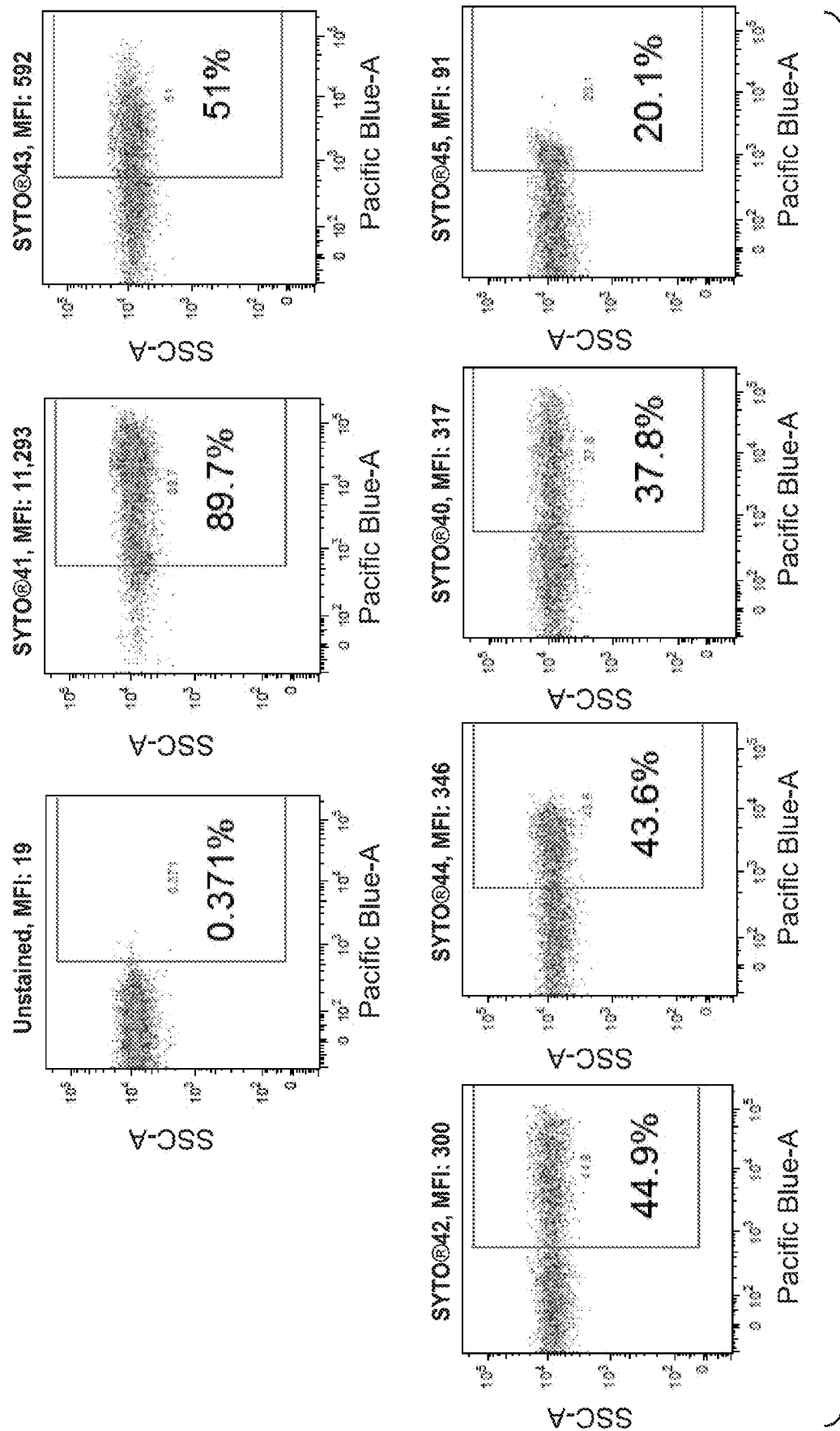
FIG. 9 is a series of graphs showing flow cytometric analysis of *E. coli* cells expressing anti-VEGF.V48L stained with the indicated blue fluorescent nucleic acid dye. A range of 20-90% cell-positive staining is observed. MFI, mean fluorescence intensity.
Figure 10:
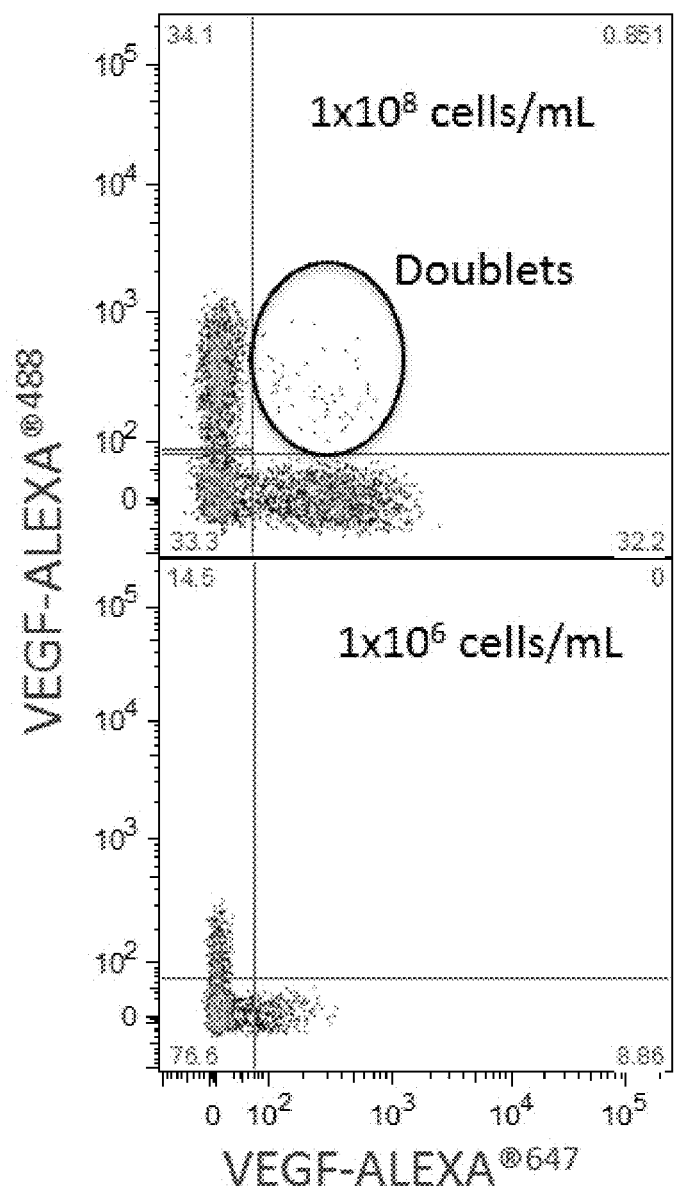
FIG. 10 is a series of graphs showing that cell concentration can affect the presence of cell doublets during flow cytometry during BAD screening. Two anti-VEGF variants, V48L and A97T, were separately expressed in strain 62A7Δlpp, and cells were labeled with VEGF antigen fluorescently-conjugated to ALEXA FLUOR® 488 and ALEXA FLUOR® 647, respectively. These labeled cells were then combined equally and were subjected to flow cytometric analysis. When concentrations of $1\times10^3$ cells/mL were analyzed, cells that were double-positive for both ALEXA FLUOR® dyes were present (top panel). However, decreasing the cell concentration to $1\times10^5$ cells/mL eliminated the doublets and only single-positive cells were observed (bottom panel).

The flow cytometry sorting conditions were also optimized to increase the amount of cells recovered after a sort. A variety of nucleic acid dyes were tested for their ability to improve detection of the *E. coli* cells during flow cytometry. A panel of six blue nucleic acid dyes (SYTO® dyes 40-45) was tested for staining efficiency of cells expressing an anti-VEGF antibody compared to an unstained control (FIG. 9), Dye-positive cells were detected using each of the nucleic acid dyes. Of the tested stains, SYTO® 41 gave the highest staining efficiency (approximately 90% of the treated cells). Using this nucleic acid dye as part of the selection strategy during flow cytometry increased the amount of cells recovered from the sorts. SYTO® 9 is a non-limiting example of a dye that stains with comparable efficiency to SYTO® 41. To facilitate enrichment of antibodies that have differences in expression levels and/or stability, the loss of antigen-positive cells during sorting should be minimized. The presence of cell doublets, which are two cells that are stuck together but detected as a single cell by flow cytometry, could in principle impair enrichment of antigen-positive cells after a sort. In this scenario, antigen-positive cells could stick to cells that are antigen-negative, thereby reducing enrichment. To test whether cell doublets occur under our sorting conditions, cells expressing the anti-VEGF antibody anti-VEGF.V48L were labeled with VEGF-ALEXA FLUOR® 488, while cells expressing anti-VEGF.A97T were labeled with VEGF-ALEXA FLUOR® 647. These cells were then combined equally and subjected to flow cytometry. At sorting concentrations of $1\times10^6$ cells/mL, cell doublets were present, as indicated by cells that were positive for both antigens (FIG. 10). To decrease the doublets a lower cell concentration of $1\times10^6$ cells/mL was used, which was sufficient to eliminate the doublets detected by flow cytometric analysis.

Figure 11:
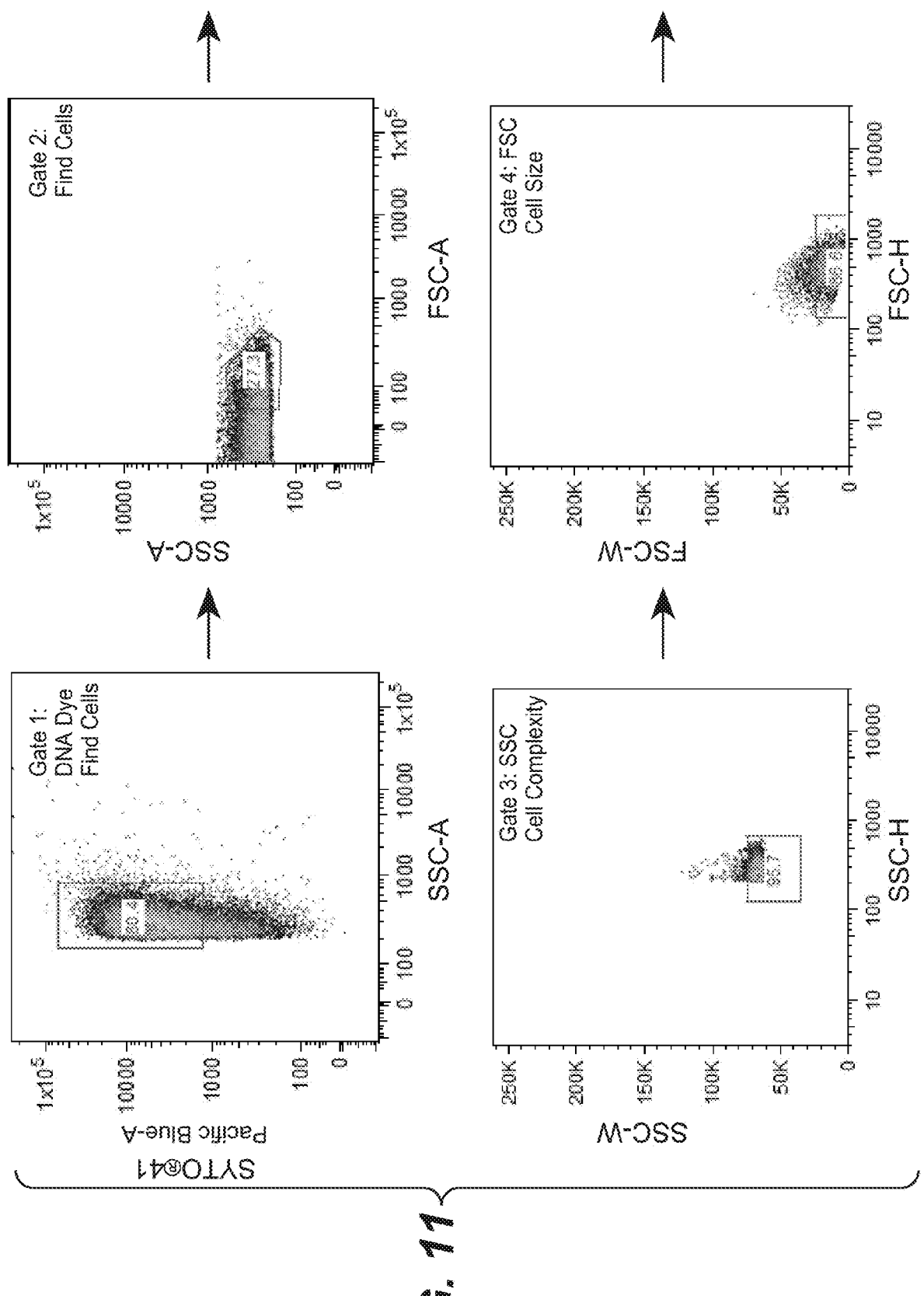
FIG. 11 is a schematic diagram showing an exemplary flow cytometry sorting strategy for Bacterial Antibody Display. Antibodies are expressed in a 62A7Δlpp *E. coli* expression strain. Cells are first selected based on being nucleic acid dye-positive compared to an unstained control. Next, cells are selected using forward and side scatter. Next, two standard gates are implemented that select for doublet elimination using cell complexity (width and height of side scatter, SSC) and small cell size (width and height of forward scatter, FSC). Finally, antigen-positive cells are selected using gates drawn above the shifts seen with cells expressing a non-binding antibody and unstained cells and/or an empty vector.
Figures 12A, 12B:
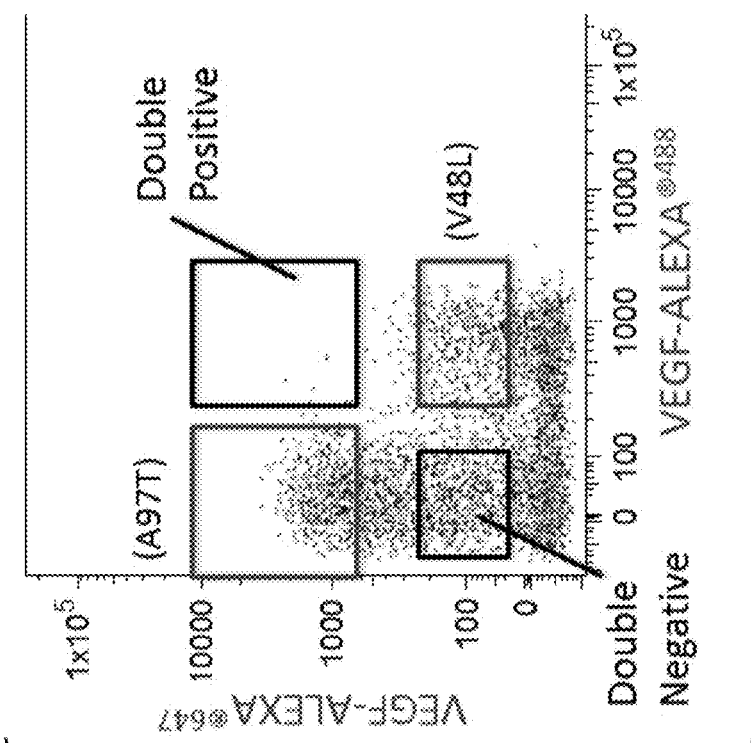
FIG. 12A is a graph showing that differentially-labeled antigen-positive cells can be successfully sorted using the strategy described in Example 4. Two anti-VEGF variants (V48L and A97T) were separately expressed in strain 62A7Δlpp and cells were labeled with VEGF antigen fluorescently-conjugated with ALEXA FLUOR® 488 and ALEXA FLUOR® 647, respectively. These labeled cells were then combined one-to-one and were sorted for being single antigen-positive (VEGF-ALEXA FLUOR® 488 or VEGF-ALEXA FLUOR® 647), binding to both antigens (double-positive), or binding to neither antigen (double-negative). The green box indicates cells that are expected to express the V48L variant, while the red box indicates cells that are expected to express the A97T variant. The sort input and outputs were plated, and 96 colonies sequenced. The right panel is a table showing the number of sorted events and the percentage of events that were positive post-analysis, as determined by running the sorted sample on the flow cytometry instrument to detect percent positive (% positive) binding to antigens.
FIG. 12B is a table showing the results of the sequencing analysis of the experiment presented in FIG. 12A. With a 1:1 input of the two anti-VEGF variants (V48L and A97T), each could be separately enriched to almost 95% after one round of sorting. The very low number of double-positive cells that could be sorted did not yield any colonies for sequencing, while the double-negative cells that did not bind either labeled antigen were composed of an equal combination of both antibody variants, indicating there was no selection bias.

A sorting strategy that combined the use of the 62A7Δlpp strain, sorting cell concentrations of $1\times10^6$ cells/mL, and flow cytometry that included sorting based upon the signal of the nucleic acid stain to facilitate locating the *E. coli* cells, standard doublet discrimination gates, and selecting for antigen-positive cells was tested (FIG. 11). To confirm that this sorting strategy would be successful, a single round of BAD was performed using 62A7Δlpp *E. coli* cells expressing anti-VEGF.V48L or anti-VEGF.A97T (described below in Example 4) that were labeled with VEGF-ALEXA FLUOR® 488 or VEGF-ALEXA FLUOR® 647, respectively, and combined equally. Cells were sorted based on single antigen-positive binding to the separately-labeled antigens, double-positive binding, or double-negative binding (FIG. 12A). An equal combination of both anti-VEGF variants was detected from sequencing the input clones. After one round of sorting, approximately 93-95% of the cells sorted as being positive for a single antigen expressed the expected anti-VEGF variant, confirming the accuracy of the sorting strategy (FIG. 12B). The double-negative population of cells did not have a bias selecting for either antibody, as an equal population of both anti-VEGF antibodies were found (FIG. 12B). These results show that the sorting conditions described in this Example are suitable to enrich clones after a single round of BAD. Cells were viable and could be recovered after the sort and plated, allowing ease of sequence analysis during a round of BAD and the ability to progress from round-to-round. Additionally, doublets did not interfere with the sorting capabilities of the method due to the high success rate of the sort, which was comparable to the limits of selection inherent in the FACS™ AriaII instrument used for this analysis.

Example 3

Generation of Anti-IL-13 Antibodies with Improved Expression and Stability Using the Methods of the Invention The methods described in Example 1 were utilized to select for increased functional expression and stability of a therapeutic anti-IL-13 antibody. Several approaches have been taken to increase antibody yields in *E. coli*, including saturation mutagenesis of select positions in the antibody sequence. However, as this approach predominantly leads to amino acid changes that are not found in the natural repertoire of antibodies, the risk of introducing immunogenic sequences into antibodies of therapeutic interest remains.

The present approach utilizes the natural framework diversity that occurs during somatic hypermutation. The Kabat database of naturally occurring antibodies (Kabat, supra) was examined, and amino acid changes from germline in the framework regions of kappa 4 light chain and VH2 heavy chain subtypes, the same as the anti-IL-13 antibody, were identified (FIG. 6). Without wishing to be bound by theory, framework residues should be less likely to affect affinity than the residues in the hypervariable regions. Additionally, buried residues in the framework regions should contribute to improved antibody folding and stability, but decrease the potential for immunogenicity compared to surface exposed residues.

Figure 13:
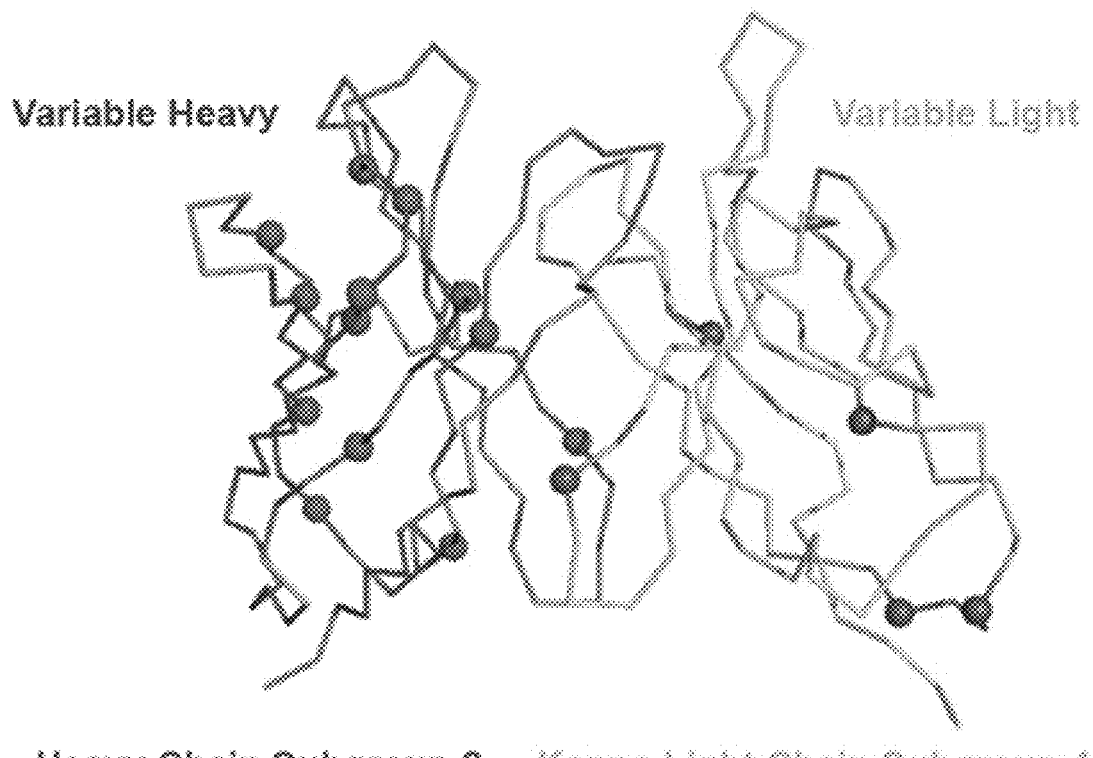
FIG. 13 is a ribbon diagram of the main chain antibody backbone based on the subtypes of the anti-IL-13 variable domains. Somatic hypermutation can introduce changes into both the framework regions and hypervariable regions. Collating data from the Kabat database, all the amino acid changes that occur by somatic hypermutation within the framework of the Variable Kappa 4 ($V_\kappa 4$) and Heavy 2 ($V_H 2$) subtypes were compiled, and then the chosen variants were narrowed to the non-solvent exposed residues (spheres). Single framework variants of anti-IL-13 half-antibody were made, 5 in the light chain and 28 in the heavy chain, and were combined to screen by BAD.

A ribbon diagram of the main chain antibody backbone based on the subgroup of the anti-IL-13 variable domains is shown in FIG. 13. Somatic hypermutation can introduce changes into both the framework regions and hypervariable regions. Collating data from the Kabat database, all the amino acid changes that occur by somatic hypermutation within the framework of the Variable Kappa 4 (VK4, yellow) and Heavy 2 ($V_H2$, grey) subtypes were compiled, and then the chosen variants were narrowed to the non-solvent exposed residues (spheres) based on an anti-IL-13 homology model. PyMOL was used to visualize the model to identify non-solvent exposed residues. Single framework variants of anti-IL-13 half-antibody were made, 5 in the light chain and 28 in the heavy chain, and were combined to screen by BAD.

Figure 4A:
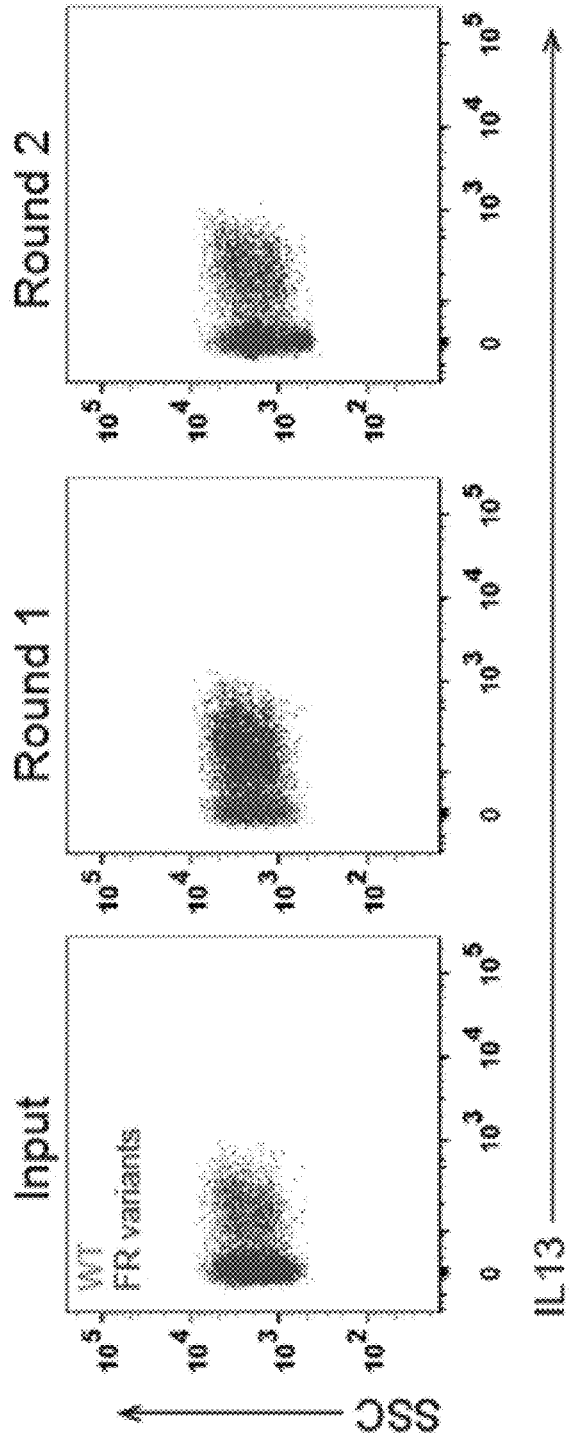
FIG. 4A is a series of graphs showing round enrichment of anti-IL-13 framework variants. Overlaid FACS™ dot plots show that anti-IL-13 framework (FR) variants shift more positive over each round compared with anti-IL-13 WT.
Figure 4B:
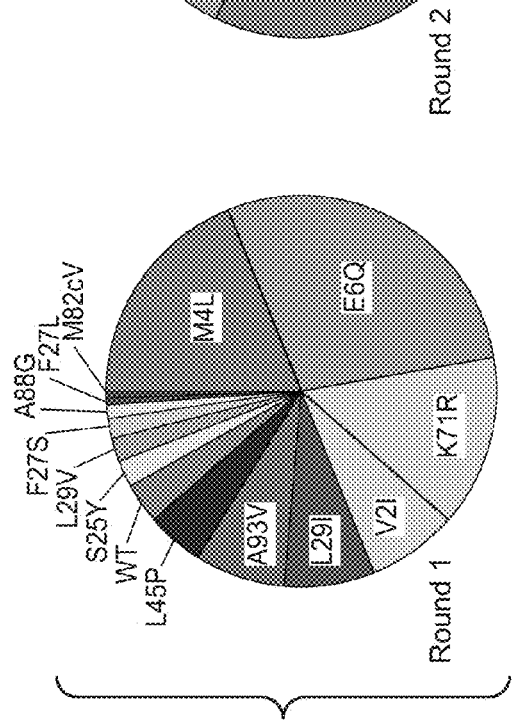
FIG. 4B is a series of pie charts showing anti-IL-13 library round enrichment. Data displayed from Round 1 and Round 2 are from sequencing 186 and 226 clones, respectively. M4L and E6Q are the most enriched variants after two rounds of BAD.

A BAD screen with the library of anti-IL-13 half-antibody framework variants was performed. Monitoring the FACS™ data over two rounds, the anti-IL-13 framework variants showed an increase in binding to IL-13 antigen compared to anti-IL-13 WT (FIG. 4A). The top 1% of IL-13-positive cells were sorted for based on the signal of the labeled antigen, and the sort outputs were sequenced. Anti-IL-13 WT was depleted by Round 2 (FIG. 4B), and the light chain M4L variant was largely enriched (82% of sequenced clones). In addition, the heavy chain variant E6Q (14% of sequenced clones) was also enriched, while the heavy chain variants S25Y, F27L, L29I and L45P and the light chain variant S12A were each observed in less than 2% of the sequenced clones.

To confirm that the anti-IL-13 framework variants identified after Round 2 increased functional expression, their expression levels in *E. coli* were compared using an anti-human Fc Western blot. The light chain variant M4L showed the highest increase in expression, about 2-fold better than anti-IL-13 WT (FIG. 4C), correlating to the best enrichment by BAD. The heavy chain framework variants E6Q and F27L also had higher expression levels than anti-IL-13 WT (FIG. 4C), whereas the rest of the variants had similar expression to anti-IL-13 WT. The Western blot data correlated to the ranking seen with individual framework variants binding to IL-13 antigen, measured by FACS™ mean fluorescence intensity. Antigen concentrations well above the $K_D$ were used to minimize the contribution of affinity differences and ensure that expression levels were driving the identification of the anti-IL-13 framework variants. Binding kinetic data was collected and confirmed that the anti-IL-13 framework variants M4L, E6Q, F27L and anti-IL-13 WT had comparable affinities (Table 2).

TABLE 2

Antigen affinity of anti-IL-13 half-antibody framework variants.

|  | $k_a$ (1/Ms, E+5) | $k_d$ (1/s, E−5) | $K_D$ (nM) |
|---|---|---|---|
| WT  | 13.0 ± 0.700 | 5.09 ± 1.40  | 0.040 ± 0.013 |
| M4L | 11.1 ± 0.603 | 3.16 ± 1.12  | 0.029 ± 0.010 |
| E6Q | 11.3 ± 1.01  | 4.26 ± 0.445 | 0.038 ± 0.007 |
| F27L| 13.0 ± 0.954 | 4.43 ± 0.362 | 0.034 ± 0.003 |

Figure 4C:
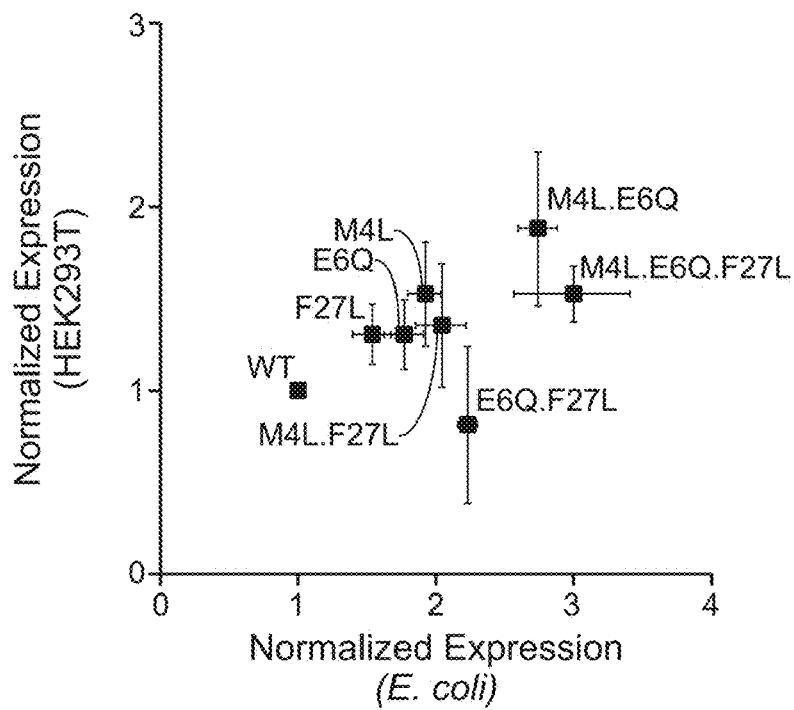
FIG. 4C is a graph showing correlation of the expression of anti-IL-13 variants and their combinations in mammalian (HEK293T) and *E. coli* cells. Improvement in expression is seen in both host systems. For *E. coli* expression, non-reduced soluble half-antibody samples were detected with an anti-human Fc antibody and quantified using a LI-COR ODYSSEY®instrument. For HEK293T expression, the Protein A-purified IgG yields were quantified. The expressions were normalized to anti-IL-13 WT. n=3 experiments.

In previous reports, mutations that increased antibody expression in *E. coli* did not translate to eukaryotic host systems (Demarest et al. *Protein Eng. Des. Sel*, 19: 325-336, 2006; Schaefer et al. *Protein Eng. Des. Sel.* 25: 485-506, 2012). To determine whether the screening strategy had identified variants that correlate to higher secretion levels in mammalian cells, allowing translatability of variant selection between expression hosts, the HEK 293T cell expression yields of the anti-IL-13 half-antibodies that provided an expression increase in *E. coli* were examined. While the gains were slightly smaller in eukaryotic cells, an almost linear correlation in expression gains between the two hosts was observed (FIG. 4C). Therefore, the screening strategy described herein can be used to identify variants that show improved expression in both *E. coli* and mammalian cells.

Figure 4D:
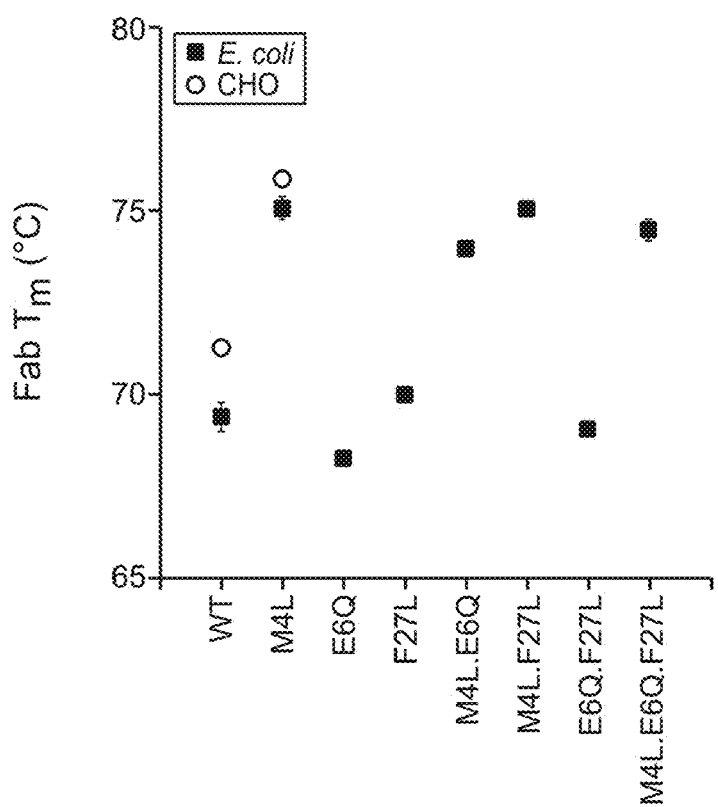
FIG. 4D is a graph showing thermostability of anti-IL-13 variants and their combinations measured by differential scanning fluorimetry (DSF). All variants containing the M4L mutation show a 5° C. increase in thermostability independent of the host expression system. To measure thermostability, Fabs and IgG were purified from *E. coli* and CHO cells, respectively. This graph shows the results of the Fab transition (the temperature at which half of the Fabs are melted), which is equivalent to the melting temperature $T_m$. The $T_m$ values of the Fab melt in Fab and IgG antibody formats were comparable.

To test whether the improvement in expression is correlated with an increase in conformational stability, differential scanning fluorimetry (DSF) was performed. The melting temperatures ($T_m$) of anti-IL-13 Fabs produced in *E. coli* with M4L, E6Q, or F27L mutations were compared to WT (FIG. 4D). The M4L variant increased thermal stability by about 5° C. ($T_m$ of 75.1±0.3° C.) compared to WT anti-IL-13 ($T_m$ of 69.4±0.4° C.). The E6Q and F27L mutations, however, did not yield a significant increase in thermodynamic stability. To verify that the increase in thermostability for the M4L variant is host-independent, the anti-IL-13 variants were produced as IgG in CHO cells. A similar 5° C. increase in thermostability was seen in a eukaryotic host.

Combination of the anti-IL-13 variants identified by the BAD screen might be additive and further increase functional expression. Therefore, expression levels in *E. coli* and mammalian cells for combinations of M4L, E6Q, and F27L were examined (FIG. 4C). The double combination M4L.E6Q shows an additive increase in expression levels in both hosts. These two variants were the only variants highly enriched in the BAD screen, further supporting the selection capabilities of our technology. Additionally, only variant combinations containing the M4L mutation show a 5° C. increase in thermal stability (FIG. 4D). Thus, a set of core framework variants that increase functional expression and thermal stability were identified to further improve the biophysical properties of an anti-IL-13 therapeutic antibody. While the in vitro properties of the molecule were improved, the clinical relevance of such variants has not been tested.

Example 4

Figure 7:
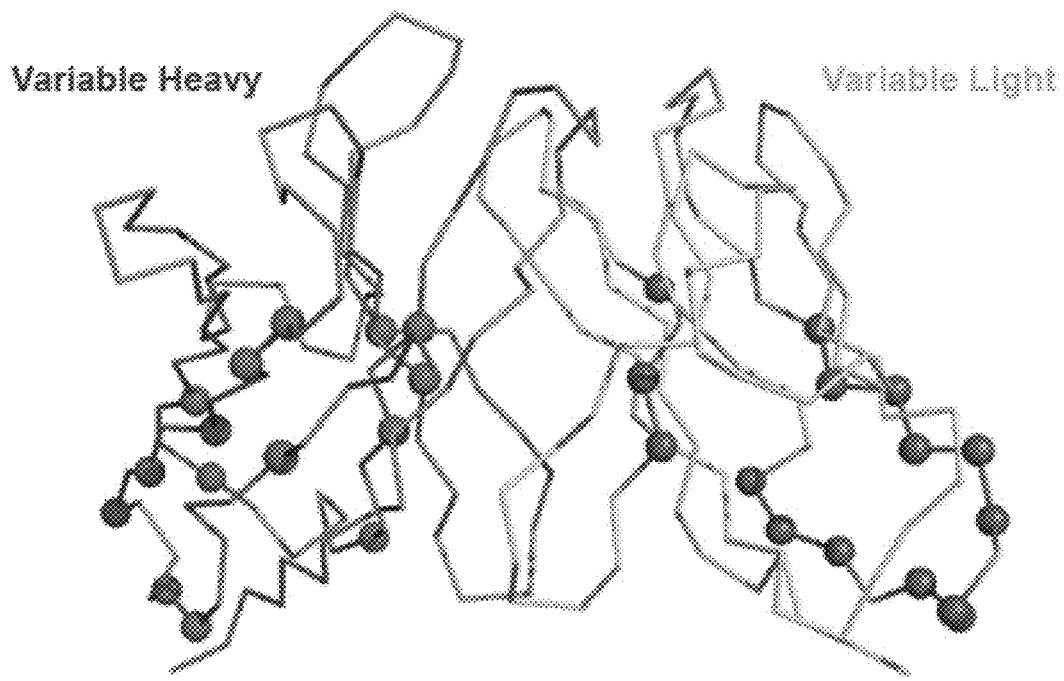
FIG. 7 is a ribbon diagram of the main chain antibody backbone for the variable domains of the anti-VEGF G6 antibody (Fuh et al, *J Biol Chem.* 281(10):6625-31, 2006). Light chain and heavy chain variable regions are labeled. Similar to the approach taken with the anti-IL-13 antibody (see FIG. 6), the Kabat database was scanned to identify residues introduced by somatic hypermutation that were in the FR of Variable Kappa 1 and Heavy 3 ($V_K1$ and $V_H3$, respectively) subtypes. The HVRs were excluded to maintain affinity, while buried residues (spheres) were also selected to reduce the risk of immunogenicity. With these criteria, single framework variants of an anti-VEGF half-antibody were created, 47 in light chain and 36 in heavy chain, and these were combined to screen by BAD.

Generation of Anti-VEGF Antibodies with Improved Expression and Stability Using the Methods of the Invention To further confirm that the strategy described in Examples 1 and 3 are generally applicable, the BAD method was used to improve the expression and stabilitiy of an antibody from a different germline, the anti-VEGF.3 antibody. Anti-VEGF.3 has kappa 1 light chain and VH3 heavy chain subtypes. Similar to the approach with anti-IL-13 described in Example 2, naturally occurring antibodies with these subtypes were collated from the Kabat database, and framework positions with variability from somatic hypermutation were identified (FIG. 7). Positions known to be important for VEGF binding and those that are solvent exposed were excluded in the analysis to lower the impact on affinity or immunogenicity, respectively.

Figure 5A:
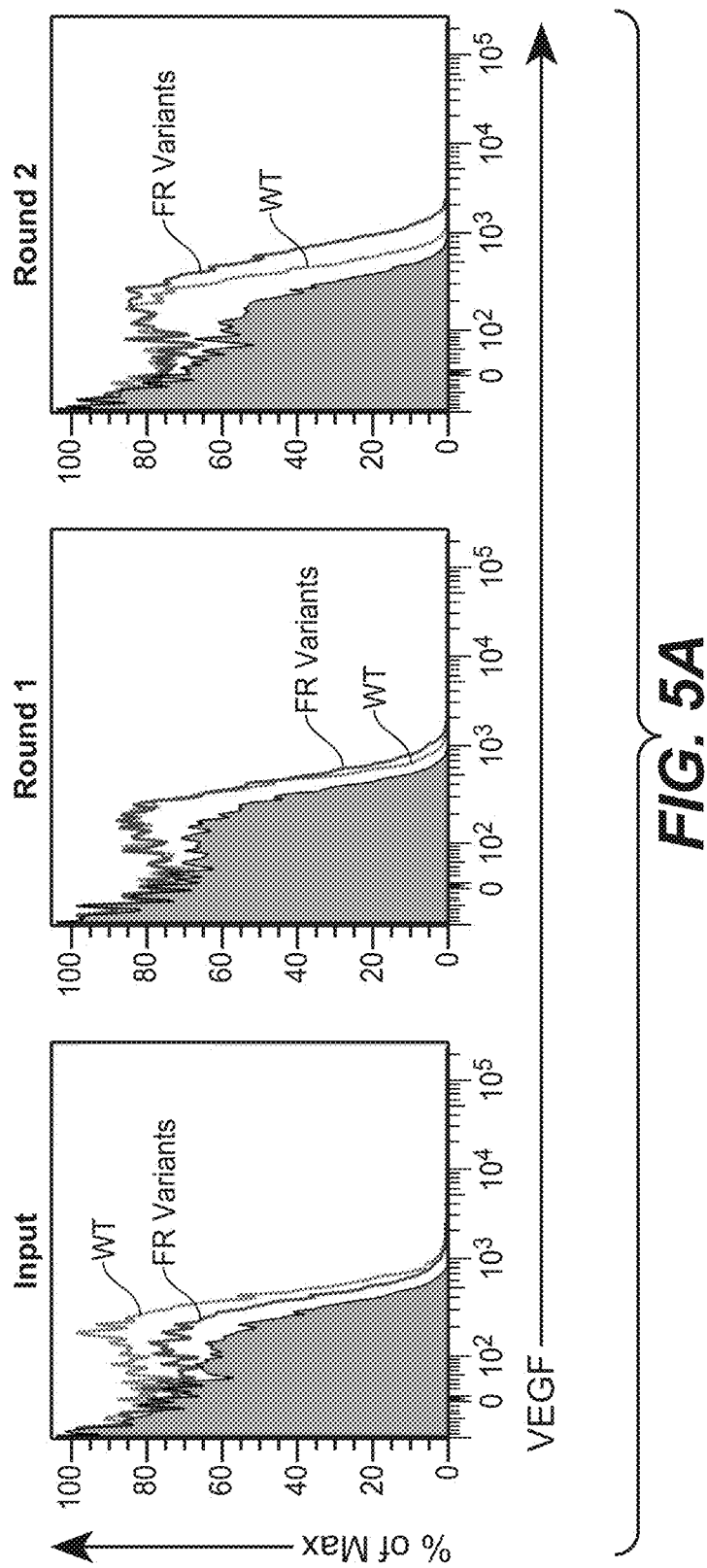
FIG. 5A is a series of graphs showing flow cytometric analysis of anti-VEGF.3 framework library enrichment after each round of FACS™. These data show that after Round 1 anti-VEGF.3 framework (FR) library variants shifted better than anti-VEGF.3 WT or unstained cells (black line, shaded), and the shift was further pronounced by Round 2.

A BAD screen was performed using the methods described in Examples 1 and 3 with the identified anti-VEGF.3 framework variants, combining 47 light chain variants, 36 heavy chain variants, and anti-VEGF.3 WT. The top 0.5% VEGF-positive cells were sorted for three rounds. Anti-VEGF.3 WT is depleted by Round 1, and framework variants showed an increase in binding to VEGF antigen compared to anti-VEGF.3 WT with progressing rounds (FIG. 5A).

Figure 5B:
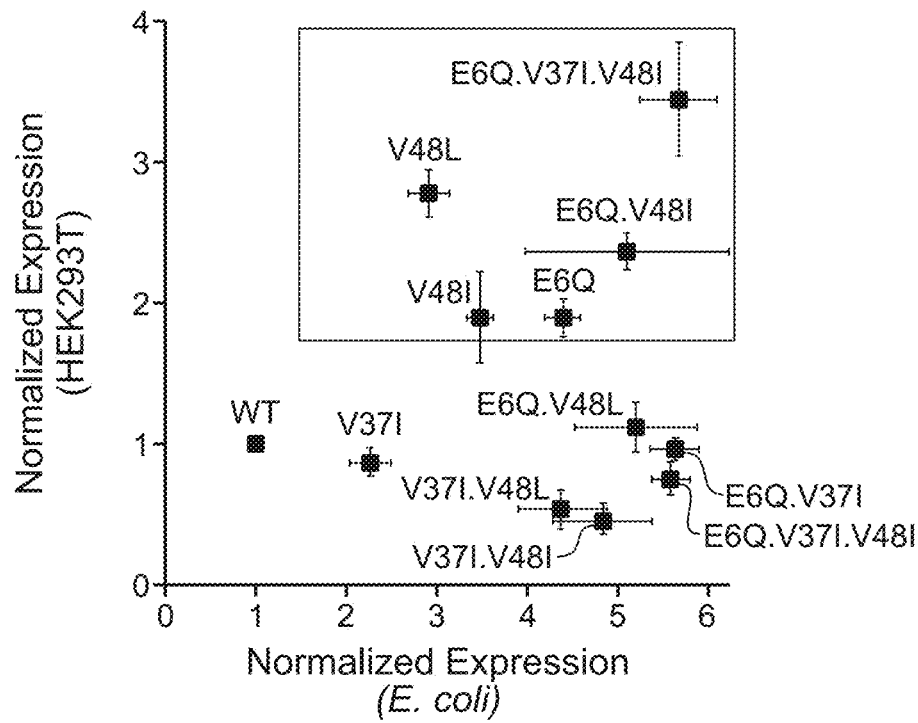
FIG. 5B is a graph showing that a subset of the anti-VEGF framework variants and their combinations that had improved expression in *E. coli* show a correlating increase in mammalian (HEK293T) expression (outlined box). Expression was normalized to anti-VEGF WT and was determined by an anti-Fc western blot of half-antibody (*E. coli*) or Protein A purified IgG (HEK 293T). n=3 experiments.
Figure 5C:
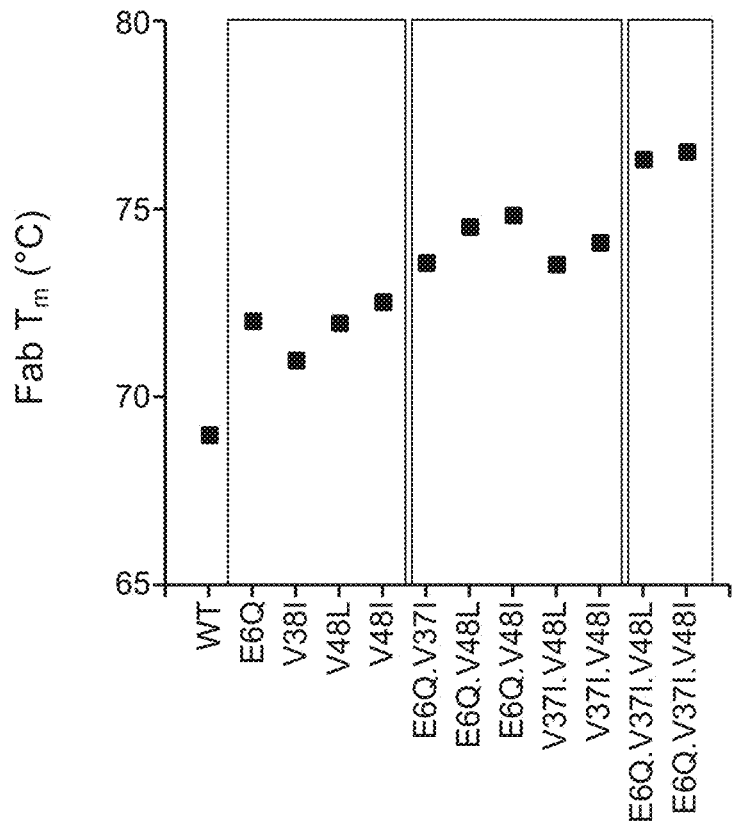
FIG. 5C is a graph showing that anti-VEGF.3 framework variants have increased thermostability and that combining framework variants had an additive effect. Differential scanning fluorimetry shows that the single framework variants E6Q, V37I, V48L or V48I (left box) increase thermostability. The double variants (middle box) further increased thermostability, and the triple variants (right box) had the largest additive increases. Fab transition values of the IgG are shown, n=3 experiments.
Figure 5D:
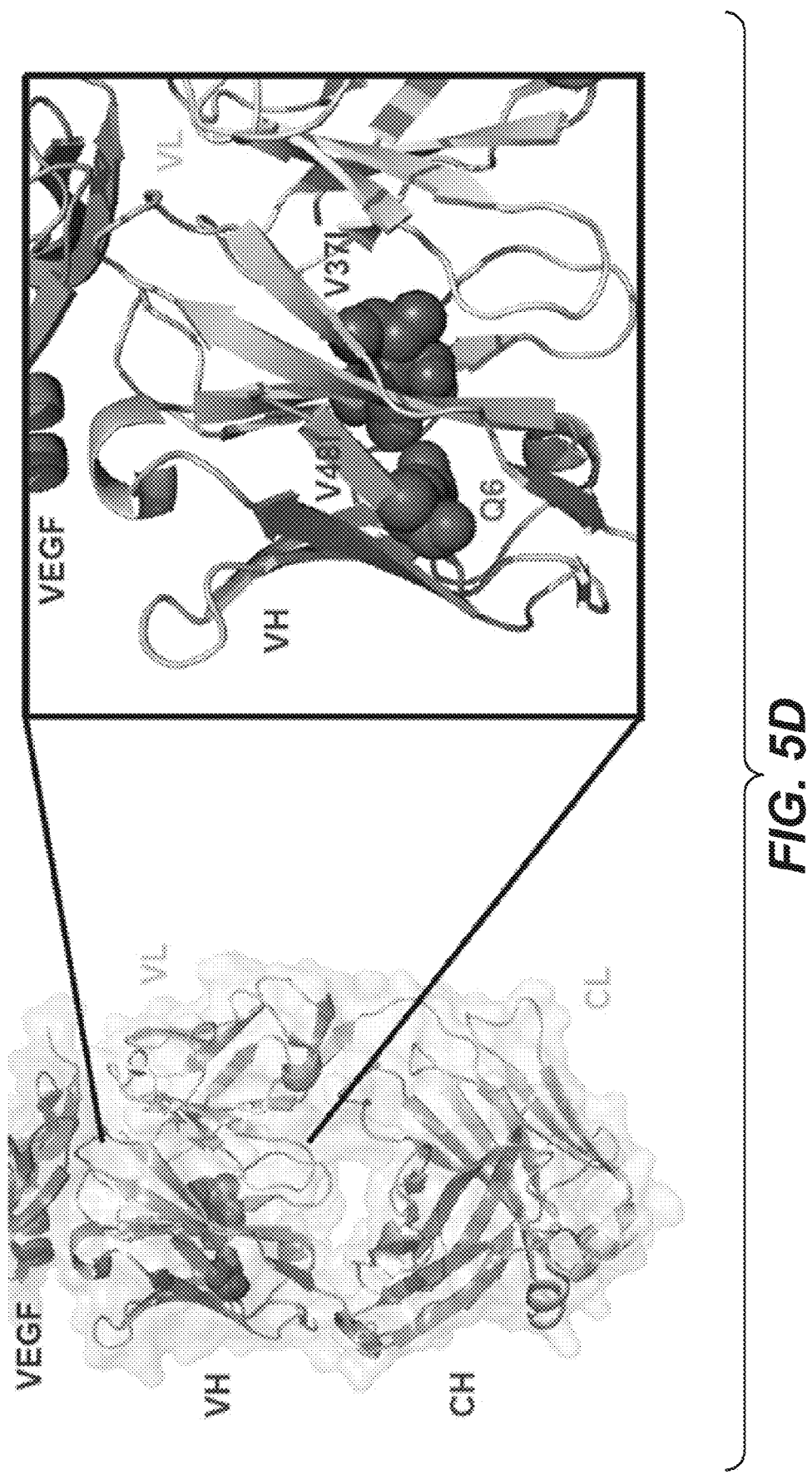
FIG. 5D is a rendering of the crystal structure of anti-VEGF G6 in complex with VEGF (RCSB Protein Data Base (PDB) Accession Number: 2FJG). The identified framework residues which increase expression and thermostability are shown on the X-ray crystal structure of anti-VEGF G6 in complex with VEGF (PDB: 2FJG). V37I and V48I mutations were modeled, while Q6 was in the native antibody structure. The three residues are located within a plane in the core of the heavy chain variable (VH) domain. E6 and V48I are located on separate strands in the beta barrel core of the VH domain, while V37I is in the buried interface between the VH and light chain variable (VL) domain. Heavy chain constant domain (CH), light chain constant domain (CL).

After Round 3, clones were enriched (FIG. 5A) and the expression and thermostability of the variants selected in BAD was tested in *E. coli* and HEK 293T cells. Anti-VEGF.3 heavy chain variants E6Q, V48L, and V48I (85%, 7%, and 3% of sequenced clones, respectively) improved expression by approximately 3-4.5-fold in *E. coli* (FIG. 5B). To determine whether the improved expression was correlated to increased stability, DSF was performed. All variants showed improved thermostability by about 3° C. compared to anti-VEGF.3 WT (FIG. 5C). The side chains of E6 and V48 (FIG. 5D) are positioned in the core of the beta-barrel of the variable heavy chain VEGF-Fab (Fuh et al. supra). Since the HQ, V48L, and V48I variants improved folding and provide superior stability, it suggested, without being bound to a particular theory, that the beta-sheet interface is slightly underpacked, and removal of the charge or a larger side chain would improve the packing. The V37I heavy chain variant (1% of Round 3 sequenced clones) improved the expression to a lesser extent (2.3-fold in *E. coli*) and increased thermostability by 2° C. (FIG. 5C). In contrast to E6 and V48, V37 is found at the interface with the light chain (FIG. 5D), illustrating the importance of the inter-chain as well as intra-chain contacts for antibody stability and folding.

Next, the framework variants were combined to study the potential of additive effects. All double variants had additive effects with improvements on functional expression of up to 5.6-fold in *E. coli* (FIG. 5B), while the combination of the three variants did not further improve the expression of the anti-VEGF antibody. Importantly, similar affinities to anti-VEGF WT were observed for all single, double and triple variants (Table 3).

TABLE 3

Antigen affinity of anti-VEGF.3 Fab framework variants.

|  | $k_a$ (1/Ms, E+5) | $k_d$ (1/s, E−5) | $K_D$ (nM) |
|---|---|---|---|
| WT | 0.313 ± 0.016 | 47.1 ± 1.94 | 15.1 ± 1.17 |
| E6Q | 0.448 ± 0.011 | 59.2 ± 3.71 | 13.2 ± 1.05 |
| V37I | 0.330 ± 0.014 | 50.8 ± 3.75 | 15.4 ± 1.79 |
| V48L | 0.346 ± 0.024 | 47.1 ± 3.26 | 13.6 ± 1.21 |
| V48I | 0.319 ± 0.011 | 47.1 ± 2.61 | 14.8 ± 1.25 |
| E6Q.V37I | 0.428 ± 0.008 | 57.7 ± 2.75 | 13.5 ± 9.17 |
| E6Q.V48L | 0.457 ± 0.013 | 50.6 ± 2.66 | 11.1 ± 9.07 |
| E6Q.V48I | 0.421 ± 0.013 | 56.6 ± 2.60 | 13.5 ± 1.06 |
| V37I.V48L | 0.352 ± 0.015 | 45.0 ± 2.82 | 12.8 ± 1.37 |
| V37I.V48I | 0.335 ± 0.014 | 50.5 ± 3.32 | 15.1 ± 1.61 |
| E6Q.V37I.V48L | 0.471 ± 0.079 | 53.0 ± 2.75 | 11.5 ± 2.21 |
| E6Q.V37I.V48I | 0.414 ± 0.015 | 58.4 ± 3.42 | 14.2 ± 1.36 |

Surprisingly, additive effects were observed with all variant combinations on protein stability, and the wild-type Fab is successively further stabilized up to 7.6° C. by combining variants at all three positions (FIG. 5C). This impressive increase in thermal stability highlights how the methods of the invention can be used during therapeutic antibody development to identify variants with improved thermal stability.

When these variants and combinations were expressed in a mammalian system, several of the expression yields correlated with the results observed in *E. coli* (FIG. 5B). All single variants, except V37I, improved the expression in HEK 293T cells by almost 2- to 3-fold. An additional increase in expression was observed by combining E6Q and V48I variants, and this was further improved by the V37I variant. The best expression was seen with this E6Q.V37I.V48I variant, which provided almost 4- to 6-fold increases in antibody yields in HEK 293T and *E. coli*, respectively.

In summary, the studies described in Examples 2 and 3 demonstrate that the expression yields and conformational stability of an antibody can be significantly optimized by a few changes in the framework region without altering the antigen affinity. Even though these framework variants were initially identified in *E. coli* cells, in many cases expression increases translated to mammalian cells.

Example 5

Improving Recombinant Protein Expression in Bacteria Using Global Transcription Machinery Engineering and Bacterial Antibody Display In addition to identifying variant binding polypeptides with improved binding and/or expression, the methods of the invention can also be used to engineer bacteria for improved expression of recombinant proteins (e.g., antibodies, half-antibodies, and antibody fragments). In this Example, global Transcription Machinery Engineering (gTME) was used in conjunction with BAD to screen for bacteria expressing mutant sigma factor proteins that conferred improved expression of an antibody.

Figure 14:
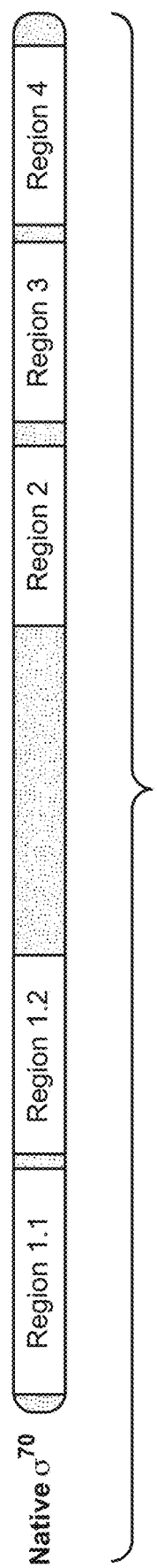
FIG. 14 is a schematic diagram of the domain structure of *E. coli* sigma factor RpoD ($\sigma^{70}$).

The gTME approach involves mutagenesis (e.g., via error-prone PCR) of genes encoding proteins that regulate the global transcriptome in order to create complex phenotypes that can be screened in a high-throughput manner. In this Example, sigma factors were subjected to error-prone PCR mutagenesis; however, in principle, any gene that affects transcription on a global level (e.g., RNA polymerase subunits (e.g., RpoA), transcription factors, and the like) could be used. Sigma factors bind to the RNA polymerase and are involved in initiation of transcription. Mutations in sigma factors can affect a multitude of genes and create complex phenotypes. Table 4 shows a list of *E. coli* sigma factors. RpoD is the major sigma factor in *E. coli* that is expressed during the exponential phase of growth, and it is considered to control the expression of approximately 2,000 promoters. FIG. 14 shows a diagram of the structure of sigma factor RpoD ($\sigma^{70}$). Region 1 (Region 1.1 and 1.2 in FIG. 14) is only present in primary sigma factors (RpoD and RpoS), and it is involved in ensuring that the sigma factor only binds to the DNA promoter region with RNA polymerase bound to the sigma factor. Between Region 1 and Region 2 is a spacing region that plays a role in thermal stability. Region 2 binds to the −10 element (TATAAT) of the promoter. Region 3 is in close proximity to the binding site of the RNA polymerase which is cross-linked to the ATP at the initiation site. Region 3 contains a helix-turn-helix DNA binding region. Finally, Region 4 binds to the −35 element (TTGACA) of the promoter. Region 4 also binds to anti-sigma factors. Mutagenesis of sigma factors is expected to affect transcription in several exemplary, non-limiting ways. Increased expression could result from mutant sigma factors that bind more tightly to DNA or to RNA polymerase, or that bind to anti-sigma factors and therefore prevent inhibition of the native sigma factor. Decreased expression could result from mutant sigma factors that can bind to the RNA polymerase or DNA and prevent transcription.

TABLE 4

*E. coli* sigma factors

| Sigma Factor | Number | Role |
|---|---|---|
| RpoD | $\sigma^{70}$ | Primary sigma factor; controls ~2,000 promoters |
| RpoE | $\sigma^{24}$ | Stress response sigma factor |
| RpoH | $\sigma^{32}$ | Heat shock sigma factor |
| RpoS | $\sigma^{38}$ | Stationary Phase sigma factor |
| RpoN | $\sigma^{54}$ | Nitrogen-limitation sigma factor |
| RpoF | $\sigma^{28}$ | Flagellar sigma factor |
| FecI | $\sigma^{19}$ | Ferric citrate transport minor sigma factor |

Figure 15A:
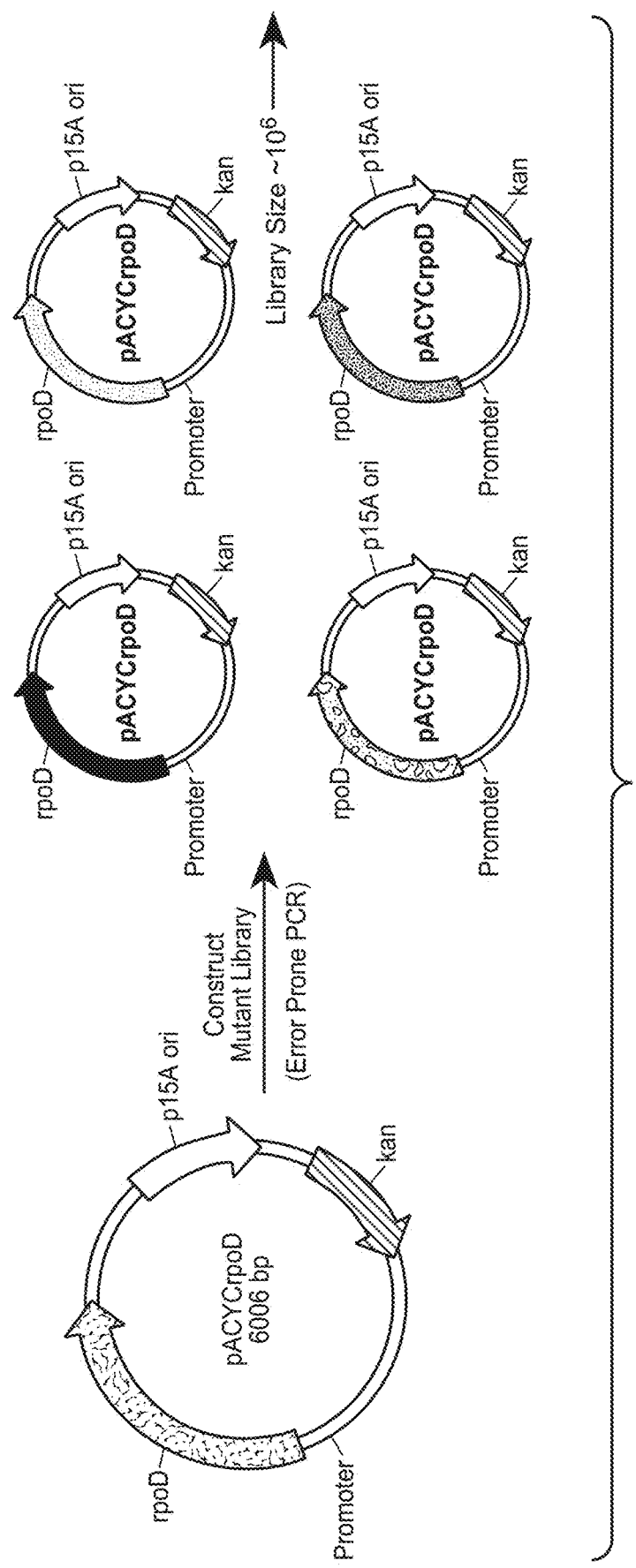
FIGS. 15A and 15B are schematic diagrams showing an exemplary strategy for construction of a mutant rpoD library by error-prone polymerase chain reaction (PCR). The pACYCrpoD plasmid (6006 bp) was mutagenized by error-prone PCR to generate a library size of approximately $10^6$ mutant plasmids (FIG. 15A). Upon transformation into *E. coli*, each mutant expresses a unique phenotype (indicated by the different arrows present in each cell in FIG. 15B).
Figure 15B:
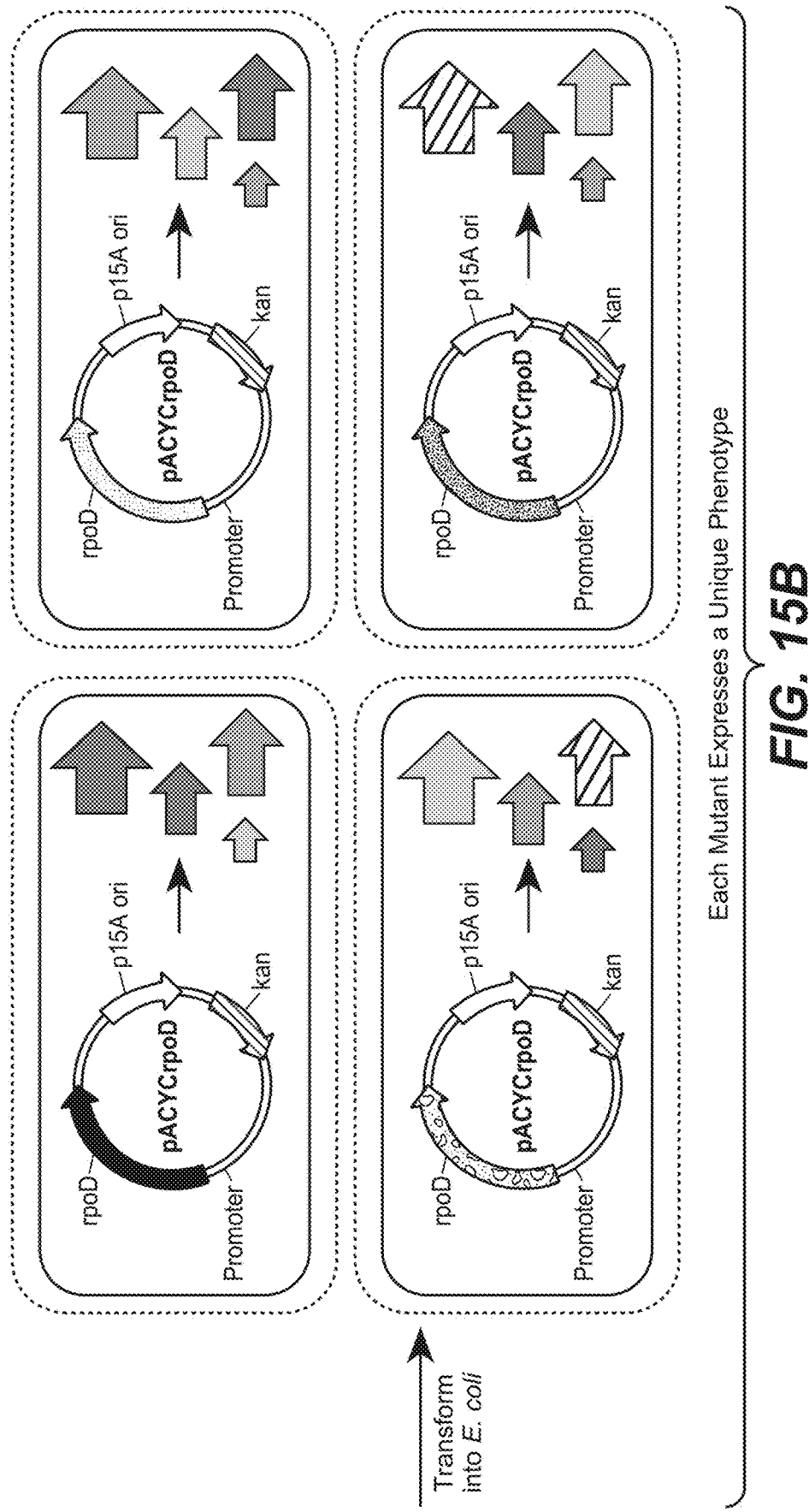

A library of plasmids encoding mutant RpoD proteins was generated by error-prone PCR mutagenesis (FIGS. 15A and 15B). The rpoD gene and native promoter was amplified using the primers F_rpoD_AatII 5'-TATGACGTCGAT-TAATGCCAAAAGCGGCAGA-3' (SEQ ID NO: 25) and R_rpoD_ScaI 5'-(SEQ ID NO: 26) and ligated together with the pACYC177 plasmid (possessing the p15A origin of replication and the kanamycin resistance marker (kan)) at the AatII and ScaI sites using standard methods. Transformants were grown on LB agar plates supplemented with 50 µg/ml kanamycin. The correct construct was confirmed by sequencing of the plasmid using the primers F_rpoD_check 5'-CTATTCTCAGAATGACTTGGTTG-3' (SEQ ID NO: 27) and R_rpoD_check 5'-GATGCTTTTCTG-TGACTGGTG-3' (SEQ ID NO: 28). Fragment mutagenesis was carried out using the GENEMORPH® II EZ Clone Kit (Agilent, Santa Clara, Calif.) according to the manufacturer's protocols. The plasmid library was propagated in NEB® Turbo cells and selected on LB agar plates supplemented with 50 µg/ml kanamycin. Diversity of the library was determined through sequencing and the error rate was found to be 1-4 mutations/kb. The estimated size of the library was approximately $10^6$.

Figure 16A:
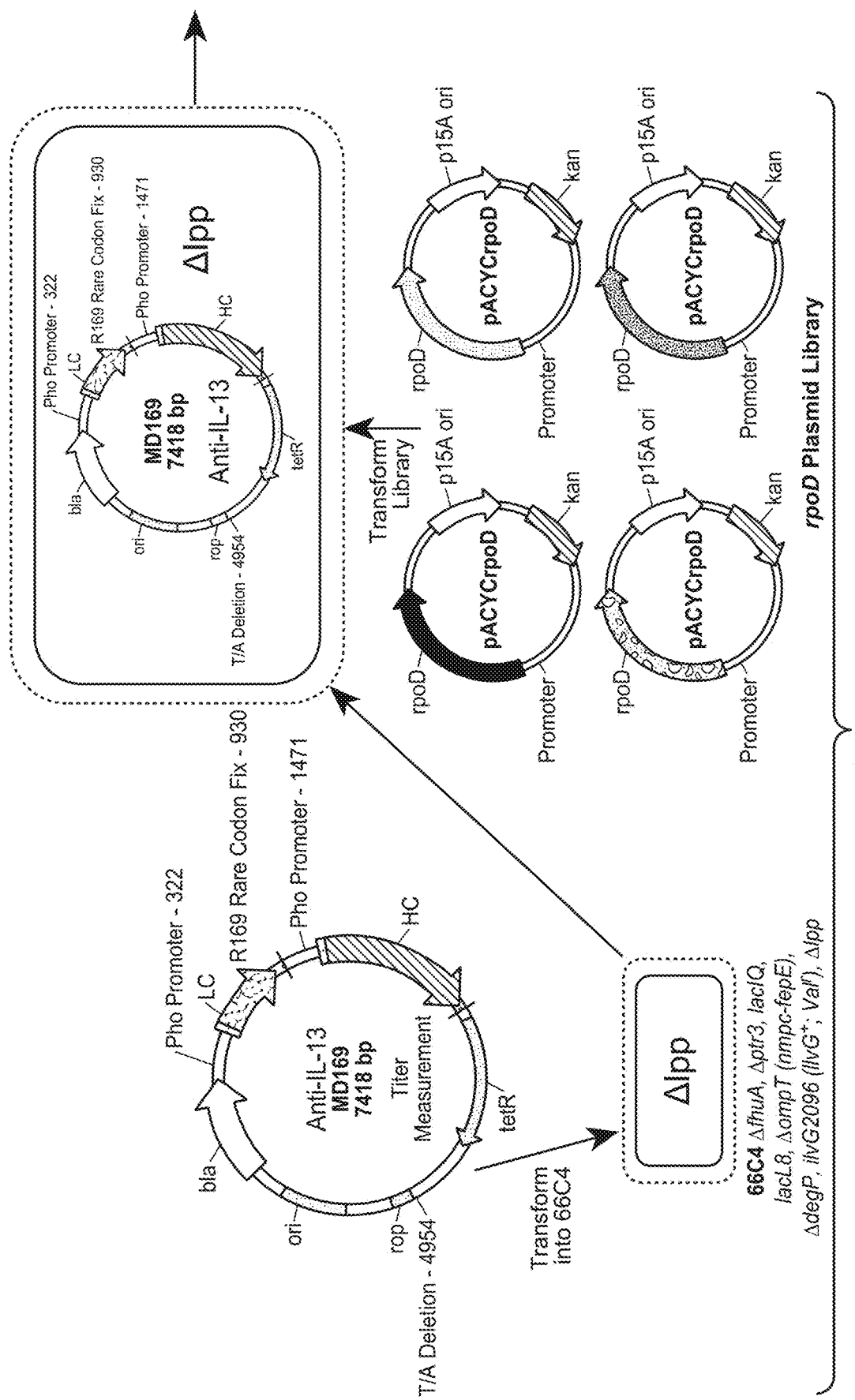
FIGS. 16A and 16B are schematic diagrams showing an exemplary strategy for preparing a mutant rpoD plasmid library for BAD screening. Strain 66C4 (Δlpp) was transformed with the MD169 plasmid encoding an anti-IL-13 antibody (FIG. 16A). The resulting transformant was further transformed with the mutant rpoD plasmid library, generating a 66C4 bacterial library pool having a diversity of approximately $10^6$ members (FIGS. 16A and 16B).
Figure 16B:
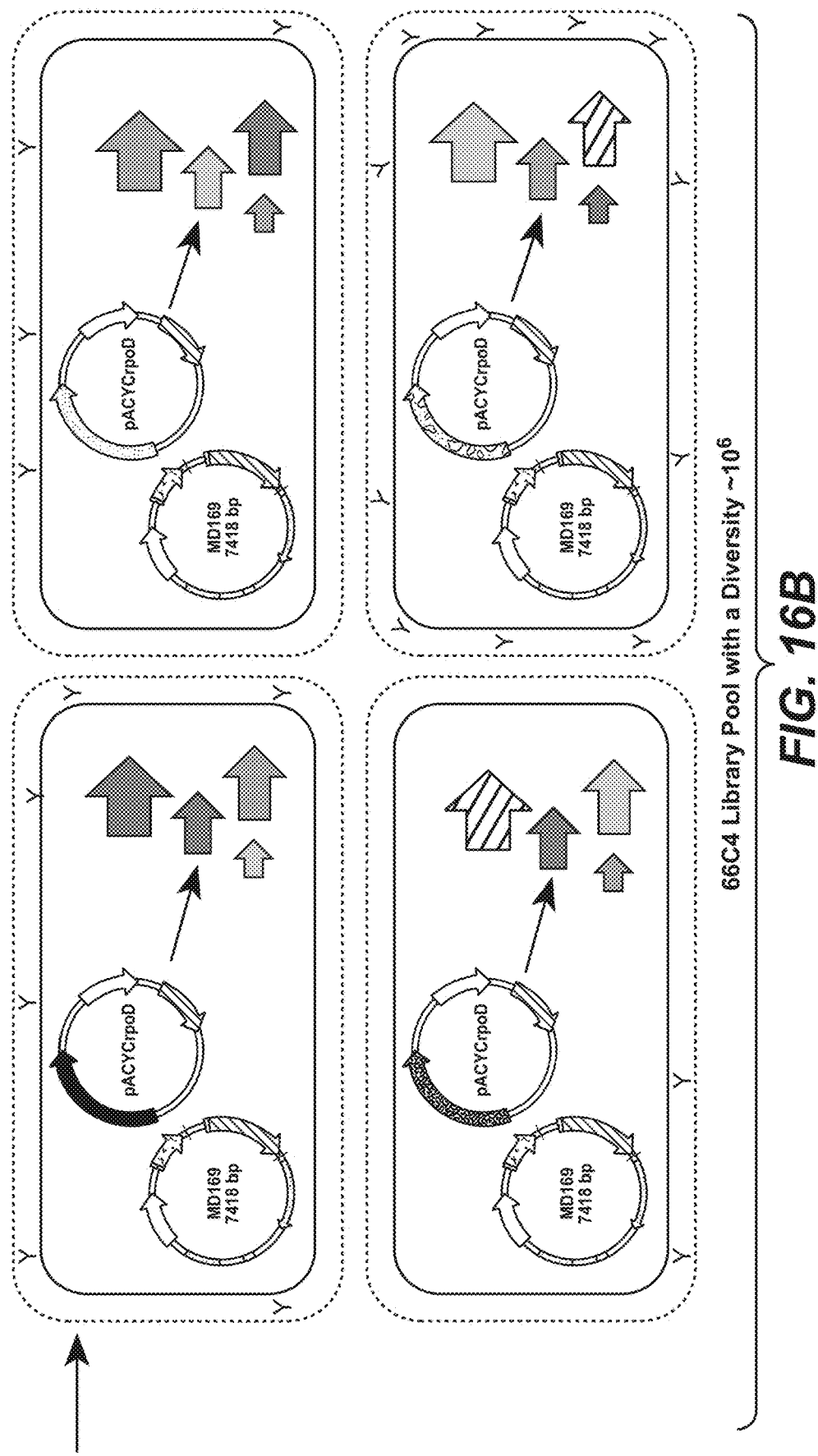

Next, a library of bacteria containing a deletion of the Lpp gene (Δlpp) for BAD screening was generated (FIGS. 16A and 16B). The 66C4 strain (Δlpp, ΔfhuA, Δptr3, lacIQ, lacL8, ΔompT(nmpc-fepE), ΔdegP, ilvG2096 (ilvG+; Val$^R$))

was transformed with the MD169 plasmid encoding the HC and LC of an anti-IL-13 antibody along with the bla beta lactamase antibiotic resistance gene and the tetracycline repressor (tetR) gene. Successful transformants were selected for their ability to grow on LB agar supplemented with 20 µg/ml tetracycline. Next, the resulting transformant (66C4 MD169) was transformed with the library of mutant rpoD plasmids described above expressing a unique, mutant rpoD and a kanamycin antibiotic resistance gene. Successful transformants were selected for their ability to grow on LB agar supplemented with 20 µg/ml tetracycline and 50 µg/ml kanamycin. A sample of the library was screened for diversity by sequencing. This resulted in a 66C4 library pool expressing both an rpoD mutant and the anti-IL-13 antibody with a diversity of about $10^6$.

Figure 17A:
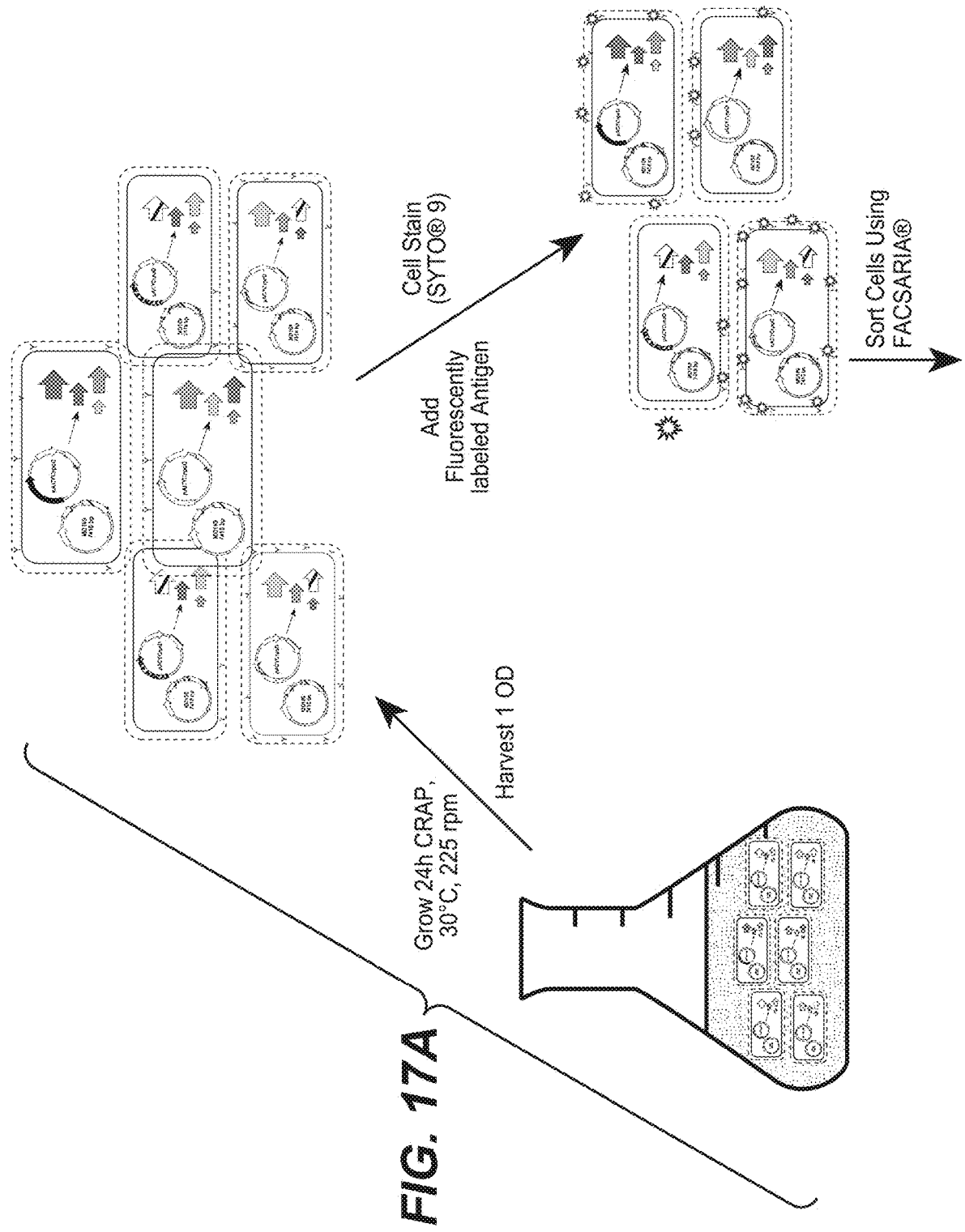
FIGS. 17A and 17B are schematic diagrams showing an exemplary strategy for BAD screening of a bacterial pool transformed with a mutant rpoD plasmid library. The 66C4 bacterial library pool was grown for 24 h in CRAP media at 30° C. with shaking at 225 rpm. 1 OD unit was harvested, permeabilized by treatment with EDTA, incubated with fluorescently labeled antigen (ALEXA FLUOR® 647-labelled human IL-13 ("ALEXA®$^{647}$-huIL-13") and a nucleic acid stain (SYTO®9), and the integrity of the outer membrane restored by addition of $MgCl_2$. The cells were subjected to flow cytometry using a FACSARIA® device using the indicated gating strategy (FIG. 17B). The top 1-3% of cells based on ALEXA®$^{647}$-huIL-13 signal intensity were sorted and grown for further rounds of BAD.
Figure 17B:
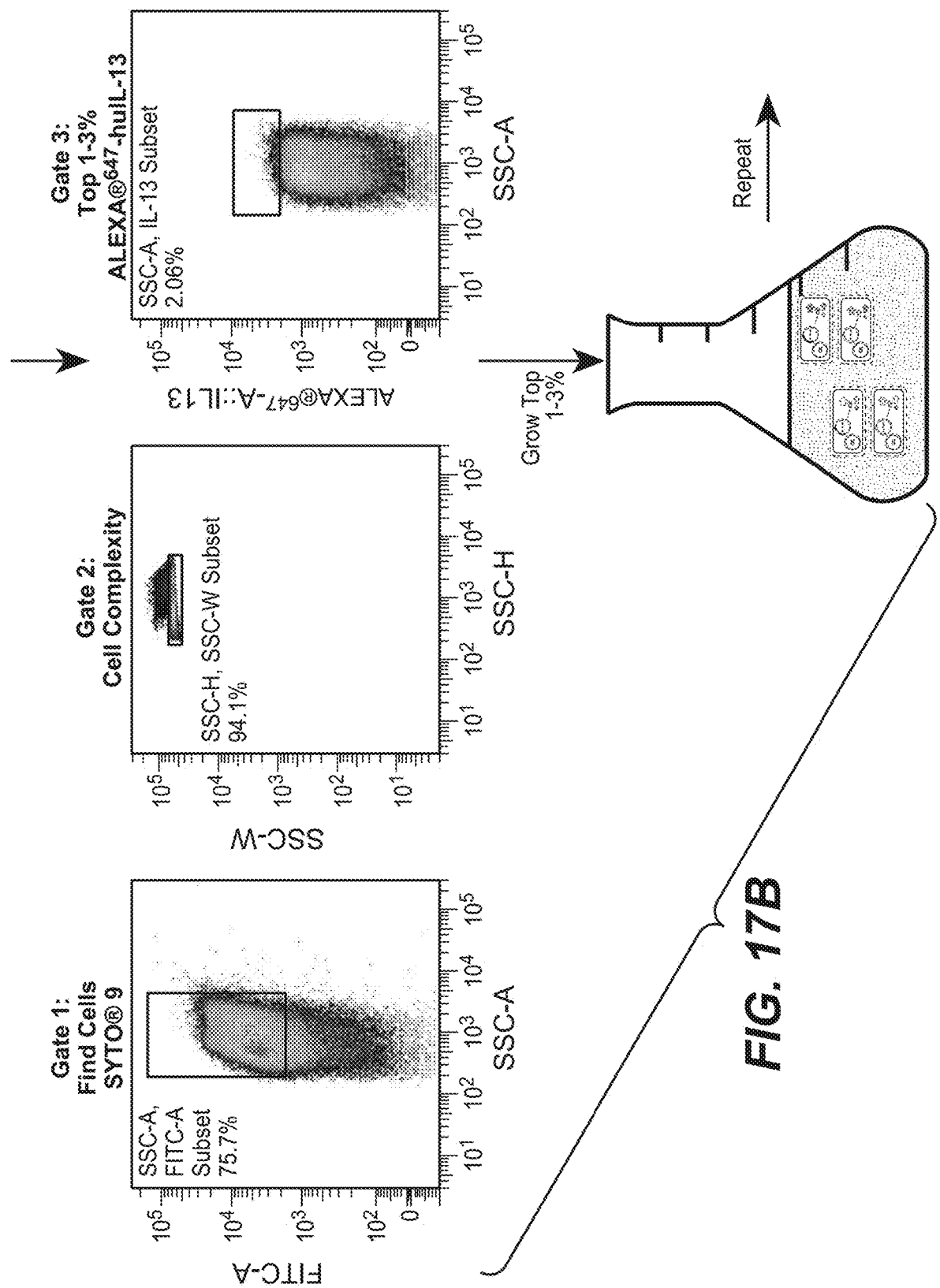

Next, the 66C4 library pool was screened using BAD (FIGS. 17A and 17B). The library was grown for 24 h in CRAP medium at 30° C. at 225 rpm. 1 OD unit was harvested, permeabilized with EDTA, stained using a fluorescently labelled antigen (ALEXA FLUOR® 647-labelled human IL-13; "ALEXA® 647-huIL-13") and DNA stain (SYTO® 9), and re-sealed with $MgCl_2$, essentially as described in Examples 1 and 2. Cells were sorted using a FACSARIA® flow cytometry device. Briefly, cells were first gated using SYTO® 9 to find cells. Next, cells were gated based on cell complexity. Finally, the top 1-3% of cells based on ALEXA® 647-huIL-13 signal were isolated by flow cytometry, grown, and the procedure was repeated. The 66C4 library pool was subjected to a total of four rounds of sorting using BAD.

Figure 18:
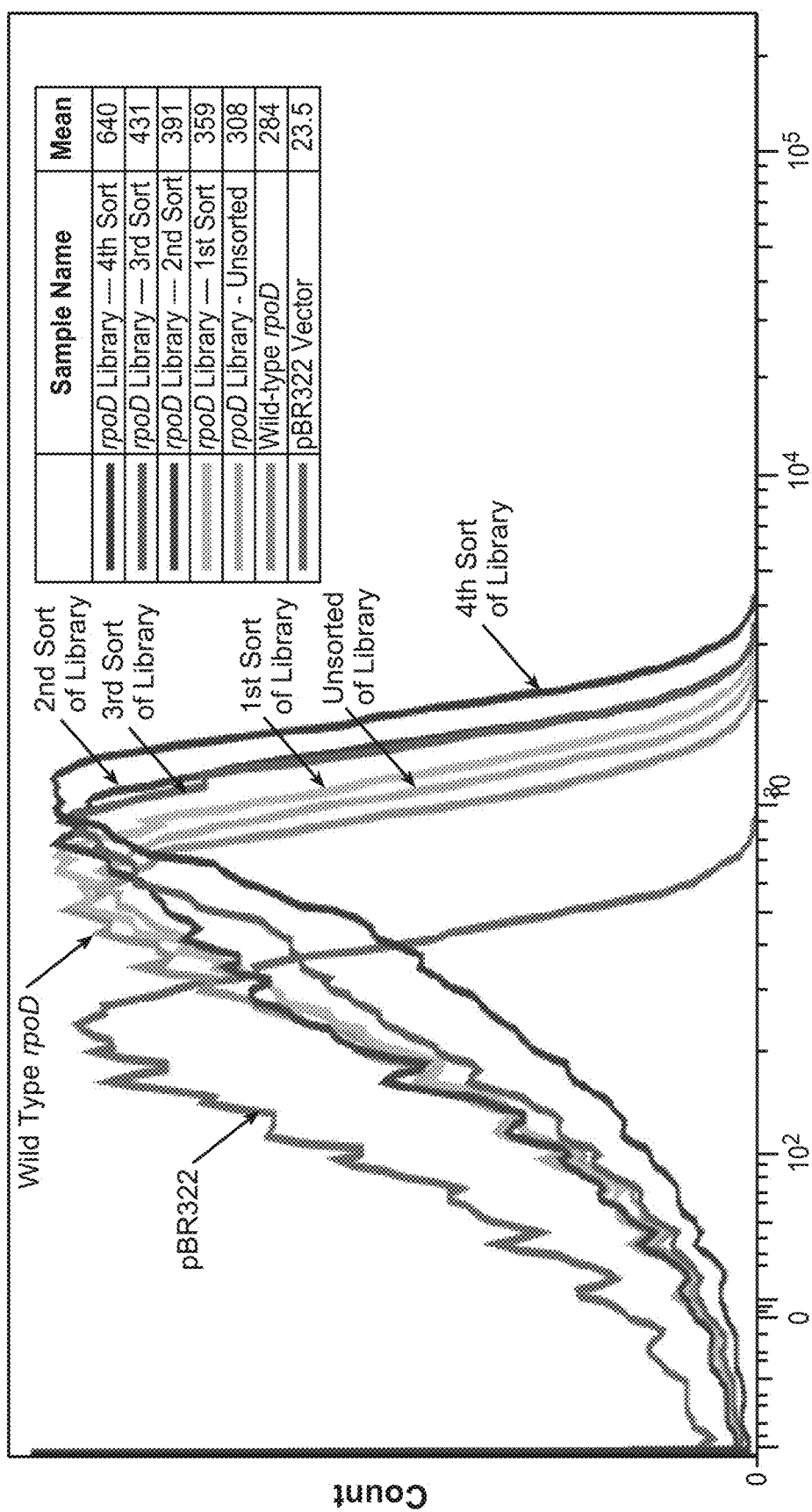
FIG. 18 is a graph showing the results of flow cytometric analysis of the indicated samples from BAD screening of the 66C4 bacterial library pool transformed with the mutant rpoD plasmid library. The inset table shows the sample and the mean fluorescence intensity ("Mean").
Figure 19:
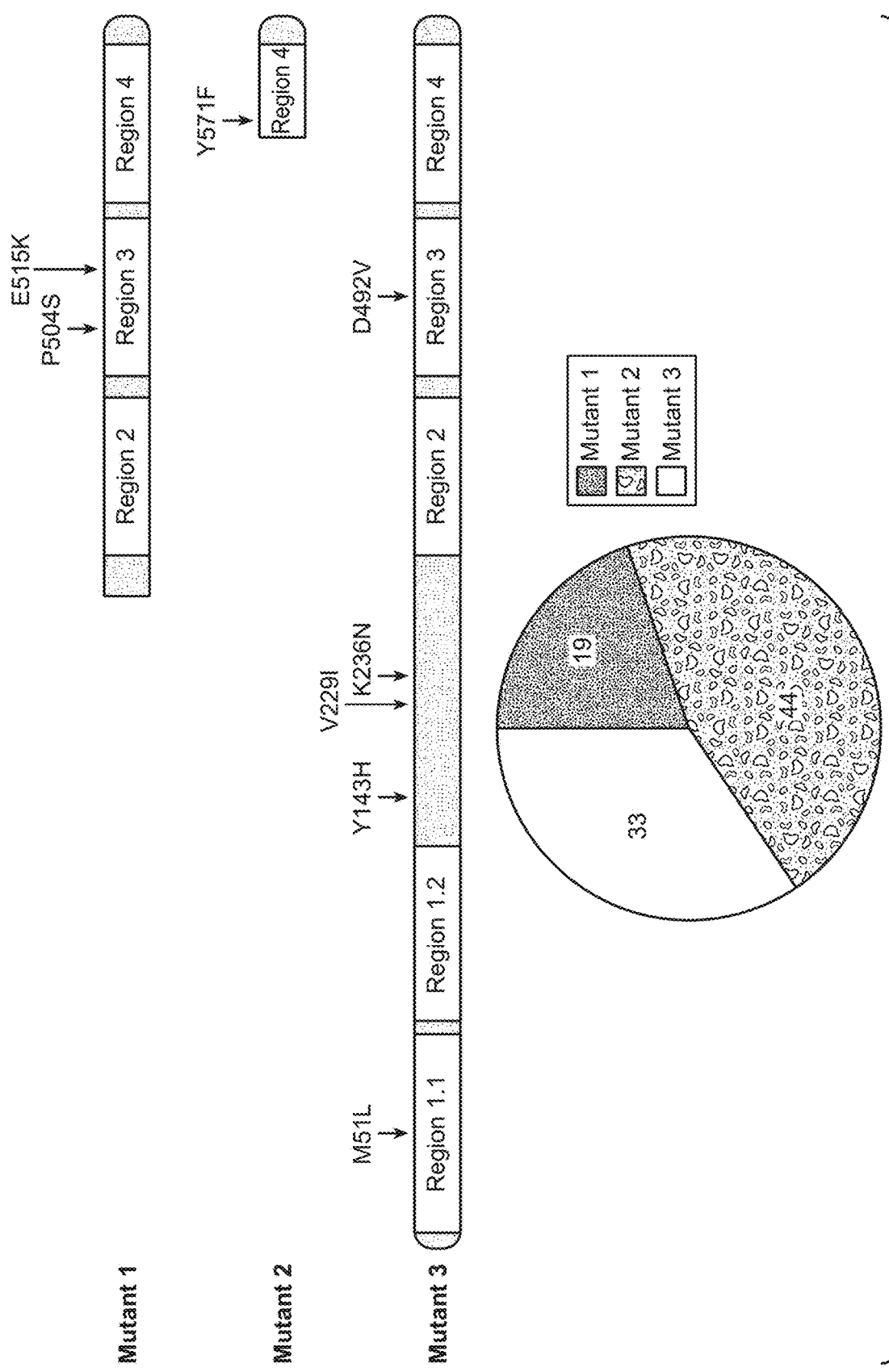
FIG. 19 is a schematic diagram showing three rpoD mutants identified by BAD screening of the 66C4 bacterial library pool transformed with the mutant rpoD plasmid library. Mutants 1 and 2 are truncation mutants that include the indicated point mutations relative to wild-type RpoD. The pie chart on the bottom of the figure shows the number of the indicated mutants observed out of 96 sequenced colonies.
Figure 20:
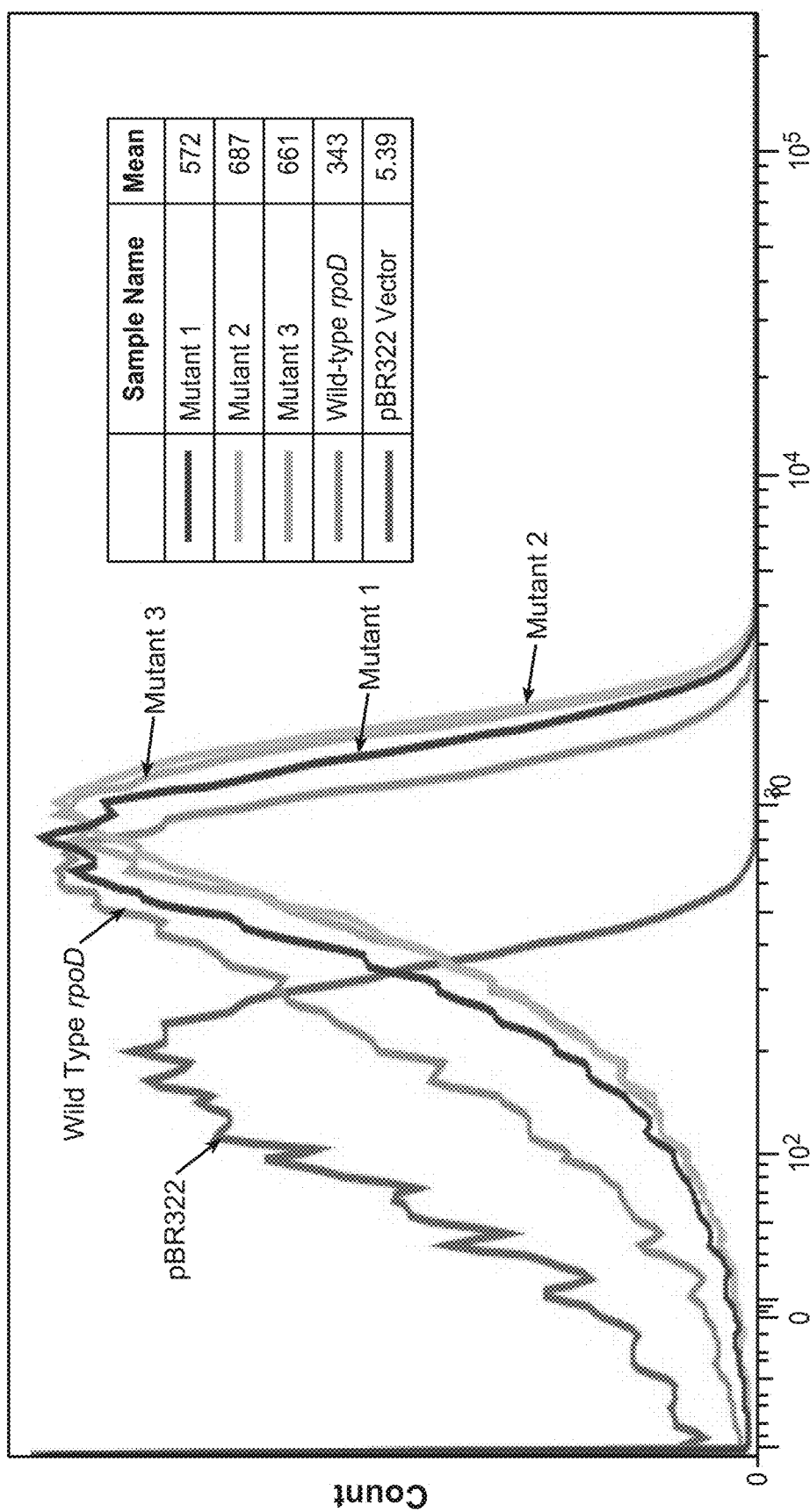
FIG. 20 is a graph showing the results of flow cytometric analysis of the indicated samples (*E. coli* expressing the indicated rpoD mutant, wild-type RpoD, or an empty vector control). The inset table shows the sample and the mean fluorescence intensity ("Mean").
Figure 21A:
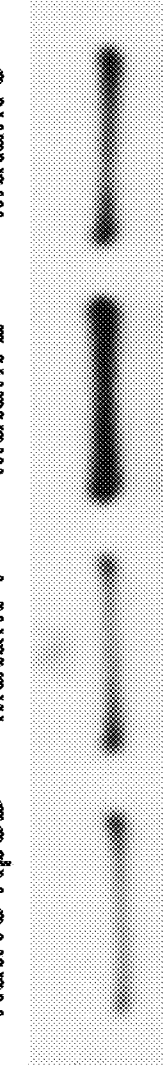
FIG. 21A is an immunoblot showing that expression of the indicated rpoD mutants resulted in increased expression of full-length anti-IL-13 in 66C4 host *E. coli* cells as compared to cells expressing native wild-type RpoD.
Figure 21B:
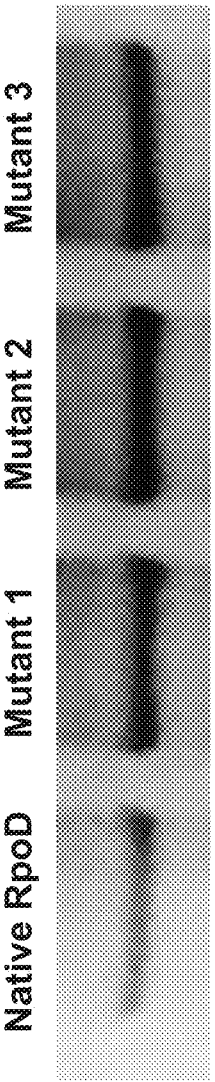
FIG. 21B is an immunoblot showing that expression of the indicated rpoD mutants resulted in increased expression of full-length anti-IL-13 in 67A6 host *E. coli* cells as compared to cells expressing native wild-type RpoD.

The results demonstrated that each round of BAD led to an increase in fluorescence intensity based on IL-13 binding compared to cells transformed with an empty vector or wild-type rpoD (FIG. 18), indicating that the population pool contained increased numbers of high-expressing clones. In contrast, poorly-expressing clones were sorted out by the BAD procedure. After the fourth round, the cells were plated and 96 colonies were randomly selected and sequenced. Three different mutants of rpoD were identified from the sequencing (FIG. 19). The amino acid sequence of wild type rpoD is shown in SEQ ID NO: 29. The amino acid sequence of rpoD Mutant 1 is shown in SEQ ID NO: 30. The amino acid sequence of rpoD Mutant 2 is shown in SEQ ID NO: 31. The amino acid sequence of rpoD Mutant 3 is shown in SEQ ID NO: 32. Mutants 1 and 2 included truncations along with point mutations (Mutant 1 included P504S and E515K, while Mutant 2 included Y571F), while Mutant 3 included 5 point mutations (M51L, Y143H, V229I, K236N, and D492V). Without wishing to be bound by theory, it is considered that the truncated mutants may bind more efficiently to anti-sigma factors, resulting in improved expression of the recombinant antibody. Individually analyzed rpoD mutants displayed an increase in fluorescence, indicating an increase in antibody expression (FIG. 20). The mutant with the highest mean fluorescence intensity (Mutant 2) was also the most abundant among the clones sequenced (FIG. 20). Antibody expression of the three rpoD mutants using non-reduced soluble samples from 1 OD of cells were also evaluated for expression of full-length anti-IL-13 by Western blot (FIGS. 21A and 21B) using standard methods. The mutants were first evaluated in the original host strain 66C4 (FIG. 21A), which showed similar results to flow cytometry analysis in that Mutant 2 gave the highest level of expression. The anti-IL-13 expression plasmid MD169 and the three mutants were individually transformed into a different host strain, 67A6 (ΔfhuA, ΔphoA, ilvG2O96 (IlvG⁺; Val'), ΔmanA, Δprc, spr43H1, laclQ, ΔompT, ΔmenE742, degP210A), to evaluate the transferability of the sigma factor mutants. The mutants were all found to increase antibody expression compared to 67A6 expressing the native RpoD protein sequence (FIG. 21B), demonstrating that the mutants can be transferred to other host *E. coli* strains and impart an increase in the expression level of full-length anti-IL-13 antibodies.

In conclusion, the methods of the invention can be used to engineer cells (e.g., bacteria) with improved expression of recombinant polypeptides, including antibodies and half-antibodies. The fact that cells remain viable across multiple rounds of sorting has a number of advantages, particularly in the context of high-throughput screening approaches, including faster identification of bacteria having mutations at multiple sites. The methods are compatible with a number of mutagenesis approaches of either plasmid-borne DNA or genomic DNA, including chemical mutagenesis, targeted mutagenesis, or transposon-based mutagenesis.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for identifying a bacterium comprising a binding polypeptide that specifically binds a target molecule, the method comprising the steps of:
   (a) providing a bacterium having an outer membrane permeable to a molecule having a molecular weight greater than 10 kDa, the bacterium expressing a nucleic acid encoding a binding polypeptide, wherein the binding polypeptide is present within the periplasm of the bacterium, wherein the bacterium comprises a mutation that allows for diffusion of membrane-impermeant molecules across the outer membrane into the periplasm, wherein the mutation is in a gene encoding major outer membrane lipoprotein Lpp (Lpp), and wherein the bacterium is a gram-negative bacterium;
   (b) (i) contacting the bacterium with the target molecule which is detectably labeled under conditions such that the target molecule binds to the binding polypeptide within the periplasm and (ii) removing unbound target molecules;
   (c) sorting the bacterium comprising the binding polypeptide that specifically binds the target molecule by the presence of the labeled target molecule within the periplasm, wherein the presence of the labeled target molecule within the periplasm is due to binding to the binding polypeptide, and wherein the bacterium remains viable following step (c); and
   (d) repeating the steps of the method at least once without an intervening step of isolating the nucleic acid.

2. A method for identifying a variant binding polypeptide with improved expression relative to a reference expression level, wherein the reference expression level is the expression level of a wild-type version of said variant binding polypeptide, wherein the variant binding polypeptide specifically binds a target molecule, the method comprising the steps of:
   (a) providing a bacterium having an outer membrane permeable to a molecule having a molecular weight greater than 10 kDa, the bacterium expressing a nucleic acid encoding a variant binding polypeptide, wherein the variant binding polypeptide is present within the periplasm of the bacterium, wherein the bacterium comprises a mutation that allows for diffusion of membrane-impermeant molecules across the outer membrane into the periplasm, wherein the mutation is in a gene encoding Lpp, and wherein the bacterium is a gram-negative bacterium;
   (b) (i) contacting the bacterium with the target molecule which is detectably labeled under conditions such that the target molecule binds to the variant binding polypeptide within the periplasm and (ii) removing unbound target molecules; and
   (c) sorting the bacterium comprising a variant binding polypeptide having improved expression, relative to the reference expression level, of the variant binding polypeptide by the presence of the labeled target molecule within the periplasm, wherein the presence of the labeled target molecule within the periplasm is due to binding to the variant binding polypeptide, and wherein the bacterium remains viable following step (c).

3. The method of claim 1, wherein the target molecule has a molecular weight less than 250 kDa.

4. A method for identifying a bacterium comprising a binding polypeptide that specifically binds a target molecule, the method comprising the steps of:
  (a) providing a bacterium comprising a mutation that allows for diffusion of membrane-impermeant molecules across the outer membrane into the periplasm, wherein the mutation is in a gene encoding Lpp, the bacterium expressing a nucleic acid encoding a binding polypeptide, wherein the binding polypeptide is present within the periplasm of the bacterium, and wherein the bacterium is a gram-negative bacterium;
  (b) (i) contacting the bacterium with the target molecule which is detectably labeled under conditions such that the target molecule binds to the binding polypeptide within the periplasm and (ii) removing unbound target molecules; and
  (c) sorting the bacterium comprising the binding polypeptide that specifically binds the target molecule by the presence of the labeled target molecule within the periplasm, wherein the presence of the labeled target molecule within the periplasm is due to binding to the binding polypeptide, and wherein the bacterium remains viable following step (c).

5. A method for identifying a variant binding polypeptide with improved expression relative to a reference expression level, wherein the reference expression level is the expression level of a wild-type version of said variant binding polypeptide, wherein the variant binding polypeptide specifically binds a target molecule, the method comprising the steps of:
  (a) providing a bacterium comprising a mutation that allows for diffusion of membrane-impermeant molecules across the outer membrane into the periplasm, wherein the mutation is in a gene encoding Lpp, the bacterium expressing a nucleic acid encoding a variant binding polypeptide, wherein the variant binding polypeptide is present within the periplasm of the bacterium, and wherein the bacterium is a gram-negative bacterium;
  (b) (i) contacting the bacterium with the target molecule which is detectably labeled under conditions such that the target molecule binds to the variant binding polypeptide within the periplasm and (ii) removing unbound target molecules; and
  (c) sorting the bacterium comprising a variant binding polypeptide having improved expression, relative to the reference expression level, of the variant binding polypeptide by the presence of the labeled target molecule within the periplasm, wherein the presence of the labeled target molecule within the periplasm is due to binding to the variant binding polypeptide, and wherein the bacterium remains viable following step (c).

6. The method of claim 1, further comprising subjecting the bacterium to conditions that permeabilize the outer membrane of the bacterium prior to step (b).

7. The method of claim 6, further comprising resealing the outer membrane of the bacterium following contacting the bacterium with the detectably labeled target molecule.

8. A method for identifying a bacterium comprising a binding polypeptide that specifically binds a target molecule, the method comprising the steps of:
  (a) providing a bacterium expressing a nucleic acid encoding a binding polypeptide, wherein the binding polypeptide is present within the periplasm of the bacterium, wherein the bacterium comprises a mutation that allows for diffusion of membrane-impermeant molecules across the outer membrane into the periplasm, wherein the mutation is in a gene encoding Lpp, and wherein the bacterium is a gram-negative bacterium;
  (b) subjecting the bacterium to conditions that permeabilize the outer membrane of the bacterium;
  (c) contacting the bacterium with the target molecule which is detectably labeled under conditions such that the target molecule binds to the binding polypeptide within the periplasm;
  (d) resealing the outer membrane of the bacterium following step (c) and removing unbound target molecules; and
  (e) sorting the bacterium comprising the binding polypeptide that specifically binds the target molecule by the presence of the labeled target molecule within the periplasm, wherein the presence of the labeled target molecule within the periplasm is due to binding to the binding polypeptide.

9. A method for identifying a variant binding polypeptide with improved expression relative to a reference expression level, wherein the reference expression level is the expression level of a wild-type version of said variant binding polypeptide, wherein the variant binding polypeptide specifically binds a target molecule, the method comprising the steps of:
  (a) providing a bacterium expressing a nucleic acid encoding a variant binding polypeptide, wherein the variant binding polypeptide is present within the periplasm of the bacterium, wherein the bacterium comprises a mutation that allows for diffusion of membrane-impermeant molecules across the outer membrane into the periplasm, wherein the mutation is in a gene encoding Lpp, and wherein the bacterium is a gram-negative bacterium;
  (b) subjecting the bacterium to conditions that permeabilize the outer membrane of the bacterium;
  (c) contacting the bacterium with the target molecule which is detectably labeled under conditions such that the target molecule binds to the variant binding polypeptide within the periplasm;
  (d) resealing the outer membrane of the bacterium following step (c) and removing unbound target molecules; and
  (e) sorting the bacterium comprising a variant binding polypeptide having improved expression, relative to the reference expression level, of the variant binding polypeptide by the presence of the labeled target molecule within the periplasm, wherein the presence of the labeled target molecule within the periplasm is due to binding to the variant binding polypeptide.

10. The method of claim 1, further comprising incubating the bacterium in growth medium prior to repeating the method.

11. The method of claim 6, wherein subjecting the bacterium to conditions that permeabilize the outer membrane of the bacterium comprises treating the bacterium with a permeabilization agent.

12. The method of claim 11, wherein the permeabilization agent is selected from the group consisting of a divalent cation chelator, NaCl, sucrose, an antibiotic, a detergent, lysozyme, Tris, Tris-EDTA, ascorbate, polylysine, benzalkonium chloride, protamine, bactericidal/permeability increasing protein (BPI), serum, complement, and $Ca^{2+}$.

13. The method of claim 12, wherein the divalent cation chelator is EDTA.

14. The method of claim 7, wherein resealing the outer membrane of the bacterium comprises contacting the bacterium with a salt of a cation selected from $Mg^{2+}$, $Mn^{2+}$, $Ca^{2+}$, $Zn^{2+}$, $Fe^{2+}$, $Na^+$ or $K^+$.

15. The method of claim 14, wherein the cation is $Mg^{2+}$.

16. The method of claim 15, wherein the salt of $Mg^{2+}$ is $MgCl_2$.

17. The method of claim 1, wherein the contacting step further comprises contacting the bacterium with a nucleic acid dye.

18. The method of claim 1, wherein the detectably labeled target molecule comprises a fluorescent label.

19. The method of claim 1, wherein removing unbound target molecules comprises at least one wash step comprising resuspending the bacterium in a wash buffer following contacting the bacterium with the detectably labeled target molecule.

20. The method of claim 1, wherein the sorting step comprises flow cytometry.

21. The method of claim 1, wherein the binding polypeptide is expressed in soluble form in the periplasm of the bacterium.

22. The method of claim 1, wherein the binding polypeptide is an antibody.

23. The method of claim 22, wherein the antibody is a full-length antibody.

24. The method of claim 23, wherein the full-length antibody is an IgG antibody.

25. The method of claim 22, wherein the antibody is a half-antibody.

26. The method of claim 22, wherein the antibody is an antibody fragment.

27. The method of claim 26, wherein the antibody fragment is selected from the group consisting of Fab, Fab'-SH, Fv, scFv, and $(Fab')_2$ fragments.

28. The method of claim 1, wherein step (a) comprises providing a plurality of bacteria, wherein the plurality of bacteria comprise a library of nucleic acids, each encoding a candidate binding polypeptide.

29. The method of claim 28, wherein the library comprises a plurality of nucleic acids encoding candidate antibody variants, wherein each candidate antibody variant comprises an amino acid residue alteration in an FR of the VH or VL as compared to a reference antibody, wherein the amino acid residue alteration: (a) was identified in a naturally occurring antibody having the same subtype as the reference antibody, and (b) is in an amino acid residue predicted to be solvent inaccessible.

30. The method of claim 29, wherein the amino acid residue alteration in the naturally occurring antibody is due to somatic hypermutation.

31. The method of claim 28, further comprising the step of identifying a candidate binding polypeptide as having (i) an increased expression level, relative to a reference expression level, based on the amount of the labeled target molecule within the periplasm, wherein the reference expression level is the expression level of a wild-type version of the binding polypeptide; or (ii) increased stability, relative to a reference stability, based on the amount of the labeled target molecule within the periplasm, wherein the reference stability is the stability of a wild-type version of the binding polypeptide.

32. The method of claim 1, further comprising isolating the nucleic acid following the sorting step.

33. The method of claim 1, wherein the bacterium comprises a mutation affecting a transcription-regulating gene selected from a transcription initiation factor, an anti-sigma factor, an RNA polymerase subunit, or a transcription factor.

34. A method for identifying a variant bacterium with improved expression, relative to a reference expression level, of a binding polypeptide that specifically binds a target molecule, wherein the reference expression level is the expression level of the binding polypeptide in a wild-type version of said variant bacterium, the method comprising the steps of:
(a) providing a variant bacterium having an outer membrane permeable to a molecule having a molecular weight greater than 10 kDa, the variant bacterium expressing a nucleic acid encoding a binding polypeptide, wherein the binding polypeptide is present within the periplasm of the variant bacterium, wherein the variant bacterium comprises a mutation that allows for diffusion of membrane-impermeant molecules across the outer membrane into the periplasm, wherein the mutation is in a gene encoding Lpp, and wherein the variant bacterium is a gram-negative bacterium;
(b) (i) contacting the variant bacterium with the target molecule which is detectably labeled under conditions such that the target molecule binds to the binding polypeptide within the periplasm and (ii) removing unbound target molecules; and
(c) sorting the variant bacterium having improved expression, relative to the reference expression level, of the binding polypeptide that specifically binds the target molecule by the presence of the labeled target molecule within the periplasm, wherein the presence of the labeled target molecule within the periplasm is due to binding to the binding polypeptide, wherein the variant bacterium remains viable following step (c).

35. A method for identifying a variant bacterium with improved expression, relative to a reference expression level, of a binding polypeptide that specifically binds a target molecule, wherein the reference expression level is the expression level of the binding polypeptide in a wild-type version of said variant bacterium, the method comprising the steps of:
(a) providing a variant bacterium comprising a mutation that allows for diffusion of membrane-impermeant molecules across the outer membrane into the periplasm, wherein the mutation is in a gene encoding Lpp, the variant bacterium expressing a nucleic acid encoding a binding polypeptide, wherein the binding polypeptide is present within the periplasm of the variant bacterium, and wherein the variant bacterium is a gram-negative bacterium;
(b) (i) contacting the variant bacterium with the target molecule which is detectably labeled under conditions such that the target molecule binds to the binding polypeptide within the periplasm and (ii) removing unbound target molecules; and
(c) sorting the variant bacterium comprising a binding polypeptide having improved expression, relative to the reference expression level, of the binding polypeptide that specifically binds the target molecule by the presence of the labeled target molecule within the periplasm, wherein the presence of the labeled target molecule within the periplasm is due to binding to the binding polypeptide, wherein the variant bacterium remains viable following step (c).

36. A method for identifying a variant bacterium with improved expression, relative to a reference expression level, of a binding polypeptide that specifically binds a target molecule, wherein the reference expression level is the expression level of the binding polypeptide in a wild-type version of said variant bacterium, the method comprising the steps of:
- (a) providing a variant bacterium expressing a nucleic acid encoding a binding polypeptide, wherein the binding polypeptide is present within the periplasm of the variant bacterium, wherein the variant bacterium comprises a mutation that allows for diffusion of membrane-impermeant molecules across the outer membrane into the periplasm, wherein the mutation is in a gene encoding Lpp, and wherein the variant bacterium is a gram-negative bacterium;
- (b) subjecting the variant bacterium to conditions that permeabilize the outer membrane of the variant bacterium;
- (c) contacting the variant bacterium with the target molecule which is detectably labeled under conditions such that the target molecule binds to the binding polypeptide within the periplasm;
- (d) resealing the outer membrane of the variant bacterium following step (c) and removing unbound target molecules; and
- (e) sorting the variant bacterium comprising a binding polypeptide having improved expression, relative to the reference expression level, of the binding polypeptide that specifically binds the target molecule by the presence of the labeled target molecule within the periplasm, wherein the presence of the labeled target molecule within the periplasm is due to binding to the binding polypeptide.

* * * * *